United States Patent
Shrader et al.

(10) Patent No.: US 11,203,773 B2
(45) Date of Patent: Dec. 21, 2021

(54) DESIGNER RIBOSOMES AND METHODS OF USE THEREOF FOR INCORPORATING NON-STANDARD AMINO ACIDS INTO POLYPEPTIDES

(71) Applicant: Yale University, New Haven, CT (US)

(72) Inventors: Alanna Schepartz Shrader, New Haven, CT (US); Wesley E. Robertson, New Haven, CT (US); Clarissa Melo Czekster, St. Andrews (GB)

(73) Assignee: YALE UNIVERSITY, New Haven, CT (US)

( * ) Notice: Subject to any disclaimer, the term of this patent is extended or adjusted under 35 U.S.C. 154(b) by 525 days.

(21) Appl. No.: 16/085,927

(22) PCT Filed: Mar. 17, 2017

(86) PCT No.: PCT/US2017/023005
§ 371 (c)(1),
(2) Date: Sep. 17, 2018

(87) PCT Pub. No.: WO2017/161295
PCT Pub. Date: Sep. 21, 2017

(65) Prior Publication Data
US 2019/0024128 A1 Jan. 24, 2019

Related U.S. Application Data

(60) Provisional application No. 62/309,853, filed on Mar. 17, 2016.

(51) Int. Cl.
*C12P 19/34* (2006.01)
*C12N 15/11* (2006.01)
*C12N 15/67* (2006.01)
*C12N 9/10* (2006.01)
*C12N 15/70* (2006.01)

(52) U.S. Cl.
CPC ............ *C12P 19/34* (2013.01); *C12N 9/104* (2013.01); *C12N 15/11* (2013.01); *C12N 15/67* (2013.01); *C12N 15/70* (2013.01); *C12Y 203/02012* (2013.01)

(58) Field of Classification Search
None
See application file for complete search history.

(56) References Cited

FOREIGN PATENT DOCUMENTS

| WO | 2014/176469 | 10/2014 |
|---|---|---|
| WO | 2014176469 | 10/2014 |
| WO | 2015/120287 | 8/2015 |
| WO | 2015120287 | 8/2015 |

OTHER PUBLICATIONS

Axup, et al., "Synthesis of site-specific antibody-drug conjugates using unnatural amino acids", PNAS, 109:16101-6 (2012).
Bain, et al., "Site-specific incorporation of nonnatural residues during in vitro protein biosynthesis with semisynthetic aminoacyl-tRNAs", Biochemistry, 30:541121 (1991).
Barry, "A broad-host-range shuttle system for gene insertion into the chromosomes of gram-negative bacteria", Gene, 71:75-84 (1980).
Beebee, et al., "A universal plate format for increased throughput of assays that monitor multiple aminoacyl transfer RNA synthetase activities", Anal Biochem, 368:111-21 (2007).
Beke, et al., "Toward a rational design of beta-peptide structures", J Comput Chem, 27 (1): 20-38 (2006).
Bruzzese, et al., "Development of a charcoal paper adenosine triphosphate:pyrophosphate exchange assay: kinetic characterization of NEDD8 activating enzyme", Anal Biochem, 394:24-9 (2009).
Calendar, et al., Purification and physical characterization of tyrosyl ribonucleic acid synthetases from *Escherichia coli* and Bacillus subtilis, Biochemistry, 5:168190 (1966).
Cheloha, et al., "Consequences of periodic α-to-β(3) residue replacement for immunological recognition of peptide epitopes", ACS Chem. Biol., 10:844-54 (2015).
Chin, "Expanding and reprogramming the genetic code of cells and animals", Ann Rev Biochem, 83:379-403 (2014).
Czekster, et al., "In Vivo Biosynthesis of a β-Amino Acid-Containing Protein", J. Am. Chem. Soc., 138 (16):5194-7(2016).
Daly and Hearn, Expression of heterologous proteins in Pichia pastoris: a useful experimental tool in protein engineering and production J. Mol. Recognit. 18(2):119-38 (2005).
Davis et al., "Designer proteins: applications of genetic code expansion in cell biology", Nat. Rev. Mol. Cell Biol., 13:168-82 (2012).
Dedkova, et al., "β-Puromycin selection of modified ribosomes for in vitro incorporation of β-amino acids", Biochemistry, 51(1):401-15 (2012).
Dedkova, et al., "Enhanced D-amino acid incorporation into protein by modified ribosomes", J Am Chem Soc, 125:6616 (2003).

(Continued)

*Primary Examiner* — Kagnew H Gebreyesus
(74) *Attorney, Agent, or Firm* — Pabst Patent Group LLP

(57) ABSTRACT

Engineered 23S rRNAs and methods of use thereof for translation of proteins incorporating non-standard amino acids are provided. Typically, the 23S rRNA includes one or more mutations at positions 2496-2507 relative to *E. coli* wildtype 23S rRNA, wherein a ribosome composed of the 23S rRNA can catalyze the covalent transfer of a non-standard amino acid from an aminoacyl-RNA onto a nascent peptide chain. For example, the 23S rRNA can include the sequence UGACUU at positions 2502-2507 relative to *E. coli* wildtype 23S rRNA, and optionally the sequence AGCGUGA from positions 2057-2063 relative to *E. coli* wildtype 23S rRNA. The 23S rRNA can include additional or alternative deletions, substitutions, insertions, or combination thereof. The compositions and methods can be used to make polypeptides and sequence defined polymers.

20 Claims, 6 Drawing Sheets
Specification includes a Sequence Listing.

(56) References Cited

OTHER PUBLICATIONS

Drahos, et al., "Tracking recombinant organisms in the environment: β galactosidase as a selectable non-antibiotic marker for fluorescent Pseudomonads", BioTech. 4:439-444 (1986).
Dumas, et al., "Designing logical codon reassignment—Expanding the chemistry in biology", Chem. Sci., 6:50-69 (2015).
Effraim, et al., "Natural amino acids do not require their native tRNAs for efficient selection by the ribosome", Nat Chem Biol, 5:947-53 (2009).
Ellman, et al., "Site-specific incorporation of novel backbone structures into proteins", Science, 255:197-200 (1992).
England, et al., "Backbone mutations in transmembrane domains of a ligand-gated ion channel: implications for the mechanism of gating", Cell, 96:89-98 (1999).
Englander, et al., "he ribosome can discriminate the chirality of amino acids within its peptidyl-transferase center", PNAS, 112:6038-43 (2015).
Fleer et al., "High-level secretion of correctly processed recombinant human interleukin-1 beta in Kluyveromyces lactis". Gene, 107:285-95 (1991).
Fujino, et al., "Ribosomal Synthesis of Peptides with Multiple β-Amino Acids", J Am Chem Soc, 138 (2016).
Gleitsman, "An intersubunit hydrogen bond in the nicotinic acetylcholine receptor that contributes to channel gating", Biol Chem, 283:35638-43 (2008).
Gleitsman, et al., "Probing the role of backbone hydrogen bonding in a critical beta sheet of the extracellular domain of a cys-loop receptor" ChemBioChem, 10:1385-91 (2009).
Goto, et al., "Flexizymes for genetic code reprogramming", Nat Prot, 6:779-90 (2011).
Grinter, et al., "Abroad-host-range cloning vector transposable to various replicons", Gene, 21:133-43 (1983).
Guichard, et al., "Melanoma peptide MART-1(27-35) analogues with enhanced binding capacity to the human class I histocompatibility molecule HLA-A2 by introduction of a beta-amino acid residue: implications for recognition by tumor-infiltrating lymphocytes", J. Med. Chem., 43:3803-8 (2000).
Guo, et al., "Addition of an alpha-hydroxy acid to the genetic code of bacteria", Angew Chem Int Ed, 47:722-5 (2008).
Hartman, et al., "Enzymatic aminoacylation of tRNA with unnatural amino acids", PNAS, 103:4356-61 (2006).
Heck, et al., "Enzymatic degradation of beta- and mixed alpha,beta-oligopeptides", Chem. Biodiversity, 3:1325-48 (2006).
Herrero, et al., "Transposon vectors containing non-antibiotic resistance selection markers for cloning and stable chromosomal insertion of foreign genes in gram-negative bacteria", J. Bacteriology, 172(11):6557-67 (1990).
Hitzeman, et al., "Isolation and Characterization of the Yeast 3-Phosphoglycerokinase Gene (PGK) by an immunological Screening Technique", J. Biol. Chem. 255:2073 (1980).
Holland, et al., "Isolation and Identification of Yeast Messenger Ribonucleic Acids Coding for Enolase, Glyceraldehyde-3-Phosphate Dehydrogenase, and Phosphoglycerate Kinase", Biochem., 17:4900-7 (1978).
Hook, et al., "The proteolytic stability of 'designed' beta-peptides containing alpha-peptide-bond mimics and of mixed alpha,beta-peptides: application to the construction of MHC-binding peptides", Chem. Biodiversity, 2, 591-632 (2005).
Hyrup, et al., "Peptide nucleic acids (PNA): synthesis, properties and potential applications", Bioorgan. Med. Chem., 4:5-23 (1996).
Isaacs, et al., "Precise manipulation of chromosomes in vivo enables genome-wide codon replacement", Science, 333:348-53 (2011).
Jansen, et al., "Drag&Drop cloning in yeast", Gene 344:43-51 (2005).
Joseph-Liauzun, et al., "Transposable elements for efficient manipulation of a wide range of gram-negative bacteria: promoter probes and vectors for foreign genes", Gene, 85:83-9 (1989).
Jude, et al., "Peptide backbone chemistry and membrane channel function: effects of a single amide-to-ester replacement on gramicidin channel structure and function", Biochemistry, 40:1460-72 (2001).
Kanatani, et al., "Asimple approach to sense codon-templated synthesis of natural/unnatural hybrid peptides", Nucl Acids Symp Ser, 49:265-6 (2005).
Kao, et al., "A simple and efficient method to transcribe RNAs with reduced 3' heterogeneity", Methods, 23:201-5 (2001).
Kavran, et al., "Structure of pyrrolysyl-tRNA synthetase, an archaeal enzyme for genetic code innovation", PNAS, 104:11268-73 (2007).
Kawakami, et al., "Ribosomal synthesis of polypeptoids and peptoid-peptide hybrids", J Am Chem Soc, 130:16861-3 (2008).
Kobayashi, et al., "Structural snapshots of the KMSKS loop rearrangement for amino acid activation by bacterial tyrosyl-tRNA synthetase", Mol Biol, 346:105-17 (2005).
Lajoie, et al., "Genomically recoded organisms expand biological functions.", Science 342:357-60 (2013).
Lajoie, et al., "Probing the limits of genetic recoding in essential genes", Science, 342, 361-3 (2013).
Lariviere, et al., "Uniform binding of aminoacyl-tRNAs to elongation factor Tu by thermodynamic compensation", Science, 294:165-8 (2001).
Leatherbarrow, et al., Transition-state stabilization in the mechanism of tyrosyl-tRNA synthetase revealed by protein engineering PNAS, 82:7840-4 (1985).
Leong, et al., "Inefficient delivery but fast peptide bond formation of unnatural L-aminoacyl-tRNAs in translation", J Am Chem Soc, 134:17955-62 (2012).
Leong, et al., "A tRNA body with high affinity for EF-Tu hastens ribosomal incorporation of unnatural amino acids", RNA, 20:632-43 (2014).
Li, et al., "Usage of an intronic promoter for stable gene expression in *Saccharomyces cerevisiae*", Lett Appl Microbiol. 40(5):347-52 (2005).
Liu et al., "Adding new chemistries to the genetic code", Annu. Rev. Biochem., 79:413-44 (2010).
Liu, et al., "Condensed *E. coli* cultures for highly efficient production of proteins containing unnatural amino acids", Bioorg Med Chem Lett, 20:5613-6 (2010b).
Lu, et al., "Probing ion permeation and gating in a K+ channel with backbone mutations in the selectivity filter", Nature Neuroscience, 4:239-46 (2001).
Lutz, etaL, "Sequence-Controlled Polymers", Science, 341(6146):1238149. doi: 10.1126 (2013).
Ma, et al., "Structure Activity Related, Mechanistic, and Modeling Studies of Gallotannins containing a Glucitol-Core and α-Glucosidase", RSC Advances, 5:39580 (2015).
Mahdavi, et al., "A genetically encoded and gate for cell-targeted metabolic labeling of proteins", J Am Chem Soc, 135:2979-82 (2013).
Maini, et al., "Protein Synthesis with Ribosomes Selected for the Incorporation of β-Amino Acids", Biochemistry, 16;54(23):3694-706 (2015a).
Maini, et al., "Incorporation of beta-amino acids into dihydrofolate reductase by ribosomes having modifications in the peptidyltransferase center", Bioorg Med Chem, 21, 1088-96 (2013).
Maini, et al., "Ribosome-Mediated Incorporation of Dipeptides and Dipeptide Analogues into Proteins in Vitro", J Am Chem Soc., 137(35):11206-9 (2015b).
Masson and Miller, "Expression of synthetic suppressor tRNA genes under the control of a synthetic promoter", Gene, 47:179-183 (1986).
Meinnel, et al., Fast purification of a functional elongator tRNAmet expressed from a synthetic gene in vivo Nucleic Acids Res., 16:8095-6 (1988).
Mermershtain, et al., "Idiosyncrasy and identity in the prokaryotic Phe-system: crystal structure of *E. coli* phenylalanyl-tRNA synthetase complexed with phenylalanine and AMP", Prot Sci, 20:160-7 (2011).
Merryman, et al., "Methods and applications for assembling large DNA constructs", Metab Eng, 14:196-204(2012).
Miller, et al., "Asynthetic tRNA for EF-Tu mediated selenocysteine incorporation in vivo and in vitro", FEBS Lett, 589:2194-9 (2015).
Morris, et al., "Automated docking using a Lamarckian genetic algorithm and an empirical binding free energy function", J Comp Chem, 19:1639 (1998).

(56) References Cited

OTHER PUBLICATIONS

Murakami, et al., "A highly flexible tRNA acylation method for non-natural polypeptide synthesis", Nat Meth, 3:357-9 (2006).
Nagaoka, et al., "Peptide backbone mutagenesis of putative gating hinges in a potassium ion channel", ChemBioChem, 9:1725-8 (2008).
O'Donoghue, et al., "Upgrading protein synthesis for synthetic biology", Nat Chem Bio, 9:594-8 (2013).
Ohta, et al., "Polymerization of alpha-hydroxy acids by ribosomes", ChemBiochem, 9:2773-8 (2008).
Ohtsuki, et al., "Use of EF-Tu mutants for determining and improving aminoacylation efficiency and for purifying aminoacyl tRNAs with non-natural amino acids", Biochem, 148:239-46 (2010).
Park, et al., "Expanding the genetic code of *Escherichia coli* with phosphoserine", Science, 333:1151-4 (2011).
Pleiss, et al., "Identification of thermodynamically relevant interactions between EF-Tu and backbone elements of tRNA", J Mol Biol, 308:895-905 (2001).
Ponchon and Dardel, "Recombinant RNA technology: the tRNA scaffold", Nature Methods, 4(7):571-6 (2007).
Pronk, et al., "GROMACS 4.5: a high-throughput and highly parallel open source molecular simulation toolkit", E. Bioinform, 29:845-54 (2013).
Raibaud, et al., "A technique for integrating any DNA fragment into the chromosome of *Escherichia coli*", Gene, 29:231-41 (1984).
Reinelt, et al., "Beta-amino acid scan of a class I major histocompatibility complex-restricted alloreactive T-cell epitope", Biol. Chem., 276:24525-30 (2011).
Rienzo, et al., "Structural requirements in the transmembrane domain of GLIC revealed by incorporation of noncanonical histidine analogs", Chem Bio., 21:1700-6 (2014).
Sanderson, et al., "Exploring the specificity of bacterial elongation factor Tu for different tRNAs", Biochemistry, 46:6194-6200 (2007).
Seebach, et al., "Bacterial beta-peptidyl aminopeptidases with unique substrate specificities for beta-oligopeptides and mixed beta,alpha-oligopeptides", FEBS J., 273:5261-72 (2006).
Subtelny, et al., "Ribosomal synthesis of N-methyl peptides", J Am Chem Soc, 130:6131-6 (2008).
Summerton and Weller, "Morpholino antisense oligomers: design, preparation, and properties", Antisense Nucleic Acid Drug Dev., 7:187-195 (1997).
Tabb, et al., "MyriMatch: highly accurate tandem mass spectral peptide identification by multivariate hypergeometric analysis.", J Proteome Res, 6:654-61 (2007).
Taxis and Knop, "System of centromeric, episomal, and integrative vectors based on drug resistance markers for *Saccharomyces cerevisiae*", Bio/Tech., 40(1):73-8 (2006).
Tisné, et al., "NMR and biochemical characterization of recombinant human tRNA(Lys)3 expressed in *Escherichia coli*: identification of posttranscriptional nucleotide modifications required for efficient initiation of HIV-1 reverse transcription", RNA, 6:1403-12 (2000).
Tsiodras, et al., "Diversity of domain V of 23S rRNAgene sequence in different Enterococcus", J Clin Microbiol., 38(11):3991-3 (2000).
Wang, et al., "β-Peptide bundles: Design. Build. Analyze. Biosynthesize", Chem. Commun., 52:7420-32 (2016).
Wang, et al., "Kinetics of Ribosome-Catalyzed Polymerization Using Artificial Aminoacyl-tRNA Substrates Clarifies Inefficiencies and Improvements", ACS Chem Bio, 10:2187-92 (2015).
Wang, et al., "Peptide formation by N-methyl amino acids in translation is hastened by higher pH and tRNA(Pro)", ACS Chem Biol, 9:1303-11 (2014).
Way, et al., "New Tn10 derivatives for transposon mutagenesis and for construction of lacZ operon fusions by transposition", Gene, 32:369-79 (1984).
Webb, et al., "T cell determinants incorporating beta-amino acid residues are protease resistant and remain immunogenic in vivo", J. Immunol., 175:3810-8 (2005).
Young, "An enhanced system for unnatural amino acid mutagenesis in *E. coli*", J. MoL Biol., 395(2):361-74 (2010).
International Search Report for PCT/US2017/023005 dated May 29, 2017.

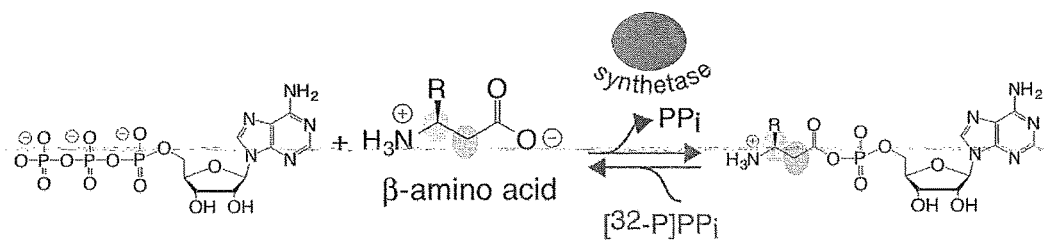
FIG. 1F
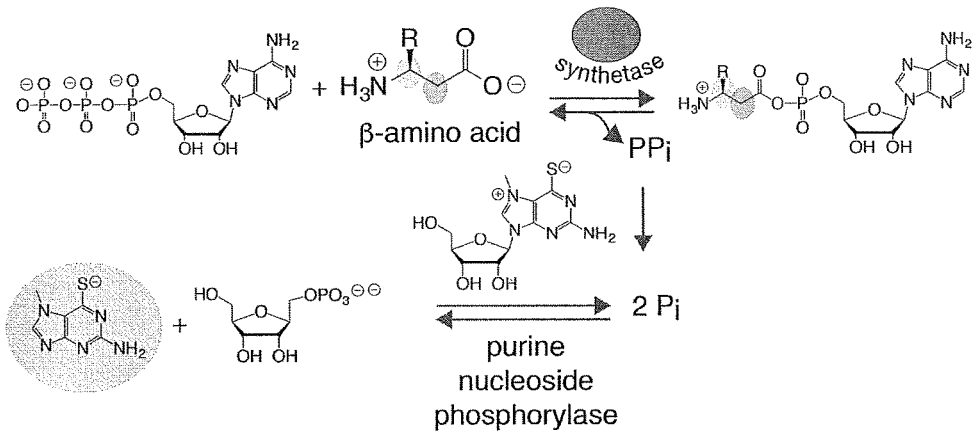
FIG. 1G
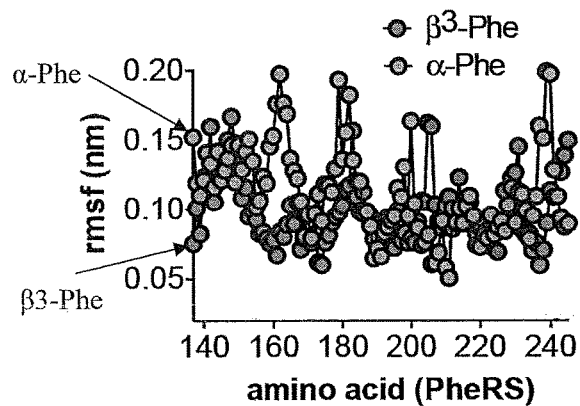
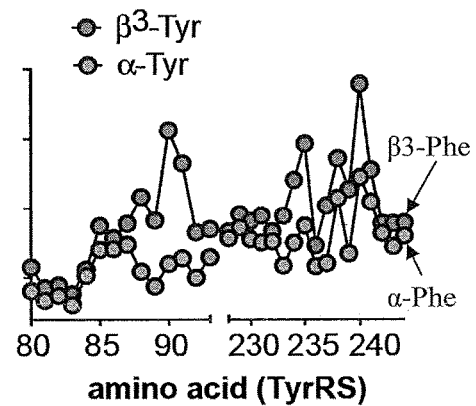
FIG. 2A
FIG. 2B

DESIGNER RIBOSOMES AND METHODS OF USE THEREOF FOR INCORPORATING NON-STANDARD AMINO ACIDS INTO POLYPEPTIDES

CROSS-REFERENCE TO RELATED APPLICATIONS

This application is a National Phase application under 35 U.S.C. 371 of PCT/US2017/023005 filed Mar. 17, 2017 entitled "DESIGNER RIBOSOMES AND METHODS OF USE THEREOF FOR INCORPORATING NON-STANDARD AMINO ACIDS INTO POLYPEPTIDES" which claims benefit of and priority to U.S. Provisional Application No. 62/309,853, filed Mar. 17, 2016, which are hereby incorporated herein by reference in their entirety.

STATEMENT REGARDING FEDERALLY SPONSORED RESEARCH

This invention was made with government support under 1122492 awarded by National Science Foundation. The government has certain rights in the invention.

REFERENCE TO SEQUENCE LISTING

The Sequence Listing submitted as a text file named "YU_6929_PCT_ST25.txt," created on Mar. 17, 2017, and having a size of 21,036 bytes is hereby incorporated by reference pursuant to 37 C.F.R. § 1.52(e)(5).

FIELD OF THE INVENTION

The field of the present invention generally relates to compositions and methods for incorporation of non-standard amino acids into proteins and peptides and other oligomers during translation.

BACKGROUND OF THE INVENTION

Template-guided polymerization is the chemical foundation of the central dogma. It facilitates the evolution of natural biopolymers for greater fitness, and, when co-opted for engineering, can optimize biopolymer sequence to define structure and promote function (Lutz, et al., *Science*, 341: 628 (2013)). The machine used for template-guided protein polymerization—the 2.5 MDa behemoth known as the ribosome—has been exploited for over 20 years to site-specifically incorporate >150 unnatural α-amino acids into proteins, in vitro, in cells, and in an animal (O'Donoghue, et al., *Nat Chem Bio*, 9 (2013); Liu, et al., *Ann Rev Biochem*, 79:413 (2010); Chin, *Ann Rev Biochem*, 83:379 (2014)). These efforts have deepened the understanding of protein function, established a foundation for education/training at an interdisciplinary frontier, and provided commodities such as antibody-drug conjugates, modified therapeutics, and biomaterials to benefit society (Axup, et al., *Proc Natl Acad Sci USA*, 109:16101 (2012)). Yet, even after two-plus decades of groundbreaking research, the potential of the translational apparatus remains underexploited, especially in vivo (Ellman, et al., *Science*, 255:197 (1992); Kawakami, et al., *J Am Chem Soc*, 130:16861 (2008); Guo, et al., *Angew Chem Int Ed*, 47:722 (2008); Subtelny, et al., *J Am Chem Soc*, 130:6131 (2008); Englander, et al., *Proc Natl Acad Sci USA*, 112:6038 (2015)). Although a number of backbone-modified amino acids, including some β-amino acids (Fujino, et al., *J Am Chem Soc*, 138 (2016)), can be introduced into proteins by wild type ribosomes in vitro using chemically mis-acylated tRNAs, (Subtelny, et al., *J Am Chem Soc*, 130:6131 (2008); Englander, et al., *Proc Natl Acad Sci USA*, 112:6038 (2015); Bain, et al., *Biochemistry*, 30:5411 (1991); Dedkova, et al., *J Am Chem Soc*, 125:6616 (2003); Merryman, et al., *Metab Eng*, 14:196 (2012); Murakami, et al., *Nat Meth*, 3:357 (2006); Goto, et al., *Nat Prot*, 6:779 (2011); Leong, et al., *RNA*, 20:632 (2014); Wang, et al., *ACS Chem Bio*, 10:2187 (2015); Maini, et al., *J Am Chem Soc*, 137: 11206 (2015)). It is believed the experiments disclosed herein provide the first example in which a β-amino acid has been successfully introduced into a protein in a cell (Guo, et al., *Angew Chem Int Ed*, 47:722 (2008), Ma, et al., *RSC Advances*, 5:39580 (2015); England, et al., *Cell*, 96:89 (1999); Jude, et al., *Biochemistry*, 40:1460 (2001); Lu, et al., *Nature Neuroscience*, 4:239 (2001); Gleitsman, *Biol Chem*, 283:35638 (2008); Gleitsman, et al., *ChemBioChem*, 10:1385 (2009); Nagaoka, et al., *ChemBioChem*, 9:1725 (2008); Rienzo, et al., *Chem Bio.*, 21:1700 (2014).

It was recently reported that ribosomes from certain erythromycin-resistant *E. coli* mutants, when isolated in S30 cell extracts and incubated in vitro with the appropriate chemically mis-acylated tRNA, can incorporate certain $\beta^3$-amino acids into full length DHFR (Dedkova, et al., *Biochemistry*, 51:401 (2012); Maini, et al., *Biochemistry* (2015); Maini, et al., *Bioorg Med Chem*, 21:1088 (2013)). Of five $\beta^3$-amino acids tested, β-Ar (FIG. 1A-1B) exhibited the highest incorporation efficiency (18.4% read through). But the translational apparatus is a complex machine, and it is widely accepted that many parts—especially aminoacyl-tRNA synthetase/tRNA pairs and EF-Tu, which generate and then deliver aminoacyl-tRNAs to the ribosome, respectively—need to be reconfigured or upregulated (Dedkova, et al., *Biochemistry*, 51:401 (2012)) before $\beta^3$-amino acids could be incorporated efficiently and elongated into proteins in vivo.

Protein therapeutics represent the majority of new drug applications, as well as more than one third of FDA-approved drugs in 2014. This trend is likely to continue as researchers increasingly learn to leverage the strengths of protein drugs, including their evolvability, specificity, target-binding affinity, ability to disrupt protein-protein interfaces, and ability to catalyze chemical reactions. Extending the physiological lifetime and reducing the immunogenicity of protein therapeutics by selective β-amino acid incorporation will improve human therapeutics. Such an impact would transform human medicine and has the potential to create a new biotechnological sub-economy as well as corresponding educational opportunities.

Therefore, it is an object of the invention to provide compositions and methods of preparation of polypeptides having one or more non-standard amino acids, particularly, one or more $\beta^3$-amino acids, in vivo.

It is a further object of the invention to provide 23S rRNA and ribosomes thereof with an improved ribosomal peptidyl transferase activity for $\beta^3$-amino acids.

SUMMARY OF THE INVENTION

Engineered 23S rRNAs and methods of use thereof for translation of proteins incorporating non-standard amino acids are provided. Typically, the 23S rRNA includes one or more mutations at positions 2496-2507 relative to *E. coli* wildtype 23S rRNA (e.g., SEQ ID NO:1) and the corresponding sequence in 23S mutant 040329, wherein a ribosome composed of the mutated 23S rRNA can catalyze the covalent transfer of a non-standard amino acid from an aminoacyl-RNA onto a nascent peptide chain. For example, the 23S rRNA can include the sequence UGACUU at positions 2502-2507 relative to *E. coli* wildtype 23S rRNA, and, optionally, the sequence AGCGUGA from positions 2057-2063 relative to *E. coli* wildtype 23S rRNA. The 23S rRNA can include additional or alternative deletions, substitutions, insertions, or combination thereof. For example, the 23S rRNA can have a truncated 5' end, a truncated 3' end, or a combination thereof relative to wildtype. The non-standard amino acid can be a non-α amino acid, for example, a β-amino acid such as a $β^3$-amino acid.

In particular embodiments, an engineered 23S rRNA includes a peptidyl transferase center, wherein the peptidyl transferase center is a variant of *E. coli* wildtype 23S rRNA having the sequence UGACUU at positions 2502-2507 and optionally, but preferably, the sequence AGCGUGA from positions 2057-2063 relative to *E. coli* wildtype 23S rRNA. Exemplary 23S rRNAs include SEQ ID NO:4 and functional fragments and variants thereof.

Ribosomes including the engineered 23S rRNA and polynucleotides encoding the 23S rRNA are also provided. The polynucleotide can be operatively linked to an expression control sequence. The polynucleotide can be introduced in a host cell and expressed extrachromosomally (e.g., from an expression vector such as a plasmid), or integrated or incorporated in the host's genome. The host cell is a prokaryote or a eukaryote. In preferred embodiments, the host cell is a prokaryote, for example, a bacterium, such as *E. coli*. The host cell can be a genomically recoded organism (GRO).

Methods of making polypeptides incorporating one or more non-standard amino acids, and polypeptides made therefrom are also provided. For example, a method for site specific incorporation of a non-standard amino acid into a target protein can include expressing a messenger RNA (mRNA) encoding the target protein in a system including: canonical amino acids, at least one non-standard amino acid, ribosomes, aminoacyl tRNA synthetases, tRNAs, and EF-Tu, preferably wherein the ribosomes include the disclosed 23S rRNA; at least one aminoacyl tRNA synthetase (AARS) that can aminoacylate a tRNA (or a tRNA surrogate) with the non-standard amino acid; at least one tRNA (or surrogate) that can be aminoacylated with the non-standard amino acid to form an aminoacylated-tRNA that recognizes at least one codon in the mRNA encoding the target protein; and an elongation factor (EF-TU) that binds the aminoacylated-tRNA aminoacylated with the non-standard amino acid; wherein the aminoacylated-tRNA with the non-standard amino acid recognizes at least one codon such that non-standard amino acid is incorporated into a protein or polypeptide during translation. The non-standard amino acid can be a non-α amino acid, for example a β amino acid such as a $β^3$-amino acid.

The AARS that aminoacylates a tRNA with the non-standard amino acid can be, for example, wildtype *E. coli* MetRS, PheRS, GluRS, GlyRS, TyrRS, or a combination thereof. In some embodiments, the AARS that aminoacylates a tRNA with the non-standard amino acid is phenylalanyl-tRNA synthetase (PheRS) and the non-standard amino acid is a $β^3$-Phe derivative. The AARS-tRNA can be an orthogonal pair.

The incorporation of the non-standard amino acid into a target protein can occur in vivo in a host cell, or in vitro in, for example, a cell-free translation system. The host cell can be a prokaryote, for example a bacterium such as *E. coli*. Any of the components of the translation system, including but not limited to the ribosomes (and components thereof such as 23S rRNA), AARS, tRNA, mRNA, and EF-Tu can be wildtype, variants, or heterologous to the host. In some embodiments, the host cell is a genomically recoded organism.

The compositions and methods can be used to make polypeptide and sequence defined polymers having one or more iterations of one of more non-standard amino acids. Exemplary polymers include sequence-defined polyolefins, aramids, polyurethanes, and polycarbonates.

BRIEF DESCRIPTION OF THE DRAWINGS

FIG. 1F is an illustration of an assay used to monitor the rate of adenylation of α- and β-amino acids catalyzed by *E. coli* PheRS, GlyRS, MetRS, and GluRS. FIG. 1G is an illustration of an assay used to monitor the rate of adenylation of α- and β-amino acids catalyzed by *E. coli* TyrRS. MESG is 2-amino-6-mercapto-7-methylpurine.

FIGS. 2A and 2B are plots of atom-averaged root mean square fluctuations (rmsf) of the indicated amino acids by residue number for PheRS (2A) and TryRS (2B).

DETAILED DESCRIPTION OF THE INVENTION

I. Definitions

Figure 1A:
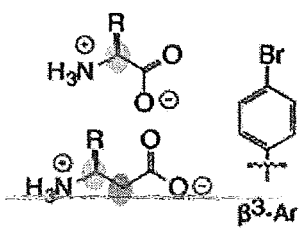
FIG. 1A is an illustration comparing the structures of α- and $β^3$-amino acids and the structure of β-ArA, a β-amino acid analog of phenyl glycine.

As used herein, the terms "transfer RNA" and "tRNA" refers to a set of genetically encoded RNAs that act during protein synthesis as adaptor molecules, matching individual amino acids to their corresponding codon on a messenger RNA (mRNA). In higher eukaryotes such as mammals, there is at least one tRNA for each of the 20 naturally occurring amino acids. In eukaryotes, including mammals, tRNAs are encoded by families of genes that are 73 to 150 base pairs long. tRNAs assume a secondary structure with four base paired stems known as the cloverleaf structure. The tRNA contains a stem and an anticodon. The anticodon is complementary to the codon specifying the tRNA's corresponding amino acid. The anticodon is in the loop that is opposite of the stem containing the terminal nucleotides. The 3' end of a tRNA is aminoacylated by a tRNA synthetase so that an amino acid is attached to the 3'end of the tRNA. This amino acid is delivered to a growing polypeptide chain as the anticodon sequence of the tRNA reads a codon triplet in an mRNA.

As used herein, the term "anticodon" refers to a unit made up of typically three nucleotides that correspond to the three bases of a codon on the mRNA. Each tRNA contains a specific anticodon triplet sequence that can base-pair to one or more codons for an amino acid or "stop codon." Known "stop codons" include, but are not limited to, the three codon bases, UAA known as ochre, UAG known as amber and UGA known as opal, which do not code for an amino acid but act as signals for the termination of protein synthesis. tRNAs do not decode stop codons naturally, but can and have been engineered to do so. Stop codons are usually recognized by enzymes (release factors) that cleave the polypeptide as opposed to encode an amino acid via a tRNA.

As used herein, the term "suppressor tRNA" refers to a tRNA that alters the reading of a messenger RNA (mRNA) in a given translation system. For example, a non-sense suppressor tRNA can read through a stop codon.

As used herein, the term "aminoacyl tRNA synthetase (AARS)" refers to an enzyme that catalyzes the esterification of a specific amino acid or its precursor to one of all its compatible cognate tRNAs to form an aminoacyl-tRNA. These charged aminoacyl tRNAs then participate in mRNA translation and protein synthesis. The AARS show high specificity for charging a specific tRNA with the appropriate amino acid. In general, there is at least one AARS for each of the twenty amino acids.

As used herein, the term "residue" refers to an amino acid that is incorporated into a protein. The amino acid may be a naturally occurring amino acid and, unless otherwise limited, may encompass known analogs of natural amino acids that can function in a similar manner as naturally occurring amino acids.

As used herein, the terms "polynucleotide" and "nucleic acid sequence" refers to a natural or synthetic molecule including two or more nucleotides linked by a phosphate group at the 3' position of one nucleotide to the 5' end of another nucleotide. The polynucleotide is not limited by length and can include deoxyribonucleic acid (DNA) or ribonucleic acid (RNA).

As used herein, the term "vector" refers to a polynucleotide capable of transporting into a cell another polynucleotide to which the vector sequence has been linked. "Vector" can refer to a replicon, such as a plasmid, phage, or cosmid, into which another DNA segment may be inserted so as to bring about the replication of the inserted segment. The vectors can be expression vectors. "Plasmid" and "vector" are used interchangeably, as a plasmid is a commonly used form of vector.

As used herein, the term "expression vector" includes any vector, (e.g., a plasmid, cosmid or phage chromosome) containing a gene construct in a form suitable for expression by a cell (e.g., linked to a transcriptional control element). Thus an expression vector can include one or more expression control sequences.

As used herein, the term "expression control sequence" refers to a DNA sequence that controls and regulates the transcription and/or translation of another DNA sequence. Control sequences that are suitable for prokaryotes, for example, include a promoter, optionally an operator sequence, a ribosome binding site, and the like. Eukaryotic cells are known to utilize promoters, polyadenylation signals, and enhancers.

As used herein, the term "promoter" refers to a regulatory nucleic acid sequence, typically located upstream (5') of a gene or protein coding sequence that, in conjunction with various elements, is responsible for regulating the expression of the gene or protein coding sequence. These include constitutive promoters, inducible promoters, tissue- and cell-specific promoters and developmentally-regulated promoters.

As used herein, the term "operatively linked to" refers to the functional relationship of a nucleic acid with another nucleic acid sequence, or to a protein sequence with another protein sequence. Promoters, enhancers, transcriptional and translational stop sites, and other signal sequences are examples of nucleic acid sequences operatively linked to other sequences. For example, operative linkage of gene to a transcriptional control element refers to the physical and functional relationship between the gene and promoter such that the transcription of the gene is initiated from the promoter by an RNA polymerase that specifically recognizes, binds to and transcribes the DNA.

As used herein, the terms "transformation" and "transfection" refer to the introduction of a polynucleotide, e.g., an expression vector, into a recipient cell including introduction of a polynucleotide to the chromosomal DNA of the cell.

As used herein, the term "conservative variant" refers to a particular nucleic acid sequence that encodes identical or essentially identical amino acid sequences. Conservative substitution tables providing functionally similar amino acids are well known in the art. The following sets forth exemplary groups which contain natural amino acids that are "conservative substitutions" for one another. Conservative Substitution Groups 1 Alanine (A) Serine (S) Threonine (T); 2 Aspartic acid (D) Glutamic acid (E); 3 Asparagine (N) Glutamine (Q); 4 Arginine (R) Lysine (K); 5 Isoleucine (I) Leucine (L) Methionine (M) Valine (V); and 6 Phenylalanine (F) Tyrosine (Y) Tryptophan (W).

As used herein, the term "percent (%) sequence identity" or "homology" refers to the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

As used herein, the term "transgenic organism" refers to any organism, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. Suitable transgenic organisms include, but are not limited to, bacteria, cyanobacteria, fungi, plants and animals. The nucleic acids described herein can be introduced into the host by methods known in the art, for example infection, transfection, transformation or transconjugation.

As used herein, the term "eukaryote" or "eukaryotic" refers to organisms or cells or tissues derived from these organisms belonging to the phylogenetic domain Eukarya such as animals (e.g., mammals, insects, reptiles, and birds), ciliates, plants (e.g., monocots, dicots, and algae), fungi, yeasts, flagellates, microsporidia, and protists.

As used herein, the term "prokaryote" or "prokaryotic" refers to organisms including, but not limited to, organisms of the Eubacteria phylogenetic domain, such as *Escherichia coli, Thermus thermophilus*, and *Bacillus stearothermophilus*, or organisms of the Archaea phylogenetic domain such as, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii*, and *Aeuropyrum pernix*.

As used herein, the term "construct" refers to a recombinant genetic molecule having one or more isolated polynucleotide sequences. Genetic constructs used for transgene expression in a host organism include in the 5'-3' direction, a promoter sequence; a sequence encoding a gene of interest; and a termination sequence. The construct may also include selectable marker gene(s) and other regulatory elements for expression.

As used herein, the term "gene" refers to a DNA sequence that encodes through its template or messenger RNA a sequence of amino acids characteristic of a specific peptide, polypeptide, or protein. The term "gene" also refers to a DNA sequence that encodes an RNA product, for example a functional RNA that does not encode a protein or polypeptide (e.g., miRNA, tRNA, etc.). The term gene as used herein with reference to genomic DNA includes intervening, non-coding regions as well as regulatory regions and can include 5' and 3'untranslated ends.

As used herein, the term "isolated" is meant to describe a compound of interest (e.g., nucleic acids) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids are at least 60% free, preferably 75% free, and most preferably 90% free from other associated components. The term "isolated" as used herein with respect to nucleic acids also includes the combination with any non-naturally-occurring nucleic acid sequence, since such non-naturally-occurring sequences are not found in nature and do not have immediately contiguous sequences in a naturally-occurring genome.

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the term "translation system" refers to the components necessary to incorporate an amino acid into a growing polypeptide chain (protein). Key components of a translation system generally include amino acids, ribosomes, tRNAs, AARS, EF-Tu, and mRNA. The components described herein can be added to a translation system, in vivo or in vitro, to incorporate amino acids into a protein.

As used herein, the term "orthogonal translation system (OTS)" refers to at least an AARS and paired tRNA that are both heterologous to a host or translational system in which they can participate in translation of an mRNA including at least one codon that can hybridize to the anticodon of the tRNA.

As used herein, the terms "recoded organism" and "genomically recoded organism (GRO)" in the context of codons refer to an organism in which the genetic code of the organism has been altered such that a codon has been eliminated from the genetic code by reassignment to a synonymous or non-synonymous codon.

As used herein, "genetically modified organism (GMO)" refers to any organism whose genetic material has been modified (e.g., altered, supplemented, etc.) using genetic engineering techniques. The modification can be extrachromasomal (e.g., an episome, plasmid, etc.), by insertion or modification of the organism's genome, or a combination thereof.

As used herein, the term "polyspecific" refers to an AARS that can accept and incorporate two or more different amino acids.

As used herein, the terms "protein," "polypeptide," and "peptide" refers to a natural or synthetic molecule having two or more amino acids linked by the carboxyl group of one amino acid to the alpha amino group of another. The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus.

As used herein, "standard amino acid" and "canonical amino acid" refer to the twenty alpha- ($\alpha$) amino acids that are encoded directly by the codons of the universal genetic code denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, "non-standard amino acid (nsAA)" refers to any and all amino acids that are not a standard amino acid. Non-standard amino acids include beta- ($\beta$-), gamma- ($\gamma$-) or delta- ($\delta$-) amino acids, or derivatives of anthranilic acid, or dipeptide units containing any of these variants. nsAA can be created by enzymes through posttranslational modifications; or those that are not found in nature and are entirely synthetic (e.g., synthetic amino acids (sAA)). In both classes, the nsAAs can be made synthetically.

As used herein, "040329" refers to a mutant 23S rRNA with 13 base changes relative to wildtype E. coli 23S rRNA, specifically, the sequence AGCGUGA from 2057-2063 and the sequence UGGCAG at positions 2502-2507 (Dedkova, et al., Biochemistry, 51(1):401-15 (2012)).

As used herein, "040329 ribosome" refers to a ribosome including 040329 mutant 23S rRNA.

II. Designer Ribosomes

Genetically engineered, non-naturally occurring 23S rRNAs, nucleic acids encoding the 23S rRNAs, transfected and genetically modified cells expressing the 23S rRNAs, and ribosomes composed of the 23S rRNAs are provided. Ribosomes including engineered 23S rRNAs have an increased ability to incorporate non-standard, non-natural, non-α-amino acids (NNAs) into protein during in vivo translation or in an in vitro translation system. For example, in some embodiments, the dipeptides, or non-standard-, non-natural-, or non-α-amino acids:α-amino acid incorporation ratio of the disclosed ribosomes, when used in combination with other translation machinery that tolerates incorporation of non-standard, non-natural, or non-α-amino acids, is greater than that of wildtype ribosomes or ribosomes including known 23S mutants such as 040329.

Non-standard-, non-natural-, and non-α-amino acids are known in the art. For example, WO 2015/120287 provides a non-exhaustive list of exemplary non-standard and synthetic amino acids that are known in the art (see, e.g., Table 11 of WO 2015/120287).

The non-α-amino acid can be a β-amino acid, for example a $β^2$- or $β^3$-amino acid. Two main types of β-peptides exist: those with the organic residue (R) next to the amine are called $β^3$-peptides and those with position next to the carbonyl group are called $β^2$-peptides (see FIG. 1A).

The backbones of β-peptides are longer than those of α-amino acid peptides because β-peptides contain an additional backbone CH2 group (commonly called a methylene group). β-peptides can form many different types of helical structures, and the conformation types can be distinguished by the number of atoms in the hydrogen-bonded ring that is formed in solution; 8-helix, 10-helix, 12-helix, 14-helix, and 10/12-helix have been reported. Generally speaking, β-peptides form a more stable helix than α-peptides and are stable against proteolytic degradation in vitro and in vivo, an important advantage over natural peptides in the preparation of peptide-based drugs (Beke, et al., J Comput Chem, 27 (1): 20-38 (2006).

In particular embodiments, the $β^3$-amino acid is $β^3$-(p-Br)Phe. The β-amino acid/α-amino acid incorporation ratio of ribosomes including the disclosed engineered 23S rRNA is greater than that of wildtype ribosomes or ribosomes including known 23S mutants such as 040329. Thus, in specific embodiments the $β^3$-(p-Br)Phe/α-Phe incorporation ratio is greater than that of wildtype ribosomes or ribosomes including a known 23S mutant such as 040329.

An increase in incorporation ratio of the dipeptide, or non-standard-, non-natural-, or non-α-amino acid: α-amino acid can be any integer "n" between 1 and 1,000-fold inclusive, or more than 1,000-fold. In preferred embodiments, the incorporation ratio of the dipeptide, or non-standard-, non-natural-, or non-α-amino acid: α-amino acid by ribosomes including the disclosed 23S rRNA is at least 3-fold greater than ribosomes including 040329 mutant 23S rRNA.

A. Engineered 23S rRNA

Engineered 23S rRNAs are provided. The engineered rRNAs have one or more mutations at positions 2496-2507 relative to E. coli wildtype 23S rRNA of SEQ ID NO:1 (RNA sequence of NCBI Reference Sequence: NC_000913.3, GenBank Gene Accession Number 948473), or the corresponding nucleotides of the 23S mutant 040329. Although the nucleotide positions herein are generally provided with reference to SEQ ID NO:1 (provided below) it will be appreciated that in addition to the exemplary reference sequences provided below, the corresponding positions can be identified in other reference sequences using sequence alignment and other such techniques that are well known in the art.

The mutation(s) can be substitutions, insertions, or deletions. Insertions include 5' and/or 3' fusions as well as intrasequence insertions of single or multiple nucleotides. Deletions can also be from the 5' end, the 3' end, intrasequence deletions, or a combination thereof. In preferred embodiments, any 1, 2, 3, 4, 5, 6, 7, 8, 9, or 10 nucleotides at positions 2496-2507, or more preferably any 1, 2, 3, 4, 5, or 6 nucleotides at positions 2502-2507 are mutated relative to E. coli wildtype 23S rRNA; any 1, 2, 3, 4, 5, 6, or 7 nucleotides at positions 2057-2063 are mutated relative to E. coli wildtype 23S rRNA; or a combination thereof. The engineered rRNA does not have 100% sequence identity to variant 040329 (Dedkova, et al., Biochemistry, 51(1):401-15 (2012)). For example, in some embodiments, the engineered rRNA does not have 100% sequence identity to the six nucleotide sequence of variant 040329 corresponding to 2502-2507 of wildtype (SEQ ID NO:1).

In preferred embodiments, the engineered 23S rRNA includes the sequence UGACUU at positions 2502-2507 in place of GAUGUC (of wildtype). In some embodiments, the engineered 23S rRNA also includes the sequence AGCGUGA from positions 2057-2063. The remaining 23S rRNA sequence can be that of wildtype, or a known variant, including, but not limited to, 040329. In some embodiments, the engineered 23S rRNA includes additional mutations relative to wildtype or a known variant such as 040329. For example, in some embodiments, the engineered 23S rRNA includes UGACUU at positions 2502-2507, optionally includes the sequence AGCGUGA from positions 2057-2063, and has one or more additional mutations relative to E. coli wildtype 23S rRNA or a known variant such as 040329.

The engineered 23S rRNA can include a peptidyl transferase center (PTC) corresponding to the wildtype E. coli 23S rRNA or 040329 peptidyl transferase center, but wherein the sequence corresponding to positions 2502-2507 of the full-length wildtype rRNA or 040329 is replaced with UGACUU and optionally wherein the sequence from 2057-2063 of the full-length wildtype rRNA or 040329 is AGCGUGA. The PTC is a 3-dimensional region and not a primary sequence of linear bases.

The engineered 23S rRNA can include a domain V corresponding to the wildtype E. coli 23S rRNA or 040329 peptidyl transferase center, but wherein the sequence corresponding to positions 2502-2507 of the full-length wildtype rRNA or 040329 is replaced with UGACUU and optionally wherein the sequence from 2057-2063 of the full-length wildtype rRNA or 040329 is AGCGUGA. The highly conserved central loop of domain V of 23S RNA (nucleotides 2042 to 2628; Escherichia coli numbering GenBank accession number AF053966, below) is involved in the peptidyl transferase center (Tsiodras, et al., *J Clin Microbiol.*, 38(11): 3991-3993 (2000)).

The 23S rRNA can have, for example, at least 50%, 60%, 70%, 75%, 80%, 85%, 90%, 95%, 96%, 97%, 98%, or 99% sequence identity with *E. coli* wildtype 23S rRNA (e.g., SEQ ID NO:1 or 2) or a known variant such as 040329 (SEQ ID NO:3).

Various types of mutagenesis can be used to modify a nucleic acid. They include, but are not limited to, site-directed, random point mutagenesis, homologous recombination (DNA shuffling), mutagenesis using uracil containing templates, oligonucleotide-directed mutagenesis, phosphorothioate-modified DNA mutagenesis, and mutagenesis using methods such as gapped duplex DNA. Additional suitable methods include point mismatch repair, mutagenesis using repair-deficient host strains, restriction-selection and restriction-purification, deletion mutagenesis, mutagenesis by total gene synthesis and double-strand break repair. Exemplary methods of introducing diversity randomized using dsDNA fragments (gBlocks) are discussed in the Examples below.

1. Exemplary Reference Sequences

The exemplary reference and engineered 23S rRNA sequences are provided as "RNA" sequences, however, in each case the corresponding DNA sequence encoding the rRNA sequence (e.g., wherein the "U" is replaced with a "T") is also explicitly disclosed.

For example, an *E. coli* wildtype 23S rRNA can have the sequence:

```
                                           (SEQ ID NO: 1)
GGUUAAGCGACUAAGCGUACACGGUGGAUGCCCUGGCAGUCA

GAGGCGAUGAAGGACGUGCUAAUCUGCGAUAAGCGUCGGUAA

GGUGAUAUGAACCGUUAUAACCGGCGAUUUCCGAAUGGGGAA

ACCCAGUGUGUUUCGACACACUAUCAUUAACUGAAUCCAUAG

GUUAAUGAGGCGAACCGGGGGAACUGAAACAUCUAAGUACCC

CGAGGAAAGAAAUCAACCGAGAUUCCCCCAGUAGCGGCGAG

CGAACGGGGAGCAGCCCAGAGCCUGAAUCAGUGUGUGUGUUA

GUGGAAGCGUCUGGAAAGGCGCGCGAUACAGGGUGACAGCCC

CGUACACAAAAUGCACAUGCUGUGAGCUCGAUGAGUAGGGC

GGGACACGUGGUAUCCUGUCUGAAUAUGGGGGGACCAUCCUC

CAAGGCUAAAUACUCCUGACUGACCGAUAGUGAACCAGUACC

GUGAGGGAAAGGCGAAAAGAACCCCGGCGAGGGGAGUGAAAA

AGAACCUGAAACCGUGUACGUACAAGCAGUGGGAGCACGCUU

AGGCGUGUGACUGCGUACCUUUUGUAUAAUGGGUCAGCGACU

UAUAUUCUGUAGCAAGGUUAACCGAAUAGGGGAGCCGAAGGG

AAACCGAGUCUUAACUGGGCGUUAAGUUGCAGGGUAUAGACC

CGAAACCCGGUGAUCUAGCCAUGGGCAGGUUGAAGGUUGGGU

AACACUAACUGGAGGACCGAACCGACUAAUGUUGAAAAAUUA

GCGGAUGACUUGUGGCUGGGGGUGAAAGGCCAAUCAAACCGG

GAGAUAGCUGGUUCUCCCCGAAAGCUAUUUAGGUAGCGCCUC

GUGAAUUCAUCUCCGGGGGUAGAGCACUGUUUCGGCAAGGGG

GUCAUCCCGACUUACCAACCCGAUGCAAACUGCGAAUACCGGA

GAAUGUUAUCACGGGAGACACACGGCGGGUGCUAACGUCCGU

CGUGAAGAGGGAAACAACCCAGACCGCCAGCUAAGGUCCCAA

AGUCAUGGUUAAGUGGGAAACGAUGUGGGAAGGCCCAGACAG

CCAGGAUGUUGGCUUAGAAGCAGCCAUCAUUUAAAGAAAGCG

UAAUAGCUCACUGGUCGAGUCGGCCUGCGCGGAAGAUGUAAC

GGGGCUAAACCAUGCACCGAAGCUGCGGCAGCGACGCUUAUG

CGUUGUUGGGUAGGGGAGCGUUCUGUAAGCCUGCGAAGGUGU

GCUGUGAGGCAUGCUGGAGGUAUCAGAAGUGCGAAUGCUGA

CAUAAGUAACGAUAAAGCGGGUGAAAAGCCCGCUCGCCGGAA

GACCAAGGGUUCCUGUCCAACGUUAAUCGGGGCAGGGUGAGU

CGACCCCUAAGGCGAGGCCGAAAGGCGUAGUCGAUGGGAAAC

AGGUUAAUAUUCCUGUACUUGGUGUUACUGCGAAGGGGGGAC

GGAGAAGGCUAUGUUGGCCGGGCGACGGUUGUCCCGGUUUAA

GCGUGUAGGCUGGUUUUCCAGGCAAAUCCGGAAAAUCAAGGC

UGAGGCGUGAUGACGAGGCACUACGGUGCUGAAGCAACAAAU

GCCCUGCUUCCAGGAAAAGCCUCUAAGCAUCAGGUAACAUCA

AAUCGUACCCCAAACCGACACAGGUGGUCAGGUAGAGAAUAC

CAAGGCGCUUGAGAGAACUCGGGUGAAGGAACUAGGCAAAAU

GGUGCCGUAACUUCGGGAGAAGGCACGCUGAUAUGUAGGUGA

GGUCCCUCGCGGAUGGAGCUGAAAUCAGUCGAAGAUACCAGC

UGGCUGCAACUGUUUAUUAAAAACACAGCACUGUGCAAACAC

GAAAGUGGACGUAUACGGUGUGACGCCUGCCCGGUGCCGGAA

GGUUAAUUGAUGGGGUUAGCGCAAGCGAAGCUCUUGAUCGAA

GCCCCGGUAAACGGCGGCCGUAACUAHAACGGUCCUAAGGUA

GCGAAAUUCCUUGUCGGGUAAGUUCCGACCUGCACGAAUGGC

GUAAUGAUGGCCAGGCUGUCUCCACCCGAGACUCAGUGAAAU

UGAACUCGCUGUGAAGAUGCAGUGUACCCGCGGCAAGACGGA

AAGACCCCGUGAACCUUUACUAUAGCUUGACACUGAACAUUG

AGCCUUGAUGUGUAGGAUAGGUGGGAGGCUUUGAAGUGUGGA

CGCCAGUCUGCAUGGAGCCGACCUUGAAAUACCACCCUUUAAU

GUUUGAUGUUCUAACGUUGACCCGUAAUCCGGGUUGCGGACA

GUGUCUGGUGGGUAGUUUGACUGGGGCGGUCUCCUCCUAAAG

AGUAACGGAGGAGCACGAAGGUUGGCUAAUCCUGGUCGGACA

UCAGGAGGUUAGUGCAAUGGCAUAAGCCAGCUUGACUGCGAG

CGUGACGCGCGAGCAGGUGCGAAAGCAGGUCAUAGUGAUCC

GGUGGUUCUGAAUGGAAGGGCCAUCGCUCAACGGAUAAAAGG

UACUCCGGGGAUAACAGGCUGAUACCGCCCAAGAGUUCAUAU

CGACGGCGGUGUUUGGCACCUCGAUGUCGGCUCAUCACAUC
```

```
CUGGGGCUGAAGUAGGUCCCAAGGGUAUGGCUGUUCGCCAUU

UAAAGUGGUACGCGAGCUGGGUUUAGAACGUCGUGAGACAGU

UCGGUCCCUAUCUGCCGUGGGCGCUGGAGAACUGAGGGGGGC

UGCUCCUAGUACGAGAGGACCGGAGUGGACGCAUCACUGGUG

UUCGGGUUGUCAUGCCAAUGGCACUGCCCGGUAGCUAAAUGC

GGAAGAGAUAAGUGCUGAAAGCAUCUAAGCACGAAACUUGCC

CCGAGAUGAGUUCUCCCUGACCCUUUAAGGGUCCUGAAGGAA

CGUUGAAGACGACGACGUUGAUAGGCCGGGUGUGUAAGCGCA

GCGAUGCGUUGAGCUAACCGGUACUAAUGAACCGUGAGGCUU

AACCUU
```

(Genomic sequence at NCBI Reference Sequence: NC_000913.3), or a functional fragment thereof. Positions 2057-2063 and 2502-2507, referenced extensively herein, are bolded and underlined.

An alternative *E. coli* wildtype 23S rRNA can have the sequence:

```
                                    (SEQ ID NO: 2)
GGUUAAGCGACUAAGCGUACACGGUGGAUGCCCUGGCAGUCA

GAGGCGAUGAAGGACGUGCUAAUCUGCGAUAAGCGUCGGUAA

GGUGAUAUGAACCGUUAUAACCGGCGAUUUCCGAAUGGGGAA

ACCCAGUGUGUUUCGACACACUAUCAUUAACUGAAUCCAUAG

GUUAAUGAGGCGAACCGGGGGAACUGAAACAUCUAAGUACCC

CGAGGAAAGAAAUCAACCGAGAUUCCCCCAGUAGCGGCGAG

CGAACGGGGAGCAGCCCAGAGCCUGAAUCAGUGUGUGUGUUA

GUGGAAGCGUCUGGAAAGGCGCGCGAUACAGGGUGACAGCCC

CGUACACAAAAAUGCACAUGCUGUGAGCUCGAUGAGUAGGGC

GGGACACGUGGUAUCCUGUCUGAAUAUGGGGGGACCAUCCUC

CAAGGCUAAAUACUCCUGACUGACCGAUAGUGAACCAGUACC

GUGAGGGAAAGGCGAAAAGAACCCCGGCGAGGGGAGUGAAAA

AGAACCUGAAACCGUGUACGUACAAGCAGUGGGAGCACGCUU

AGGCGUGUGACUGCGUACCUUUUGUAUAAUGGGUCAGCGACU

UAUAUUCUGUAGCAAGGUUAACCGAAUAGGGGAGCCGAAGGG

AAACCGAGUCUUAACUGGGCGUUAAGUUGCAGGGUAUAGACC

CGAAACCCGGUGAUCUAGCCAUGGGCAGGUUGAAGGUUGGGU

AACACUAACUGGAGGACCGAACCGACUAAUGUUGAAAAAUUA

GCGGAUGACUUGUGGCUGGGGGUGAAAGGCCAAUCAAACCGG

GAGAUAGCUGGUUCUCCCCGAAAGCUAUUUAGGUAGCGCCUC

GUGAAUUCAUCUCCGGGGGUAGAGCACUGUUUCGGCAAGGGG

GUCAUCCCGACUUACCAACCCGAUGCAAACUGCGAAUACCGGA

GAAUGUUAUCACGGGAGACACACGGCGGGUGCUAACGUCCGU

CGUGAAGAGGGAAACAACCCAGACCGCCAGCUAAGGUCCCAA

AGUCAUGGUUAAGUGGGAAACGAUGUGGGAAGGCCCAGACAG
```

```
CCAGGAUGUUGGCUUAGAAGCAGCCAUCAUUUAAAGAAAGCG

UAAUAGCUCACUGGUCGAGUCGGCCUGCGCGGAAGAUGUAAC

GGGGCUAAACCAUGCACCGAAGCUGCGGCAGCGACACUAUGU

GUUGUUGGGUAGGGGAGCGUUCUGUAAGCCUGUGAAGGUGUG

CUGUGAGGCAUGCUGGAGGUAUCAGAAGUGCGAAUGCUGACA

UAAGUAACGAUAAAGCGGGUGAAAAGCCCGCUCGCCGGAAGA

CCAAGGGUUCCUGUCCAACGUUAAUCGGGGCAGGGUGAGUCG

ACCCCUAAGGCGAGGCCGAAAGGCGUAGUCGAUGGGAAACAG

GUUAAUAUUCCUGUACUUGGUGUUACUGCGAAGGGGGGACGG

AGAAGGCUAUGUUGGCCGGGCGACGGUUGUCCCGGUUUAAGC

GUGUAGGCUGGUUUUCCAGGCAAAUCCGGAAAAUCAAGGCUG

AGGCGUGAUGACGAGGCACUACGGUGCUGAAGCAACAAAUGC

CCUGCUUCCAGGAAAAGCCUCUAAGAAUCAGGUAACAUCAAA

UCGUACCCCAAACCGACACAGGUGGUCAGGUAGAGAAUACCA

AGGCGCUUGAGAGAACUCGGGUGAAGGAACUAGGCAAAAUGG

UGCCGUAACUUCGGGAGAAGGCACGCUGAUAUGUAGGUGAAG

UCCCUCGCGGAUGGAGCUGAAAUCAGUCGAAGAUACCAGCUG

GCUGCAACUGUUUAUUAAAAACACAGCACUGUGCAAACACGA

AAGUGGACGUAUACGGUGUGACGCCUGCCCGGUGCCGGAAGG

UUAAUUGAUGGGGUUAGCGCAAGCGAAGCUCUUGAUCGAAGC

CCCGGUAAACGGCGGCCGUAACUAUAACGGUCCUAAGGUAGC

GAAAUUCCUUGUCGGGUAAGUUCCGACCUGCACGAAUGGCGU

AAUGAUGGCCAGGCUGUCUCCACCCGAGACUCAGUGAAAUUG

AACUCGCUGUGAAGAUGCAGUGUACCCGCGGCAAGACGGAAA

GACCCCGUGAACCUUUACUAUAACUUGACACUGAACAUUGAG

CCUUGAUGUGUAGGAUAGGUGGGAGGCUUAGAAGUGUGGACG

CCAGUCUGCAUGGAGCCGACCUUGAAAUACCACCCUUUAAUG

UUUGAUGUUCUAACGUUGACCCGUAAUCCGGGUUGCGGACAG

UGUCUGGUGGGUAGUUUGACUGGGGCGGUCUCCUCCUAAAGA

GUAACGGAGGAGCACGAAGGUUGGCUAAUCCUGGUCGGACAU

CAGGAGGUUAGUGCAAUGGCAUAAGCCAGCUUGACUGCGAGC

GUGACGGCGCGAGCAGGUGCGAAAGCAGGUCAUAGUGAUCCG

GUGGUUCUGAAUGGAAGGGCCAUCGCUCAACGGAUAAAAGGU

ACUCCGGGAUAACAGGCUGAUACCGCCCAAGAGUUCAUAUC

GACGGCGGUGUUUGGCACCUCGAUGUCGGCUCAUCACAUCCU

GGGGCUGAAGUAGGUCCCAAGGGUAUGGCUGUUCGCCAUUUA

AAGUGGUACGCGAGCUGGGUUUAGAACGUCGUGAGACAGUUC

GGUCCCUAUCUGCCGUGGGCGCUGGAGAACUGAGGGGGGCUG

CUCCUAGUACGAGAGGACCGGAGUGGACGCAUCACUGGUGUU

CGGGUUGUCAUGCCAAUGGCACUGCCCGGUAGCUAAAUGCGG

AAGAGAUAAGUGCUGAAAGCAUCUAAGCACGAAACUUGCCCC
```

-continued
```
GAGAUGAGUUCUCCCUGACCCUUUAAGGGUCCUGAAGGAACG

UUGAAGACGACGACGUUGAUAGGCCGGGUGUGUAAGCGCAGC

GAUGCGUUGAGCUAACCGGUACUAAUGAACCGUGAGGCUUAA

CCUU
```

(Genomic sequence at GenBank: AF053966.1) or a functional fragment thereof. The nucleotide corresponding to positions 2057-2063 and 2502-2507 of SEQ ID NO:1, referenced extensively herein, are bolded and underlined at 2056-2062 and 2501-2506 of SEQ ID NO:2.

The full sequence of mutant 23S rRNA referred to as 040329 is

```
                                     (SEQ ID NO: 3)
AGCGUUCUUUGAAGUGCUCACACAGAUUGUCUGAUGAAAAUGA

GCAGUAAAACCUCUACAGGCUUGUAGCUCAGGUGGUUAGAGCG

CACCCCUGAUAAGGGUGAGGUCGGUGGUUCAAGUCCACUCAGG

CCUACCAAAUUUGCACGGCAAAUUUGAAGAGGUUUUAACUACA

UGUUAUGGGGCUAUAGCUCAGCUGGGAGAGCGCCUGCUUUGCA

CGCAGGAGGUCUGCGGUUCGAUCCCGCAUAGCUCCACCAUCUCU

GUAGUGAUUAAAUAAAAAAAUACUUCAGAGUGUACCUGCAAAGG

UUCACUGCGAAGUUUUGCUCUUUAAAAAAUCUGGAUCAAGCUGA

AAAUUGAAACACUGAACAACGAAAGUUGUUCGUGAGUCUCUCA

AAUUUUCGCAACACGAUGAUGAAUCGAAAGAAACAUCUUCGGG

UUGUGAGGUUAAGCGACUAAGCGUACACGGUGGAUGCCCUGGC

AGUCAGAGGCGAUGAAGGACGUGCUAAUCUGCGAUAAGCGUCG

GUAAGGUGAUAUGAACCGUUAUAACCGGCGAUUUCCGAAUGGG

GAAACCCAGUGUGUUUCGACACACUAUCAUUAACUGAAUCCAU

AGGUUAAUGAGGCGAACCGGGGGAACUGAAACAUCUAAGUACC

CCGAGGAAAAGAAAUCAACCGAGAUUCCCCCAGUAGCGGCGAG

CGAACGGGGAGCAGCCCAGAGCCUGAAUCAGUGUGUGUGUUAG

UGGAAGCGUCUGGAAAGGCGUGCGAUACAGGGUGACAGCCCCG

UACACAAAAAUGCACAUGCUGUGAGCUCGAUGAGUAGGGCGGG

ACACGUGGUAUCCUGUCUGAAUAUGGGGGACCAUCCUCCAAG

GCUAAAUACUCCUGACUGACCGAUAGUGAACCAGUACCGUGAG

GGAAAGGCGAAAAGAACCCCGGCGAGGGGAGUGAAAAAGAACC

UGAAACCGUGUACGUACAAGCAGUGGGAGCACGCUUAGGCGUG

UGACUGCGUACCUUUUGUAUAAUGGGUCAGCGACUUAUAUUCU

GUAGCAAGGUUAACCGAAUAGGGGAGCCGAAGGGAAACCGAGU

CUUAACUGGGCGUUAAGUUGCAGGGUAUAGACCCGAAACCCGG

UGAUCUAGCCAUGGGCAGGUUGAAGGUUGGGUAACACUAACUG

GAGGACCGAACCGACUAAUGUUGAAAAAUUAGCGGAUGACUUG

UGGCUGGGGGUGAAAGGCCAAUCAAACCGGGAGAUAGCUGGUU

CUCCCCGAAAGCUAUUUAGGUAGCGCCUCGUGAAUUCAUCUCCG

GGGGUAGAGCACUGUUUCGGCAAGGGGGUCAUCCCGACUUACC

AACCCGAUGCAAACUGCGAAUACCGGAGAAUGUUAUCACGGGA

GACACACGGCGGGUGCUAACGUCCGUCGUGAAGAGGGAAACAA

CCCAGACCGCCAGCUAAGGUCCCAAAGUCAUGGUUAAGUGGGA

AACGAUGUGGGAAGGCCCAGACAGCCAGGAUGUUGGCUUUGAA

GCAGCCAUCAUUUAAAGAAAGCGUAAUAGCUCACUGGUCGAGU

CGGCCUGCGCGGAAGAUGUAACGGGGCUAAACCAUGCACCGAA

GCUGCGGCAGCGACACUAUGUGUUGUUGGGUAGGGGAGCGUUC

UGUAAGCCUGUGAAGGUGUGCUGUGAGGCAUGCUGGAGGUAUC

AGAAGUGCGAAUGCUGACAUAAGUAACGAUAAAGCGGGUGAAA

AGCCCGCUCGCCGGAAGACCAAGGGUUCCUGUCCAACGUUAAUC

GGGGCAGGGUGAGUCGACCCCUAAGGCGAGGCCGAAAGGCGUA

GUCGAUGGGAAACAGGUUAAUAUUCCUGUACUUGGUGUUACUG

CGAAGGGGGACGGAGAAGGCUAUGUUGGCCGGGCGACGGUUG

UCCCGGUUUAAGCGUGUAGGCUGGUUUUCCAGGCAAAUCCGGA

AAAUCAAGGCUGAGGCGUGAUGACGAGGCACUACGGUGCUGAA

GCAACAAAUGCCCUGCUUCCAGGAAAAGCCUCUAAGCAUCAGG

UAACAUCAAAUCGUACCCCAAACCGACACAGGUGGUCAGGUAG

AGAAUACCAAGGCGCUUGAGAGAACUCGGGUGAAGGAACUAGG

CAAAAUGGUGCCGUAACUUCGGGAGAAGGCACGCUGAUAUGUA

GGUGAAGCGACUUGCUCGUGGAGCUGAAAUCAGUCGAAGAUAC

CAGCUGGCUGCAACUGUUUAUUAAAAACACAGCACUGUGCAAA

CACGAAAGUGGACGUAUACGGUGUGACGCCUGCCCGGUGCCGG

AAGGUUAAUUGAUGGGGUUAGCCGCAAGGCGAAGCUCUUGAUC

GAAGCCCCGGUAAACGGCGGCCGUAACUAUAACGGUCCUAAGG

UAGCGAAAUUCCUUGUCGGGUAAGUUCCGACCUGCACGAAUGG

CGUAAUGAUGGCCAGGCUGUCUCCACCCGAGACUCAGUGAAAU

UGAACUCGCUGUGAAGAUGCAGUGUACCCGCGGCAAGACGAGC

GUGACCCGUGAACCUUUACUAUAGCUUGACACUGAACAUUGAG

CCUUGAUGUGUAGGAUAGGUGGGAGGCUUUGAAGUGUGGACGC

CAGUCUGCAUGGAGCCGACCUUGAAAUACCACCCUUUAAUGUU

UGAUGUUCUAACGUUGACCCGUAAUCCGGGUUGCGACAGUGU

CUGGUGGGUAGUUUGACUGGGGCGGUCUCCUCCUAAAGAGUAA

CGGAGGAGCACGAAGGUUGGCUAAUCCUGGUCGGACAUCAGGA

GGUUAGUGCAAUGGCAUAAGCCAGCUUGACUGCGAGCGUGACG

GCGCGAGCAGGUGCGAAAGCAGGUCAUAGUGAUCCGGUGGUUC

UGAAUGGAAGGGCCAUCGCUCAACGGAUAAAAGGUACUCCGGG

GAUAACAGGCUGAUACCGCCCAAGAGUUCAUAUCGACGGCGGU

GUUUGGCACCUCUGGCAGGGCUCAUCACAUCCUGGGGCUGAAG

UAGGUCCCAAGGGUAUGGCUGUUCGCCAUUUAAAGUGGUACGC

GAGCUGGGUUUAGAACGUCGUGAGACAGUUCGGUCCCUAUCUG
```

```
CCGUGGGCGCUGGAGAACUGAGGGGGGCUGCUCCUAGUACGAG

AGGACCGGAGUGGACGCAUCACUGGUGUUCGGGUUGUCAUGCC

AAUGGCACUGCCCGGUAGCUAAAUGCGGAAGAGAUAAGUGCUG

AAAGCAUCUAAGCACGAAACUUGCCCCGAGAUGAGUUCUCCCU

GACUCCUUGAGAGUCCUGAAGGAACGUUGAAGACGACGACGUU

GAUAGGCCGGGUGUGUAAGCGCAGCGAUGCGUUGAGCUAACCG

GUACUAAUGAACCGUGAGGCUUAACCUUACAACGCCGAAGGUG

UUUUGGCGAUUGAGAGAAGAUUUUCAGCCUGAUACAGAUUAA

AUCAGAACGCAGAAGCGGUCUGAUAAAACAGAAUUUGCCUGGC

GGCAGUAGCGCGGUGGUCCCACCUGACCCCAUGCCGAACUCAGA

AGUGAAACGCCGUAGCGCCGAUGGUAGUGUGGGGUCUCCUCAU

GCGAGAGUAGGGAACUGCCAGGCAUCAAAUAAAACGAAAGGCU

CAGUCGGAAGACUGGGCCUUUCGUUUUAUCUGUUGUUUGUCGG

UGAACGCUCUCCUGAGUAGGACAAAUCCGCCGGGAGCGGAUUU

GAACGUUGCGAAGCAACGGCCCGAGGGUGGCGGGCAGGACGC

CCGCCAUAAACUGCCAGGCAUCAAAUUAAGCAGAAGGCCAUCCU

GACGGA

-continued

UAGCGAAAUUCCUUGUCGGGUAAGUUCCGACCUGCACGAAUGG

CGUAAUGAUGGCCAGGCUGUCUCCACCCGAGACUCAGUGAAAU

UGAACUCGCUGUGAAGAUGCAGUGUACCCGCGGCAAGACGAGC

GUGACCCGUGAACCUUUACUAUAGCUUGACACUGAACAUUGAG

CCUUGAUGUGUAGGAUAGGUGGGAGGCUUUGAAGUGUGGACGC

CAGUCUGCAUGGAGCCGACCUUGAAAUACCACCCUUUAAUGUU

UGAUGUUCUAACGUUGACCCGUAAUCCGGGUUGCGGACAGUGU

CUGGUGGGUAGUUUGACUGGGGCGGUCUCCUCCUAAAGAGUAA

CGGAGGAGCACGAAGGUUGGCUAAUCCUGGUCGGACAUCAGGA

GGUUAGUGCAAUGGCAUAAGCCAGCUUGACUGCGAGCGUGACG

GCGCGAGCAGGUGCGAAAGCAGGUCAUAGUGAUCCGGUGGUUC

UGAAUGGAAGGGCCAUCGCUCAACGGAUAAAAGGUACUCCGGG

GAUAACAGGCUGAUACCGCCCAAGAGUUCAUAUCGACGGCGGU

GUUUGGCACCUCUGACUUGGCUCAUCACAUCCUGGGGCUGAAG

UAGGUCCCAAGGGUAUGGCUGUUCGCCAUUUAAAGUGGUACGC

GAGCUGGGUUUAGAACGUCGUGAGACAGUUCGGUCCCUAUCUG

CCGUGGGCGCUGGAGAACUGAGGGGGGCUGCUCCUAGUACGAG

AGGACCGGAGUGGACGCAUCACUGGUGUUCGGGUUGUCAUGCC

AAUGGCACUGCCCGGUAGCUAAAUGCGGAAGAGAUAAGUGCUG

AAAGCAUCUAAGCACGAAACUUGCCCCGAGAUGAGUUCUCCCU

GACUCCUUGAGAGUCCUGAAGGAACGUUGAAGACGACGACGUU

GAUAGGCCGGGUGUGUAAGCGCAGCGAUGCGUUGAGCUAACCG

GUACUAAUGAACCGUGAGGCUUAACCUUACAACGCCGAAGGUG

UUUUGGCGGAUUGAGAGAAGAUUUUCAGCCUGAUACAGAUUAA

AUCAGAACGCAGAAGCGGUCUGAUAAAACAGAAUUUGCCUGGC

GGCAGUAGCGCGGUGGUCCCACCUGACCCCAUGCCGAACUCAGA

AGUGAAACGCCGUAGCGCCGAUGGUAGUGUGGGGUCUCCUCAU

GCGAGAGUAGGGAACUGCCAGGCAUCAAAUAAAACGAAAGGCU

CAGUCGGAAGACUGGGCCUUUCGUUUUAUCUGUUGUUUGUCGG

UGAACGCUCUCCUGAGUAGGACAAAUCCGCCGGGAGCGGAUUU

GAACGUUGCGAAGCAACGGCCCGGAGGGUGGCGGGCAGGACGC

CCGCCAUAAACUGCCAGGCAUCAAAUUAAGCAGAAGGCCAUCCU

GACGGAUGGCCUUUUUGCAUUGGCGCAGAAA, or a functional fragment or variant thereof having at least 50%, 60%, 70%, 75%, 80%, 85%, 90%, 95%, 96%, 97%, 98%, or 99% sequence identity with SEQ ID NO:4, wherein the engineered 23S rRNA is not 100% identical to the 23 rRNA of SEQ ID NO:3 or a wildtype rRNA. The nucleotide corresponding to positions 2057-2063 and 2502-2507 of SEQ ID NO:1, referenced extensively herein, are bolded and underlined at 2495-2501 and 2940-2945 of SEQ ID NO:4. Preferably, the 23S rRNA includes at least UGACUU (nucleotides 2940-2945 of SEQ ID NO:4), and more preferably AGCGUGA (nucleotides 2495-2501 of SEQ ID NO:4). In some embodiments the 23S rRNA includes the entire domain V of SEQ ID NO:4, the PTC of SEQ ID NO:4, or a combination thereof.

B. Isolated Nucleic Acid Molecules

Nucleic acids, including genes, cDNA's, and other sequences encoding engineered 23S rRNA are also disclosed. As used herein, "isolated nucleic acid" refers to a nucleic acid that is separated from other nucleic acid molecules that are present in a genome, including nucleic acids that normally flank one or both sides of the nucleic acid in the genome.

An isolated nucleic acid can be, for example, a DNA molecule or an RNA molecule, provided one of the nucleic acid sequences normally found immediately flanking that DNA molecule in a naturally-occurring genome is removed or absent. Thus, an isolated nucleic acid includes, without limitation, a DNA molecule or RNA molecule that exists as a separate molecule independent of other sequences (e.g., a chemically synthesized nucleic acid, or a cDNA, or RNA, or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule or RNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

Nucleic acids can be in sense or antisense orientation, or can be complementary to a reference sequence, for example, a sequence encoding the disclosed rRNAs. Nucleic acids can be DNA, RNA, nucleic acid analogs, or combinations thereof. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) Antisense Nucleic Acid Drug Dev. 7:187-195; and Hyrup et al. (1996) Bioorgan. Med. Chem. 4:5-23. In addition, the deoxyphosphate backbone can be replaced with, for example, a phosphorothioate or phosphorodithioate backbone, a phosphoroamidite, or an alkyl phosphotriester backbone.

C. Vectors

Vectors encoding engineered rRNA are also provided. Nucleic acids, such as those described above, can be inserted into vectors for expression in cells. The vector can be, for example, an expression vector or a cloning vector.

Nucleic acids in vectors can be operably linked to one or more expression control sequences. Operably linked means the disclosed sequences are incorporated into a genetic construct so that expression control sequences effectively control expression of a sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II).

Although rRNA sequences do not encode a protein, a control sequence can be operably linked to a sequence encoding an rRNA, to control expression of the rRNA in a host cell. See, for example, Ponchon and Dardel, *Nature Methods,* 4(7):571-6 (2007); Masson and Miller, J. H., *Gene,* 47:179-183 (1986); Meinnel, et al., *Nucleic Acids Res.,* 16:8095-6 (1988); Tisne, et al., *RNA,* 6:1403-1412 (2000), which provide methods of recombinant expression of tRNA from vectors. In the Examples below, rRNA was expressed from a pUC18 plasmid. Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells are discussed in more detail below. Suitable vectors, promoters, enhancers, and other expression control sequences are discussed in more detail below.

D. Host cells

Host cells including the nucleic acids disclosed herein are also provided. Nucleic acids encoding engineered rRNAs can be transformed or transfected into the host and expressed extrachomasomally, for example by plasmid(s) or another vector(s) or an episome, or the nucleic acids can be integrated into the host's genome. Likewise additional translation machinery can also be transformed or transfected into the host and expressed extrachomasomally or integrated into the host's genome. Exemplary host cells are discussed in more detail below.

III. Expression and Translation Systems

Expression and translation systems for incorporation of one or more dipeptides, or non-standard-, non-natural-, or non-α-amino acids are provided. Suitable dipeptides, non-standard-, non-natural-, and non-α-amino acids are introduced above. Components of a translation system generally include amino acids, ribosomes, tRNAs, mRNA, and synthetases.

The translation system can include all twenty canonical amino acids and one or more dipeptides, non-standard-, non-natural-, or non-α-amino acids. In some embodiments, the one or more non-standard-, non-natural-, or non-α-amino acids are substituted for a corresponding or related canonical amino acid.

The ribosomes can be wildtype ribosomes and/or preferably include engineered ribosomes such as ribosomes including the disclosed engineered 23S rRNA.

tRNAs can be wildtype, engineered, heterologous, or a combination thereof. The system includes at least one tRNA that can be charged with a dipeptide, non-standard-, non-natural-, or non-α-amino acid, as well as tRNAs that can be charged with canonical amino acids. As discussed in more detail below, in some embodiments, a tRNA is polyspecific and can be charged with either a canonical amino acid or a dipeptide, non-standard-, non-natural-, or non-α-amino acids.

In some embodiments, the anticodon of such a tRNA is modified to pair with a "stop codon" to form a suppressor tRNA. The suppressor tRNA can modulate incorporation of the dipeptide, non-standard-, non-natural-, or non-α-amino acid at any location of interest within an mRNA encoding a peptide of interest, by designing the mRNA sequence to include a "stop codon" at the desired location. Thus naturally-occurring tRNAs, for example from *E. coli*, wherein the anticodon is modified to pair with a stop codon, are specifically disclosed.

Additionally, or alternatively, the codon corresponding to the anticodon of a naturally-occurring or wildtype tRNA that can be charged with a dipeptide, non-standard-, non-natural-, or non-α-amino acid can be used to design the mRNA sequence. For example, the experiments below describes that when a DHFR variant containing a single Phe codon at position 128 and a single S to R mutation at position 126 is expressed in *E. coli* grown in the presence of a $\beta^3$-Phe analog, the $\beta^3$-Phe analog can be incorporated at the Phe codon of the nascent DHFR peptide chain during translation, particularly in *E. coli* expressing the disclosed engineered 23S rRNA. The same principles can be applied to other dipeptides, non-standard-, non-natural-, and non-α-amino acids and mRNAs of interest.

The incorporation of one or more non-standard amino acids can be site specific or non-site specific, depending on the selection of the components of the translation system and the sequence of the mRNA of interest. The non-standard amino acid, for example a corresponding non-α amino acid, can simply replace one or more iterations of the corresponding α-amino acid in a polypeptide sequence that is otherwise the same as a naturally-occurring or known peptide sequence. Non-standard amino acids can also be added as one or more additions or insertions to the N-terminus, C-terminus, or within a naturally-occurring or known polypeptide sequence.

Aminoacyl-tRNA synthetases (AARS) can be wildtype, engineered, heterologous, or a combination thereof. The system includes at least one AARS that can catalyze the esterification of a dipeptide, non-standard-, non-natural-, or non-α-amino acid or its precursor to a compatible cognate tRNA to form an aminoacyl-tRNA, as well as AARSs that can catalyze the esterification of cognate amino acids or their precursor to compatible cognate tRNAs to form aminoacyl-tRNAs. As discussed in more detail below, in some embodiments, the same AARS has both activities. For example, the Examples show that $\beta^3$-amino acids are adequate substrates for several wild type *E. coli* aminoacyl-tRNA synthetases. Exemplary aminoacyl-tRNA synthetases include, but are not limited to, MetRS, PheRS, GluRS, GlyRS, and TyrRS.

In some preferred embodiments, the system includes a PheRS, such as wildtype *E. coli* PheRS. The experiments discussed in more detail below show that phenylalanyl-tRNA synthetase (PheRS), can collaborate with wild type *E. coli* elongation factor Tu (EF-Tu) and ribosomes containing mutant peptidyl transferase centers to efficiently incorporate $\beta^3$-Phe derivatives into full length peptides in vivo. *E. coli* harboring the most active ribosome mutants are robust, with a doubling time only 14% longer than wild type. These results emphasize the tolerance of *E. coli* and its translation machinery to the β-amino acid backbone.

The disclosed systems and methods can utilize orthogonal AARS-tRNA pairs, including those known in the art. For example, Table 1 and the electronic supplementary information provided in Dumas, et al., *Chem. Sci.,* 6:50-69 (2015), provide non-natural amino acids that have been genetically encoded into proteins, the reported mutations in the AARS that enable their binding to the non-natural amino acid, the corresponding tRNA, and a host organism in which the translation system is operational. See also Liu and Schultz, *Annu. Rev. Biochem.,* 79:413-44 (2010) and Davis and Chin, *Nat. Rev. Mol. Cell Biol.*, 13:168-82 (2012) which provide additional examples of AARS-tRNA pairs, and WO 2015/120287 which discloses AARS with improved activity and specificity for the specific non-naturally occurring amino acids.

The AARS and tRNA can be provided separately, or together, for example, as part of a single construct. In a particular embodiment, the AARS-tRNA pair is evolved from a *Methanocaldococcus jannaschii* aminoacyl-tRNA synthetase(s) (AARS)/suppressor tRNA pairs and suitable for use in an *E. coli* host organism. See, for example, Young, *J. Mol. Biol.*, 395(2):361-74 (2010), which describes an OTS including constitutive and inducible promoters driving the transcription of two copies of a *M. jannaschii* AARS gene in combination with a suppressor tRNA(CUA)(opt) in a single-vector construct.

The disclosed compositions can be added to a translation system, in vivo or in vitro, to incorporate a dipeptide, non-standard-, non-natural-, or non-α-amino acid into a protein. In preferred embodiments, a cell-based (in vivo) expression system is used. In these embodiments, nucleic acids encoding one or more of ribosomes, tRNAs, mRNA, and synthetases are delivered to cells under conditions suitable for translation and/or transcription of ribosomes, tRNAs, mRNA, synthetases or a combination thereof. The cells can in some embodiments be prokaryotic, e.g., an *E. coli* cell, or eukaryotic, e.g., a yeast, mammalian, plant, or insect or cells thereof.

In some embodiments, a cell-free (in vitro) expression system is used. The most frequently used cell-free translation systems involve extracts containing all the macromolecular components (70S or 80S ribosomes, tRNAs, aminoacyl-tRNA synthetases, initiation, elongation and termination factors, etc.) required for translation of exogenous RNA. To ensure efficient translation, each extract is supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors ($Mg^{2+}$, $K^+$, etc.).

A. Promoters and Enhancers

Nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Therefore, also disclosed is a polynucleotide encoding one or more of wildtype, engineered, or heterologous ribosomal components including the disclosed rRNAs, tRNAs, mRNA, and synthetases operably linked to an expression control sequence.

Promoters are typically DNA regulatory regions capable of initiating transcription of a gene of interest. Some promoters are "constitutive," and direct transcription in the absence of regulatory influences. Some promoters are "tissue specific," and initiate transcription exclusively or selectively in one or a few tissue types. Some promoters are "inducible," and achieve gene transcription under the influence of an inducer. Induction can occur, e.g., as the result of a physiologic response, a response to outside signals, or as the result of artificial manipulation. Some promoters respond to the presence of tetracycline; "rtTA" is a reverse tetracycline controlled transactivator. Such promoters are well known to those of skill in the art. The promoter can be an endogenous promoter (e.g., the promoter for wildtype *E. coli* 23S rRNA) or a heterologous promoter. Suitable promoters can be obtained from viral genomes (e.g., polyoma, Simian Virus 40 (SV40), adenovirus, retroviruses, hepatitis-B virus, and cytomegalovirus) or heterologous mammalian genes (e.g. beta actin promoter).

Enhancers provide expression specificity in terms of time, location, and level. Unlike promoters, enhancers can function when located at various distances from the transcription site. An enhancer also can be located downstream from the transcription initiation site. This enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 bp in length, and they function in cis. Enhancers function to increase transcription from nearby promoters. Enhancers also often contain response elements that mediate the regulation of transcription. Many enhancer sequences are now known from mammalian genes (globin, elastase, albumin, α-fetoprotein and insulin). However, enhancer from a eukaryotic cell virus are preferably used for general expression. Suitable examples include the SV40 enhancer on the late side of the replication origin, the cytomegalovirus early promoter enhancer, the polyoma enhancer on the late side of the replication origin, and adenovirus enhancers.

A coding sequence is "operably linked" and "under the control" of expression control sequences in a cell when RNA polymerase is able to transcribe the coding sequence into mRNA, which then can be translated into the protein encoded by the coding sequence.

In certain embodiments the promoter and/or enhancer region can act as a constitutive promoter and/or enhancer to maximize expression of the region of the transcription unit to be transcribed. In certain constructs the promoter and/or enhancer region is active in all eukaryotic cell types, even if it is only expressed in a particular type of cell at a particular time. A preferred promoter of this type is the CMV promoter. In other embodiments, the promoter and/or enhancer is tissue or cell specific.

In certain embodiments the promoter and/or enhancer region is inducible. Induction can occur, e.g., as the result of a physiologic response, a response to outside signals, or as the result of artificial manipulation. Such promoters are well known to those of skill in the art. For example, in some embodiments, the promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs.

B. Cell Delivery Systems

There are a number of compositions and methods which can be used to deliver nucleic acids to cells, either in vitro or in vivo. These methods and compositions can largely be broken down into two classes: viral based delivery systems and non-viral based delivery systems. For example, nucleic acids can be delivered through a number of direct delivery systems such as electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are well known in the art and readily adaptable for use with the compositions and methods described herein.

Transfer vectors can be any nucleotide construction used to deliver genetic material into cells. In some embodiments the vectors are derived from either a virus or a retrovirus. Viral vectors include, for example, Adenovirus, Adeno-associated virus, Herpes virus, Vaccinia virus, Polio virus, AIDS virus, neuronal trophic virus, Sindbis and other RNA viruses, including these viruses with the HIV backbone.

Typically, viral vectors contain nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. The necessary functions of the removed early genes are typically supplied by cell lines which have been engineered to express the gene products of the early genes in trans.

Nucleic acids can also be delivered through electroporation, sonoporation, lipofection, or calcium phosphate precipitation. Lipofection involves the use liposomes, including cationic liposomes (e.g., DOTMA, DOPE, DC-cholesterol) and anionic liposomes, to delivery genetic material to a cell. Commercially available liposome preparations include LIPOFECTIN, LIPOFECTAMINE (GIBCO-BRL, Inc., Gaithersburg, Md.), SUPERFECT (Qiagen, Inc. Hilden, Germany), and TRANSFECTAM (Promega Biotec, Inc., Madison, Wis.).

As discussed in more detail below, nucleic acids that are delivered to cells which are to be integrated into the host cell genome, can contain integration sequences.

C. Markers

The vectors used to deliver the disclosed nucleic acids to cells can further include nucleic acid sequence encoding a marker product. This marker product is used to determine if the gene has been delivered to the cell and once delivered is being expressed. In some embodiments the marker is a detectable label. Exemplary labels include the E. coli lacZ gene, which encodes β-galactosidase, and green fluorescent protein (GFP).

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection.

III. Methods

A. Incorporation of Non-Canonical Amino Acids

Methods for incorporating one or more dipeptides, or non-standard-, non-natural-, or non-α-amino acids into polypeptides, proteins and other sequence programmed polymeric materials are disclosed. The methods can be used to insert, for example, one or more iterations of a single dipeptide, non-standard-, non-natural-, or non-α-amino acid, or one or more iterations of two or more different one or more dipeptides, or non-standard-, non-natural-, or non-α-amino acids. The non-standard amino acid or non-standard amino acid(s) are typically selected by the practitioner based on the side chain and the desired properties and/or use of the polypeptide as discussed in more detail below. Proteins containing β3-amino acids have enormous usefulness for biotechnology, as β3-amino acid linkages can exhibit both enhanced protease resistance and uniquely altered immunogenicity (Seebach, et al., *FEBS J.*, 273:5261 (2006). Heck, et al., *Chem. Biodiversity*, 3:1325 (2006), Hook, et al., *Chem. Biodiversity*, 2, 591 (2005), Guichard, *J. Med. Chem.*, 43, 3803 (2000), Reinelt, *Biol. Chem.*, 276:24525 (2011). Webb, et al., *J. Immunol.*, 175:3810 (2005). Cheloha, et al., *ACS Chem. Biol.*, 10, 844 (2015)).

Polypeptides including one or more iterations of one or more different non-standard amino acids made utilizing the disclosed engineered ribosomes are also provided. The polypeptide can have any sequence dictated by the practitioner. As discussed herein, the practitioner can design a heterologous mRNA encoding the polypeptide can designed to encode at least one iterations of a dipeptide, non-standard-, non-natural-, or non-α-amino acid. The polypeptides can be monomeric or polymeric. A monomer is a molecule capable of reacting with identical or different molecules to form a polymer. Therefore, in some embodiments, the heterologous mRNA encodes a single subunit that can be part of a larger homomeric or heteromeric macromolecule. The compositions and methods can be used to produce sequence-defined polymers. In other embodiments, the mRNA encodes two or more subunits, for example, two or more repeats of a monomer. In some embodiments, the mRNA encodes a fusion protein including a sequence having at least one non-standard amino acid fused to a sequence of another protein of interest. Accordingly, the polypeptide including one or more non-standard amino acids can be part of a tag or a domain of a larger multiunit polypeptide. The polypeptide can include both standard and non-standard amino acids. In some embodiments, the biomolecule consists of a run of consecutive non-standard amino acids, (e.g., 2, 3, 4, 5, 6, 7, 8, 9, 10, or more), or consists entirely of non-standard amino acids. All iterations of non-standard amino acids can be the same, or the biomolecule can include combinations of two, three, four, or more non-standard amino acids. For example, the compositions can be used to create higher order combinations of monomers to create block polymers with more diverse chemistries. In some embodiments, the polypeptide has any integer "n" from 1 to 500 of a dipeptide, non-standard-, non-natural-, or non-α-amino acid. In some embodiments, "n" is more than 500. The compositions and methods allow for template-based biosynthesis of polymers of, in principle, any length including multiple instances of nonstandard amino acids.

The method involves the use of ribosomes, tRNAs, synthetases or a combination thereof in the translation process for a target polypeptide from mRNA. At least one of the synthetases can charge a cognate tRNA with a dipeptide, non-standard-, non-natural-, or non-α-amino acid. The resulting aminoacyl-tRNA recognizes at least one codon in the mRNA for the target protein, such as the codon corresponding to the anticodon of the aminoacyl-tRNA (e.g., a stop codon, or a natural or engineered codon to the binds to the aminoacyl-tRNA's anticodon).

The Examples below show that EF-Tu mediates the entry of the aminoacyl-RNA charged with diverse $\beta^3$-amino acids into a free site of the ribosome, hydrolyzes guanosine triphosphate (GTP) into guanosine diphosphate (GDP) and inorganic phosphate, and changes in conformation to dissociate from the tRNA molecule. The dipeptide, non-standard-, non-natural-, or non-α-amino acid-charged tRNA then fully enters the A site, where its amino acid is brought near the P site's polypeptide and the ribosome catalyzes the covalent transfer of the amino acid onto the polypeptide. In some embodiments, the EF-Tu is a wildtype EF-Tu. In some embodiments, the EF-Tu in a variant or mutant, for example, one that has improved binding or enzymatic activity, particularly with respect to aminoacyl-RNA charged with a dipeptide, non-standard-, non-natural-, or non-α-amino acid, or a ribosome that mediates translation thereof. In preferred embodiments, an engineered ribosome, such a ribosome including the disclosed engineered 23S rRNA is utilized to improve the $k_{cat}$, $k_M$ or a combination thereof in one or more catalytic steps (e.g., aminoacylation, etc.) of the translation process that results in incorporation of a or more dipeptides, or non-standard-, non-natural-, or non-α-amino acids into a nascent peptide chain.

1. In Vitro Transcription/Translation

The nucleic acids encoding ribosomes, tRNAs, synthetases or a combination thereof can be synthesized prior to translation of the target protein and used to incorporate dipeptides, non-standard-, non-natural-, or non-α-amino acids into a target protein in a cell-free (in vitro) protein synthesis system.

In vitro protein synthesis systems involve the use crude extracts containing all the macromolecular components (70S or 80S ribosomes, tRNAs, aminoacyl-tRNA synthetases, initiation, elongation and termination factors, etc.) required for translation of exogenous RNA. For example, the tRNAs, aminoacyl-tRNA synthetases, and elongation factors in the crude extract can be supplemented with additional wildtype, mutant, or engineered ribosomes (or a ribosomal rRNA thereof), tRNAs, or synthetases or a combination thereof. To ensure efficient translation, each extract can be supplemented with amino acids, energy sources (ATP, GTP), energy regenerating systems (creatine phosphate and creatine phosphokinase for eukaryotic systems, and phosphoenol pyruvate and pyruvate kinase for the E. coli lysate), and other co-factors (Mg2+, K+, etc.). The extract also typically includes an mRNA encoding the desired peptide, and is supplemented with one or more of the dipeptides, non-standard-, non-natural-, or non-α-amino acids to be incorporated into the peptide.

In vitro protein synthesis does not depend on having a polyadenylated RNA, but if having a poly(A) tail is essential for some other purpose, a vector may be used that has a stretch of about 100 A residues incorporated into the polylinker region. That way, the poly(A) tail is "built in" by the synthetic method. In addition, eukaryotic ribosomes read RNAs that have a 5' methyl guanosine cap more efficiently. RNA caps can be incorporated by initiation of transcription using a capped base analogue, or adding a cap in a separate in vitro reaction post-transcriptionally.

Suitable in vitro transcription/translation systems include, but are not limited to, the rabbit reticulocyte system, the E. coli S-30 transcription-translation system, the wheat germ based translational system. Combined transcription/translation systems are available, in which both phage RNA polymerases (such as T7 or SP6) and eukaryotic ribosomes are present. One example of a kit is the TNT® system from Promega Corporation.

2. In vivo Methods

Translation can also be carried out in vivo. Host cells and organisms can also incorporate one or more dipeptides, non-standard-, non-natural-, or non-α-amino acids into proteins or polypeptides via nucleic acids encoding wildtype, mutant, or engineered ribosomes (or a ribosomal rRNA thereof), tRNAs, or synthetases or a combination thereof. Nucleic acids encoding these components operably linked to one or more expression control sequences are introduced into cells or organisms using a cell delivery system. These cells also contain a gene encoding the target protein operably linked to an expression control sequence.

Suitable organisms include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems.

It will be understood by one of ordinary skill in the art that regardless of the system used (i.e. in vitro or in vivo), expression of genes encoding ribosomes (or a ribosomal rRNA thereof), tRNAs, and synthetases will result in site specific incorporation of the dipeptide, non-standard-, non-natural-, or non-α-amino acid into the target polypeptides or proteins that are translated in the system. Host cells are genetically engineered (e.g., transformed, transduced or transfected) with the vectors encoding ribosomes (or a ribosomal rRNA thereof), tRNAs, synthetases or a combination thereof, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation, infection by viral vectors, high velocity ballistic penetration by small particles with the nucleic acid either within the matrix of small beads or particles, or on the surface. Such vectors can optionally contain one or more promoter.

Kits are commercially available for the purification of plasmids from bacteria, (see, e.g., GFX™ Micro Plasmid Prep Kit from GE Healthcare; Strataprep® Plasmid Miniprep Kit and StrataPrep® EF Plasmid Midiprep Kit from Stratagene; GenElute™ HP Plasmid Midiprep and Maxiprep Kits from Sigma-Aldrich, and, Qiagen plasmid prep kits and QIAfilter™ kits from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems.

Following introduction of an expression vector by electroporation, lipofection, calcium phosphate, or calcium chloride co-precipitation, DEAE dextran, or other suitable transfection method, stable cell lines can be selected (e.g., by metabolic selection, or antibiotic resistance to G418, kanamycin, or hygromycin or by metabolic selection using the Glutamine Synthetase-NS0 system). The transfected cells can be cultured such that the polypeptide of interest is expressed, and the polypeptide can be recovered from, for example, the cell culture supernatant or from lysed cells.

Methods of engineering a microorganism or cell line to incorporate a nucleic acid sequence into its genome are known in the art. Nucleic acids that are delivered to cells which are to be integrated into the host cell genome can contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can become integrated into the host genome. Techniques for integration of genetic material into a host genome are also known and include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

For example, cloning vectors expressing a transposase and containing a nucleic acid sequence of interest between inverted repeats transposable by the transposase can be used to clone the stably insert the gene of interest into a bacterial genome (Barry, *Gene,* 71:75-84 (1980)). Stably insertion can be obtained using elements derived from transposons including, but not limited to Tn7 (Drahos, et al., *Bio/Tech.* 4:439-444 (1986)), Tn9 (Joseph-Liauzun, et al., *Gene,* 85:83-89 (1989)), Tn10 (Way, et al., *Gene,* 32:369-379 (1984)), and Tn5 (Berg, In *Mobile DNA*. (Berg, et al., Ed.), pp. 185-210 and 879-926. Washington, D.C. (1989)). Additional methods for inserting heterologous nucleic acid sequences in *E. coli* and other gram-negative bacteria include use of specialized lambda phage cloning vectors that can exist stably in the lysogenic state (Silhavy, et al., Experiments with gene fusions, Cold Spring Harbor Laboratory, Cold Spring Harbor, N.Y. (1984)), homologous recombination (Raibaud, et al., *Gene,* 29:231-241 (1984)), and transposition (Grinter, et al., *Gene,* 21:133-143 (1983), and Herrero, et al., *J. Bacteriology,* 172(11):6557-6567 (1990)).

Integrative plasmids can be used to incorporate nucleic acid sequences into yeast chromosomes. See for example, Taxis and Knop, *Bio/Tech.,* 40(1):73-78 (2006), and Hoslot and Gaillardin, *Molecular Biology and Genetic Engineering of Yeasts*. CRC Press, Inc. Boca Raton, Fla. (1992). Methods of incorporating nucleic acid sequence into the genomes of mammalian lines are also well known in the art using, for example, engineered retroviruses such lentiviruses.

Prokaryotes useful as host cells include, but are not limited to, gram negative or gram positive organisms such as *E. coli* or *Bacilli*. The *E. coli* strain can be a selA, selB, selC, deletion strain, or combinations thereof. For example, the *E. coli* can be a selA, selB, and selC deletion strain, or a selB and selC deletion strain. Examples of suitable *E. coli* strains include, but are not limited to, MH5 and MH6.

In a prokaryotic host cell, a polypeptide may include an N-terminal methionine residue to facilitate expression of the recombinant polypeptide in the prokaryotic host cell. The N-terminal Met may be cleaved from the expressed recombinant polypeptide. Promoter sequences commonly used for recombinant prokaryotic host cell expression vectors include lactamase and the lactose promoter system.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence are inserted into the pBR322 vector. Other commercially available vectors include, for example, T7 expression vectors from Invitrogen, pET vectors from Novagen and PALTER® vectors and PinPoint® vectors from Promega Corporation.

Yeasts useful as host cells include, but are not limited to, those from the genus *Saccharomyces, Pichia, K. Actinomycetes* and *Kluyveromyces*. Yeast vectors will often contain an origin of replication sequence, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, (1980)) or other glycolytic enzymes (Holland et al., Biochem. 17:4900, (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer et al., Gene, 107:285-195 (1991), in Li, et al., *Lett Appl Microbiol.* 40(5):347-52 (2005), Jansen, et al., *Gene* 344:43-51 (2005) and Daly and Hearn, *J. Mol. Recognit.* 18(2):119-38 (2005). Other suitable promoters and vectors for yeast and yeast transformation protocols are well known in the art.

Mammalian or insect host cell culture systems well known in the art can also be employed to express ribosomes (or a ribosomal rRNA thereof), tRNAs, synthetases or a combination thereof for producing proteins or polypeptides containing one or more dipeptides, non-standard-, non-natural-, or non-α-amino acids. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are well known in the art.

The host organism can be a genomically recoded organism "GRO." Typically, the GRO is a bacterial strain, for example, an *E. coli* bacterial strain, wherein a codon has been replaced by a synonymous codon. Because there are 64 possible 3-base codons, but only 20 canonical amino acids (plus stop codons), some amino acids are coded for by 2, 3, 4, or 6 different codons (referred to herein as "synonymous codons"). In a GRO, most or all of the iterations of a particular codon are replaced with a synonymous codon. The precursor strain of the GRO is recoded such that at a least one codon is completely absent from the genome. Removal of a codon from the precursor GRO allows reintroduction of the deleted codon in, for example, a heterologous mRNA of interest. As discussed in more detail below, the reintroduced codon is typically dedicated to a non-standard amino acid, which in the presence of the appropriate translation machinery, can be incorporated in the nascent peptide chain during translation of the mRNA.

Different organisms often show particular preferences for one of the several codons that encode the same amino acid, and some codons are considered rare or infrequent. Preferably, the replaced codon is one that is rare or infrequent in the genome. The replaced codon can be one that codes for an amino acid (i.e., a sense codon) or a translation termination codon (i.e., a stop codon). GRO that are suitable for use as host or parental strains for the disclosed systems and methods are known in the art, or can be constructed using known methods. See, for example, Isaacs, et al., *Science,* 333, 348-53 (2011), Lajoie, et al., *Science* 342, 357-60 (2013), Lajoie, et al., *Science,* 342, 361-363 (2013).

Preferably, the replaced codon is one that codes for a rare stop codon. In a particular embodiment, the GRO is one in which all instances of the UAG (TAG) codon have been removed and replaced by another stop codon (e.g., TAA, TGA), and preferably wherein release factor 1 (RF1; terminates translation at UAG and UAA) has also been deleted, eliminating translational termination at UAG codons (Lajoie, et al., *Science* 342, 357-60 (2013)). In a particular embodiment, the host or precursor GRO is C321.Δ A [321 UAG→UAA conversions and deletion of prfA (encodes RF1)] (genome sequence at GenBank accession CP006698). This GRO allows the reintroduction of UAG codons in a heterologous mRNA, along with orthogonal translation machinery (i.e., aminoacyl-tRNA synthetases (aaRSs) and tRNAs as discussed in more detail below), to permit efficient and site specific incorporation of non-standard amino acids into protein encoded by the recoded gene of interest. That is, UAG has been transformed from a nonsense codon (terminates translation) to a sense codon (incorporates amino acid of choice), provided the appropriate translation machinery is present. UAG is a preferred codon for recoding because it is the rarest codon in *Escherichia coli* MG1655 (321 known instances) and a rich collection of translation machinery capable of incorporating non-standard amino acids has been developed for UAG (Liu and Schultz, *Annu. Rev. Biochem.,* 79:413-44 (2010), discussed in more detail below).

Stop codons include TAG (UAG), TAA (UAA), and TGA (UGA). Although recoding to UAG (TAG) is discussed in more detail above, it will be appreciated that either of the other stop codons (or any sense codon) can be recoded using the same strategy. Accordingly, in some embodiments, a sense codon is reassigned, e.g., AGG or AGA to CGG, CGA, CGC, or CGG (arginine), e.g., as the principles can be extended to any set of synonymous or even non-synonymous codons, that are coding or non-coding. Similarly, the cognate translation machinery can be removed/mutated/ deleted to remove natural codon function (UAG—RF1, UGA—RF2). The orthogonal translation system, particularly the antisense codon of the tRNA, can be designed to match the reassigned codon.

GRO can have two, three, or more codons replaced with a synonymous or non-synonymous codon. Such GRO allow for reintroduction of the two, three, or more deleted codons in one or more recoded genes of interest, each dedicated to a different non-standard amino acid. Such GRO can be used in combination with the appropriate orthogonal translation machinery to produce polypeptides having two, three, or more different non-standard amino acids.

B. Exemplary Applications

Since macromolecules of different chemical composition generally do not form homogeneous mixtures, copolymerization of different monomers into the same polymer chain is the practical analog of alloying in polymer materials science. However, most synthetic routes to copolymers produce significant distributions in both composition and sequence within a single sample. As a result, synthesis methods with the precise sequence and architectural control needed to establish meaningful structure-function relationships have remained firmly out of reach. By providing a means to control sequence and architecture, the disclosed compositions and methods provide a path to polymers with previously unimaginable structures and functions.

Figure 7:
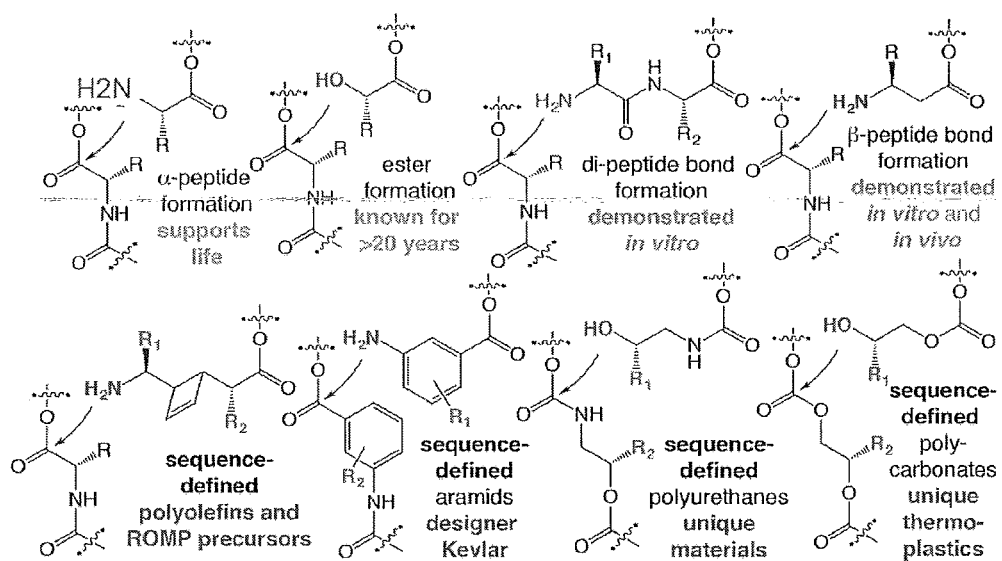
FIG. 7 is an illustration of addition-elimination mechanisms for the synthesis of natural α-peptides as well as polyolefins, aramids, polyurethanes, and polycarbonates.

Amide bond formation by a wildtype ribosome follows a classic pathway. An amine nucleophile appended to a ribosome-bound tRNA attacks a proximal ester carbonyl to generate a tetrahedral intermediate, which then breaks down to product—an α-peptide (FIG. 7). Hydroxyl nucleophiles react analogously to generate esters (Ellman, et al., *Science,* 255, 197-200 (1992), Ohta, et al., *ChemBiochem,* 9:2773-2778 (2008)), and even dipeptides and β-amino acids function as substrates in vitro Dedkova, *Biochemistry,* 51, 401-15 (2012), Maini, et al., *Bioorg Med Chem,* 21, 1088-96 (2013), Maini, et al., *Biochemistry,* 16; 54(23):3694-706 (2015), Maini, et al., *J Am Chem Soc.,* 137(35):11206-9 (2015)), and in vivo as disclosed herein.

Sequence control and local order lead to unique deliverables. Sequence control can be used to implement a local degree of order in the macromolecular material. Local order reflects side chain packing—it is analogous to crystallization if the order persists over a long length scale—and can dramatically affect the function of a polymeric material. High local order produces tough, hard regions and low local order produces malleable, elastic regions. The proportions of these two regions can be altered to finely tune mechanical properties. Exemplary polymers include sequence-defined polyolefins, aramids, polyurethanes, and polycarbonates. For example, in polyolefins such as polyethylene or polypropylene, manipulation of branching and stereoregularity affects the degree of crystallinity and domain structure. In polyurethanes, mixtures of hard and soft segments produce materials with a wide range of properties suitable for vehicle body parts (tough) or seat cushion foam (soft). In another example, aramids are temperature-resistant fibers used by the aerospace industry and by the military for body armor and ballistic composites, and depending on the monomer composition (meta vs. para, or the polyhydroquinone-diimidazopyridine subunit in M5), possess vastly different strengths, heat-resistances, and weights. Lastly, polycarbonates are structurally strong, robust materials that can be optically transparent, with diverse applications in protective, high temperature, electronic, and optical devices.

Peptides and polymers can include, for example, 1,3 diketones, aromatic backbones, polyurethane backbones, etc.

Beyond the production of useful novel polymers, the power of the engineered translation apparatus to accommodate a wide variety of non-biological monomers represents an unprecedented technology for producing polymers with extensive post-translational chemical activity. In particular, the incorporation of ring-opening metathesis polymerization (ROMP) precursors of differing reactivity provides great scope for new materials built from primary sequences.

C. Purifying Proteins Containing Non-Canonical Amino Acids

Proteins or polypeptides containing one or more dipeptides, non-standard-, non-natural-, or non-α-amino acids can be purified, either partially or substantially to homogeneity, according to standard procedures known to and used by those of skill in the art including, but not limited to, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, and gel electrophoresis. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against proteins containing the one or more dipeptides, or non-standard-, non-natural-, or non-α-amino acids are used as purification reagents, e.g., for affinity-based purification of proteins containing the one or more dipeptides, or non-standard-, non-natural-, or non-α-amino acids.

In some embodiments, dipeptide, or non-standard-, non-natural-, or non-α-amino acid-containing polypeptides can be engineered to contain an additional domain containing amino acid sequence that allows the polypeptides to be captured onto an affinity matrix. For example, an Fc-containing polypeptide in a cell culture supernatant or a cytoplasmic extract can be isolated using a protein A column. In addition, a tag such as c-myc, hemagglutinin, polyhistidine, or Flag™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase. Immunoaffinity chromatography also can be used to purify polypeptides. Polypeptides can additionally be engineered to contain a secretory signal (if there is not a secretory signal already present) that causes the protein to be secreted by the cells in which it is produced. The secreted proteins can then conveniently be isolated from the cell media.

Once purified, partially or to homogeneity, as desired, the polypeptides may be used as assay components, therapeutic reagents, immunogens for antibody production, etc. Specific applications include the development of therapeutic antibodies that are more stable and less immunogenic by virtue of selective $\beta^3$-amino acid insertion.

Peptides containing β-amino acids can also assemble into protein-like tertiary and quaternary structures. When composed solely of β-amino acids, the structures formed, defined assemblies of 14-helices called β-peptide bundles, fold cooperatively in water solvent into unique and discrete quaternary assemblies that are highly thermostable, bind complex substrates and metal ion cofactors, and, in certain cases, catalyze chemical reactions (Wang and Schepartz, Chem. Commun., 52:7420-7432 (2016)). Thus, in some embodiments, the peptide or protein prepared using the disclosed compositions and methods is a β-peptide bundle, or includes one or more peptide bundles. Peptide bundles are known in the art and reviewed in Wang and Schepartz, Chem. Commun., 52:7420-7432 (2016), which is specifically incorporated by references in its entirety.

Those of skill in the art will recognize that, after synthesis, expression and/or purification, proteins can possess conformations different from the desired conformations of the relevant polypeptides. For example, polypeptides produced by prokaryotic systems often are optimized by exposure to chaotropic agents to achieve proper folding. During purification from lysates derived from E. coli, the expressed protein is optionally denatured and then renatured. This can be accomplished by solubilizing the proteins in a chaotropic agent such as guanidine HCl.

It is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art. Refolding reagents can be flowed or otherwise moved into contact with the one or more polypeptide or other expression product, or vice-versa.

IV. Kits

Kits for producing polypeptides and/or proteins containing one or more dipeptides, or non-standard-, non-natural-, or non-α-amino acids are also provided. For example, a kit for producing a protein that contains one or more dipeptides, or non-standard-, non-natural-, or non-α-amino acids in a cell is provided, where the kit includes a polynucleotide sequence encoding wildtype, mutant, or engineered ribosomes (or a ribosomal rRNA thereof), tRNAs, or synthetases or a combination thereof. In one embodiment, the kit further includes one or more dipeptides, or non-standard-, non-natural-, or non-α-amino acids. In another embodiment, the kit includes a polynucleotide sequence encoding wildtype, mutant, or engineered ribosomes (or a ribosomal rRNA thereof), tRNAs, or synthetases or a combination thereof, and optionally includes one or more dipeptides, or non-standard-, non-natural-, or non-α-amino acids. Any of the kits can include instructional materials for producing the protein.

The present invention will be further understood by reference to the following non-limiting examples.

EXAMPLES

Czekster, et al., J. Am. Chem. Soc., 2016, 138 (16), pp 5194-5197 (2016), DOI: 10.1021/jacs.6b01023, and 27 pages of supplemental/supporting information associated therewith is specifically incorporated by reference in its entirety.

Example 1 tRNA Synthetases can Utilize β-Amino Acids (Notably β³-Amino Acids) as Substrates Materials and Methods Purchased Materials α-Amino acids, β³-phenylalanine (β³-Phe), β³-tyrosine (β³-Tyr), β³-glycine (β³-Gly) and all other chemicals were purchased from Sigma-Aldrich (St. Louis, Mo.) unless otherwise noted. β³-methionine (β³-Met) and β³-glutamic acid (β³-Glu) were purchased from PepTech Corp. (Burlington, Mass.). [γ-$^{32}$P]-ATP and tetrasodium-[$^{32}$P]-pyrophosphate [$^{32}$P]-NaPPi]) were from Perkin Elmer (Waltham, Mass.). Enzcheck Pyrophosphate assay kit was from Thermo Fisher Scientific. All tRNAs used for experiments in Examples 1 and 3 (except for tRNA$_{Gly}$, whose preparation is described below) were purchased from MP Biomedicals and are "natural", that is, isolated from *E. coli*. Kinetic analysis of TyrRS activity was performed on a Molecular Devices Spectramax M5 Microplate Reader (Sunnyvale, Calif.). All experiments using $^{32}$P were imaged using a Typhoon™ FLA9500 biomolecule imager (GE Healthcare). Bands were quantified using ImageJ, and data was analyzed using Prism 6 for Mac OSX. Oligonucleotides were purchased from Integrated DNA Technologies.

Plasmids

Plasmids encoding *E. coli* MetRS (pQE-60) and *E. coli* PheRS (pQE-31) were provided by Dr. Robert Grodzicki (Steitz laboratory, Yale University), plasmid encoding tRNA-nucleotidyltransferase 1 (pQE30, CCA-adding enzyme) was a gift from Dr. Yuri Polikanov (Steitz laboratory, Yale University). The plasmid encoding *E. coli* GluRS (pET20) was provided by Dr. Noah Reynolds (Soll laboratory, Yale University); those encoding *E. coli* GlyRS (pET21a) and *E. coli* EF-Tu (pPROEx-HTb) were provided by Rachel Fleisher (Cornish laboratory, Columbia University). The plasmid pLK35-rrnb was a gift from Dr. Steven Gregory (Dahlberg laboratory, Brown University) and pET28a-DHFR was a gift from Dr. Shinsuke Sando (University of Tokyo). The plasmid encoding *E. coli* TyrRS (PJExpress411) was purchased from DNA 2.0.

Preparation of tRNA$_{Gly}$

*E. coli* tRNA$_{Gly}$ was prepared by in vitro transcription using T7 RNA polymerase (provided by Dr. Olga Fedorova, Pyle laboratory, Yale University) and the DNA templates and primer sequences shown in Table 1. The DNA template contained a 2'-O-methyl modified nucleoside at the second-to-last position of the template (5' to 3' direction), as indicated on Table 1, to minimize run-off transcription (Kao, et al., *Methods*, 23:201 (2001)). In a typical reaction, the primer (T7pol Sequence) was mixed with template (Gly_t7) in a 1:1 molar ratio (final amount added of DNA template=20 μg dsDNA per 1 mL transcription reaction) heated to 100° C. for 5 min in transcription buffer (22 mM MgCl$_2$, 40 mM Tris-HCl (pH 8.0), 2 mM spermidine, 10 mM DTT, 01% Triton-X) and then slowly cooled at room temperature for 30 min. To this reaction mixture was added an rNTP mix (5 mM ATP, 5 mM CTP, 5 mM UTP and 6 mM GTP), as well as T7 RNA polymerase (final concentration 20,000 U/mL) and water to a final volume of 1 mL. The reaction was allowed to proceed for 16 h at 37° C., at which time the tRNA product was ethanol precipitated and purified using a 6% denaturing (6 M) urea polyacrylamide gel. The gel band was visualized by UV-shadowing, cut from the gel, crushed, and extracted using extraction buffer (40 mM MOPS (pH 6.0), 1 mM EDTA, 400 mM NaCl) with agitation at 4° C. for 16 h.

TABLE 1

DNA fragments used for run-off transcription of *E. coli* tRNA$_{Gly}$. All sequences are written in the 5' to 3' direction. Methylated based are shown as mG. Double stranded region for T7 RNA polymerase binding is shown with underlining.

| | |
|---|---|
| Gly_t7 | TmGG AGC GGG AAA CGA GAC TCG AAC TCG CGA CCC CGA CCT TGG CAA GGT CGT GCT CTA CCA ACT GAG CTA TTC CCG C<u>CT ATA GTG AGT CGT ATT A</u> (SEQ ID NO: 5) |
| T7pol_Sequence | CAT ATG <u>TAA TAC GAC TCA CTA TAG</u> (SEQ ID NO: 6) |

Pre-Treatment of Commercial tRNAs

Commercial tRNAs were resuspended in 100 mM borate buffer (pH 8.0) and incubated at 37° C. for one hour to ensure complete deacylation (Effraim, et al., *Nat Chem Biol*, 5:947 (2009)). Prior to use, each tRNA was ethanol precipitated and buffer exchanged using a micro Bio-Spin 6 column (BioRad) and 100 mM HEPES (pH 8.0) with 100 mM KCl following the procedure specified by the manufacturer.

Expression and Purification of aaRS Enzymes and EF-Tu

Plasmids encoding *E. coli* MetRS (pQE-60), *E. coli* PheRS (pQE-31), *E. coli* GluRS (pET20), *E. coli* GlyRS (pET21a), *E. coli* TyrRS (PJExpress411), and *E. coli* EF-Tu (pPROEx-HTb) were transformed into BL21(DE3) cells (#200131, Agilent). Cultures (50 mL) were grown overnight at 37° C. in the presence of 50 μg/mL carbenicillin, then diluted 100-fold into 2 L LB media. These cultures were grown at 37° C. with shaking (200 rpm) until the optical density at 600 nm (OD$_{600}$) reached 0.6 A.U. Protein expression was then induced by the addition of 1 mM isopropyl β-D-1-thiogalactopyranoside (IPTG, American Bio). The cultures were incubated for an additional 6 h and centrifuged at 4000×g (Beckman Allegra R centrifuge, TS-5.1 rotor) for 15 min. To isolate the desired aaRS enzymes or EF-Tu, each cell pellet was resuspended in 30 mL Ni-NTA lysis/wash buffer (20 mM Tris (pH 7.4), 300 mM NaCl, 10 mM imidazole) supplemented with a single complete EDTA-free protease inhibitor tablet (Roche Applied Science). The resulting suspension was lysed by two passages through a French press at 12000 psi, and purified by Ni-NTA chromatography. Each desired protein was eluted using a series of buffers consisting of lysis buffer supplemented with 50, 100, 150, 200, and 500 mM imidazole. The purity of each fraction was assessed on a 4-20% Coomassie-stained PAGE gel. Fractions whose purity was >95% were pooled, concentrated to 3 mL, loaded on a Superdex 5200 gel filtration column (GE Healthcare) using an AKTA FPLC system (GE Healthcare), and eluted with storage buffer (20 mM Tris (pH 7.4), 50 mM NaCl, 10 mM MgCl$_2$, 7 mM β-mercaptoethanol and 30% glycerol). Fractions containing pure protein were combined, concentrated, divided in aliquots, flash frozen, and stored at −80° C. Protein concentrations were determined by absorbance at 280 nm (Pace, et al., *Prot Sci*, 4:2411 (1995)).

Kinetic Analysis of α- and β-Amino Acid Adenylation i. Adenylation of α- and β-Amino Acids Catalyzed by *E. coli* PheRS, GlyRS, MetRS, and GluRS. Kinetic parameters for adenylation, as catalyzed by MetRS, PheRS, GluRS, and GlyRS, were obtained using a previously reported pyrophosphate exchange assay performed in a 96-well format (FIG.

1F) (Beebe, et al., *Anal Biochem,* 368:111 (2007); Calendar, et al., *Biochemistry,* 5:1681 (1966)). Briefly, assay mixtures (50 μL) assembled at 25° C. contained the requisite α- or β³-amino acid substrate (between 5 μM and 5 mM) in 100 mM HEPES (pH 7.0) containing 100 mM KCl, 15 mM $MgCl_2$, 2 mM ATP, 0.5 mM NaPPi, and 50 μCi [$^{32}$P]-NaPPi). Reactions were initiated upon addition of enzyme (10 nM MetRS, 10 nM PheRS, or 50 nM GlyRS; 100 nM GluRS for reactions with α-Glu or 1.13 μM GluRS for reactions with β³-Glu), incubated for various times (10 sec to 10 min), and halted by adding a 5 μL reaction aliquot to 100 μL quenching solution (10% charcoal, 0.5% HCl). 50 μL of 200 mM NaPPi in 1.5 N HCl was then added to each quenched reaction to decrease nonspecific binding of pyrophosphate to the charcoal. Each quenched reaction was then filtered through Whatman filter paper (number 3), previously washed with washing solution (200 mM NaPPi in 1 N HCl) using a 96-well BIO-DOT® apparatus (BioRad). Each well of the apparatus was then washed four times with 200 μL aliquots of washing solution (by pipetting washing solution up and down at least 10 times per wash) to minimize nonspecific binding of pyrophosphate to charcoal. Each experimental well was paired with an analogous control well (no-enzyme control) that lacked enzyme; a single membrane contained time points for both α- and β³-amino acid substrates and all no-enzyme controls. The membrane was allowed to dry and was protected with a sheet of Microseal B adhesive seals (Biorad) prior to exposure to a BAS Storage Phosphor screen. Screens were imaged on a Typhoon 9500FLA biomolecule imager and the signal intensity of each dot was quantified using ImageJ to determine the relative amount of [$^{32}$P]-ATP formed as a function of time ($C_{time}$). Each raw value were corrected by subtracting the intensity of the dot corresponding to the appropriate no-enzyme control ($C_{blank}$) and the resulting corrected values of $C_{corr}$ (representing the relative amounts of $^{32}$P-ATP formed) were plotted as a function of time to determine values of relative $^{32}$P-ATP formed per minute. Those values were divided by the concentration of enzyme used, and the data was plotted as relative specific activity ($^{32}$P-ATP formed $min^{-1} \times \mu M^{-1}$ enzyme) and fitted using Prism by performing nonlinear regression using the least squares method and Equation 1 to obtain RSA (relative specific activity) and $K_M$ values (Equation 1 and Table 2).

$$v = \frac{RSA * S}{K_M + S} \quad \text{Equation 1}$$

In Equation 1, v is the apparent relative specific activity (relative $^{32}$P-ATP formed per minute) obtained at each substrate concentration divided by the enzyme concentration, RSA is the relative specific activity, S is the concentration of substrate, and $K_M$ is the Michaelis-Menten constant. For GluRS, GlyRS, MetRS, and PheRS, RSA has units of relative $^{32}$P-ATP formed $min^{-1} \times \mu M^{-1}$ enzyme, since there is no direct conversion to $^{32}$P-ATP concentration. $^{32}$P-ATP formed could be quantified if a $^{32}$P-ATP standard curve was run at the same time each experiment was performed (in the same membrane) but because the focus was direct comparison between α and β³-amino acids all amino acid concentrations, times quenched, and negative controls for both substrates in the membrane were included (excluding the $^{32}$P-ATP standard curve).

ii. Adenylation of α- and β-Tyr catalyzed by *E. coli* TyrRS. These reactions were monitored spectrophotometrically in a coupled assay using inorganic pyrophosphatase, 2-amino-6-mercapto-7-methylpurine ribonucleoside (MESG), and purine nucleoside phosphorylase (PNP) to monitor the rate of pyrophosphate release, according to the manufacturer's instructions (Enzcheck Pyrophosphate assay kit, Thermo Fisher Scientific). The assay measures the increase in absorbance at 360 nm due to MESG phosphorolysis, and two molecules of MESG are consumed per pyrophosphate generated. This direct assay could be employed for TyrRS because the rate of ATP hydrolysis (in the absence of amino acid substrate) was insignificant, which was not the case for the other synthetases which therefore required the more laborious pyrophosphate exchange assay described above. Data for TyrRS was fitted using Prism by performing nonlinear regression using the least squares method and Equation 2 to obtain $k_{cat}$ and $K_M$ values. For TyrRS, $k_{cat}$ is the turnover number (units of reciprocal time) since the change in absorbance can be directly correlated to concentration of pyrophosphate formed.

$$v = \frac{k_{cat} * S}{K_M + S} \quad \text{Equation 2}$$

iii. Preparation of $^{32}$P-tRNA substrates for aminoacylation reactions. BL21(DE3) cells were transformed with pQE30, encoding $His_6$-tagged *E. coli* terminal tRNA-nucleotidyl-transferase 1 (CCA-adding enzyme), grown until the $O.D._{600}$ reached a value of 0.6, and then induced with 1 mM IPTG to initiate protein expression. Cells were grown for an additional 16 h at 37° C. after induction, and the cell pellet harvested by centrifugation. The resulting cell pellet was resuspended in Buffer A (50 mM Tris-HCl (pH 8.0@4 degrees), 100 mM KCl, 10 mM $MgCl_2$, and 5 mM 2-mercaptoethanol), and the purified enzyme isolated using Ni-NTA chromatography upon elution with buffer A supplemented with 150 mM and then 400 mM imidazole. Fractions containing enzyme were combined, concentrated to 5 mL, loaded onto a Superdex 75 16/60 column (GE Healthcare), and eluted using buffer A+10% glycerol. The resulting purified fractions were pooled and dialyzed against Buffer C (20 mM Tris-HCl (pH 8.0@4 degrees), 5 mM 2-mercaptoethanol, and 10% glycerol) to remove KCl. The resulting solution was loaded onto a Source 15Q column and eluted with a linear gradient using buffer D, which is buffer C+1 M NaCl. Fractions containing enzyme were dialyzed against 0.1 M glycine buffer (pH 9.0), 10 mM DTT and 40% glycerol and stored at –20° C. tRNA labeling was performed according to Ledoux, et al. (Ledoux, et al., *Methods,* 44:74 (2008)). A typical reaction (100 μL total volume) consisted of 0.1 M glycine buffer (pH 9.0), 10 mM $MgCl_2$, 20 μM tRNA, 0.2 μM CCA-adding enzyme, 50 μM NaPPi, and 60 μCi of γ-[$^{32}$P]-ATP. Reactions were allowed to proceed for 20 min at 37° C. The reaction mixture was then extracted with phenol/chloroform and the tRNA product ethanol precipitated.

iv. Aminoacylation of α- and β³-amino acids. All tRNAs were prepared for aminoacylation by heating $^{32}$P-tRNA (in 100 mM HEPES (pH 7.0)) to 95° C. for 3 min, and adding sufficient aminoacylation buffer (100 mM HEPES (pH 7.0), 100 mM KCl, 15 mM $MgCl_2$) to ensure [$^{32}$P-tRNA]=4 μM. This tRNA mixture was allowed to cool at RT for 30 min. During the cooling process, an amino acid mix was prepared containing α- or β³-amino acid (enzyme concentrations were as follows: TyrRS: 10 nM for α-Tyr, 60 nM for β³-Tyr;

MetRS: 97 nM for α-Met, 97 nM for β³-Met; PheRS: 1.2 µM for α-Phe, 1.2 µM for β³-Phe; GlyRS: 100 nM for α-Gly, 500 nM for β³-Gly; GluRS: 500 nM for α-Glu, 5.01 µM for β³-Glu) in aminoacylation buffer supplemented with 8 mM ATP. Equal volumes of the tRNA and amino acid mix were combined, and enzyme was added to initiate the reaction. The final concentration of tRNA after mixing was 2 µM. Reactions were quenched at various time points by mixing 1 µL of the reaction mixture with 4 µL of P1 (Sigma) or S1 (Invitrogen) nuclease solution (0.5 U/µL final prepared from a 10 U/µL stock solution in 10 mM NaOAc (pH 5.0). PEI cellulose TLC plates were run as previously described (Ledoux, et al., *Methods*, 44:74 (2008)), exposed to a BAS Storage Phosphor Screen, and imaged using a Typhoon FLA9500 biomolecule imager. The intensity of each band was quantified using ImageJ. The sum of the intensities of the bands corresponding to [$^{32}$P]-AMP ($I_{AMP}$) and aminoacyl-[$^{32}$P]-AMP ($I_{AA}$) was set equal to 2 µM, and the concentration of aminoacylated-tRNA at each time point and each enzyme concentration (µM product formed, x) calculated from the equation $x=[(I_{AA} \times 2 \text{ µM})/(I_{AA}+I_{AMP})]$. The increase in aminoacyl-$^{32}$P-AMP over time was divided by the amount of enzyme used, plotted as a function of substrate concentration and fitted to a hyperbolic equation to obtain $k_{cat}$ and $K_M$ values, using Equation 1 and Prism as described for the adenylation reactions. For all aminoacylation reactions, $k_{cat}$ has units of reciprocal time (min$^{-1}$).

v. Deacylation assays. Large scale (200 µL) aminoacylation reactions were initiated using the conditions described above (iv). The reactions were allowed to proceed for 1 h at 37° C., after which each reaction mixture was phenol/chloroform extracted. In each case, the aminoacylated tRNA product was ethanol precipitated, and the buffer was exchanged using a micro Bio-Spin 6 column (BioRad) following the procedure specified by the manufacturer and 100 mM HEPES (pH 8.0) containing 100 mM KCl. The precise extent of aminoacylation was calculated using the procedure described above; the 2 µM concentration corresponds to total aminoacylated tRNA. Assays were performed at 25° C. in a 50 µL reaction with 2 µM [$^{32}$P]-aminoacyl-tRNA in 100 mM HEPES (pH 7.0) containing 100 mM KCl and 15 mM MgCl$_2$. Reactions were initiated by addition of enzyme (enzyme concentrations were as follows: TyrRS: 1 µM; MetRS: 500 nM; PheRS: 500 nM; GlyRS: 2 µM for α-Gly; GluRS: 5.0 µM) and quenched at the indicated times by adding a 1 µL reaction aliquot to 4 µL of P1 (Sigma) or S1 (Invitrogen) nuclease solution (0.5 U/µL final prepared from a 10 U/µL stock solution in 10 mM NaOAc (pH 5.0). PEI cellulose TLC plates were run as previously described (Ledoux, et al., *Methods*, 44:74 (2008)), exposed, imaged, and analyzed as described above.

The decrease in aminoacyl-$^{32}$P-AMP over time was divided by the amount of enzyme used, normalized to the amount of aminoacyl-$^{32}$P-AMP present at time zero, plotted as a function of time, and fitted by linear regression to obtain $k_{rev}$, which is an apparent rate of deacylation with units of reciprocal time (min$^{-1}$).

Results

Figure 1B:
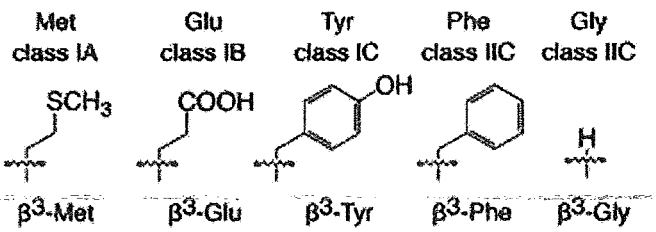
FIG. 1B is an illustration showing the side chains preferred by the five aaRS enzymes evaluated in the Examples.
Figure 1C:
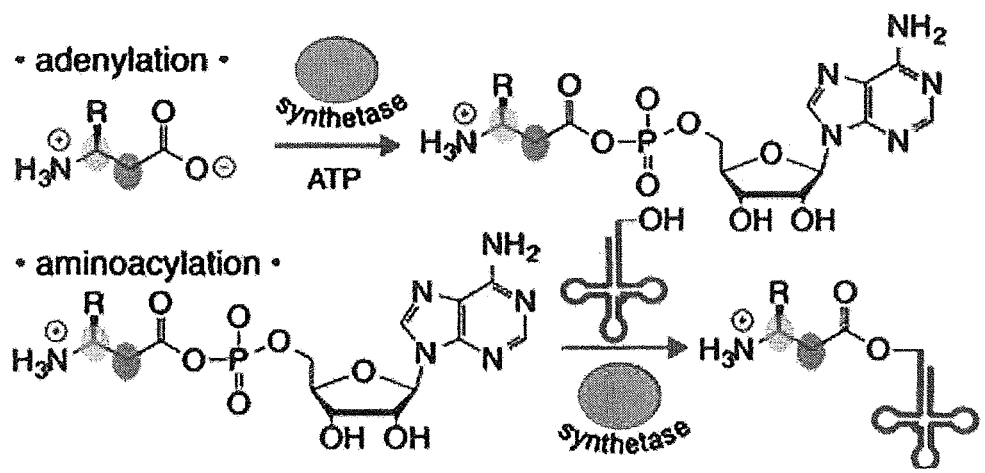
FIG. 1C is a reaction scheme showing that aaRS enzymes catalyze aminoacyl-tRNA formation in two steps in which amino acid activation (adenylation) is followed by acyl transfer (aminoacylation).

Although it is known that a handful of tRNA synthetases can utilize n-amino acids (notably β³-amino acids) as substrates, but no quantitative comparisons to natural substrates were ever performed (Hartman, et al., *Proc Natl Acad Sci USA*, 103:4356 (2006)). Thus, the α/β³-amino acid substrate specificity of five tRNA synthetases were analyzed. Together, the synthetases represent four major sub-classes and accept a diverse set of side-chains: methionyl tRNA synthetase (MetRS, class IA), glutamyl tRNA synthetase (GluRS, class IB), tyrosyl tRNA synthetase (TyrRS, class IC), and phenylalanyl tRNA synthetase and glycyl tRNA synthetase (PheRS and GlyRS, respectively, class IIC) (FIG. 1B). Using purified *E. coli* enzymes, the α-/β³-amino acid specificity of the initial adenylation step, which activates the amino acid substrate, the two-step aminoacylation reaction (activation+acylation), as well as the deacylation reaction, which is also enzyme-catalyzed was evaluated (FIG. 1C). All reactions were monitored using validated methods: adenylation was monitored using a pyrophosphate exchange assay that measures adenylation in reverse through incorporation of [$^{32}$P]-pyrophosphate into ATP (FIG. 1F) (Beebe, et al., *Anal Biochem*, 368:111 (2007); Bruzzese, et al., *Anal Biochem*, 394:24 (2009); Calendar, et al., *Biochemistry*, 5:1681 (1966)). Aminoacylation and deacylation rates were monitored using [α-$^{32}$P]-tRNA substrates and a chromatography assay that quantifies the amount of [α-$^{32}$P]-AMP (from deacylated tRNA) or [α-$^{32}$P]-aminoacyl-AMP (from aminoacyl-tRNA) after P1 nuclease digestion (FIG. 1G) (Ledoux, et al., O. C. *Methods*, 44:74 (2008)).

Figure 1D:
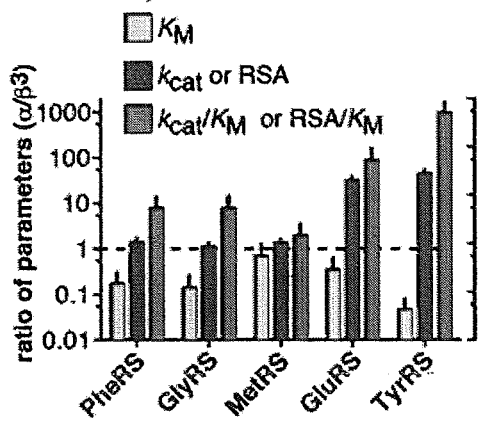
FIGS. 1D and 1E are bar graphs showing kinetic parameters associated with α- and $β^3$-amino acid adenylation (1D), aminoacylation (1E), and deacylation. The y-axis of each plot shows the ratio ($α/β^3$) of the measured kinetic parameters.

All aaRS enzymes evaluated prefer α-amino acid substrates during the adenylation phase of the complete reaction (FIG. 1D). When compared in terms of $k_{cat}/K_M$, GluRS and (especially) TyrRS (both class I) show the greatest selection against β³-amino acid substrates (89- and >900-fold, respectively), with the effects on $k_{cat}$ (32- and 46-fold, respectively) greater than the effects on $K_M$ (2.9- and 21-fold, respectively) (Table 2). In contrast, GlyRS and PheRS (class II) are more tolerant of the expanded β³-amino acid backbone, with both showing only an 8-fold selection ($k_{cat}/K_M$) against β³-amino acid substrates, and roughly equivalent changes in $k_{cat}$ and $K_M$. The most tolerant enzyme evaluated was MetRS (class IA), which displays a modest (2-fold) preference for α-Met over β³-Met during adenylation phase, and very similar values for both $k_{cat}$ and $K_M$.

TABLE 2

Kinetic parameters for α- and β³-amino acid adenylation.

| Amino acid | $k_{cat}$ (min$^{-1}$) or RSA ($^{32}$P-ATP formed min$^{-1}$ enzyme µM$^{-1}$) | Ratio (α-/β-) | $K_M$ (µM) | Ratio (α-/β-) | $k_{cat}/K_M$ (µM$^{-1}$ · min$^{-1}$) | Ratio (α-/β-) |
|---|---|---|---|---|---|---|
| α-Phe | 59.1 ± 7.1 | 1.4 ± 0.3 | 52.8 ± 25.8 | 0.18 ± 0.11 | 1.1 ± 0.5 | 8.06 ± 5.63 |
| β-Phe | 41.6 ± 6.8 | | 299.7 ± 136.6 | | 0.14 ± 0.07 | |
| α-Gly | 166.8 ± 12.8 | 1.14 ± 0.24 | 9.8 ± 3.5 | 0.14 ± 0.11 | 17.1 ± 6.3 | 7.97 ± 6.46 |
| β-Gly | 146.4 ± 29.2 | | 68.4 ± 47.3 | | 2.1 ± 1.5 | |
| α-Met | 430 ± 38 | 1.4 ± 0.2 | 23.4 ± 8.0 | 0.70 ± 0.5 | 18.4 ± 6.5 | 1.98 ± 1.5 |
| β-Met | 310 ± 47 | | 33.4 ± 22 | | 9.3 ± 6.3 | |

TABLE 2-continued

Kinetic parameters for α- and β³-amino acid adenylation.

| Amino acid | $k_{cat}$ (min$^{-1}$) or RSA ($^{32}$P-ATP formed min$^{-1}$ enzyme μM$^{-1}$·) | Ratio (α-/β-) | $K_M$ (μM) | Ratio (α-/β-) | $k_{cat}/K_M$ (μM$^{-1}$ · min$^{-1}$) | Ratio (α-/β-) |
|---|---|---|---|---|---|---|
| α-Glu | 1349 ± 206 | 31.6 ± 6.4 | 76.4 ± 43.0 | 0.35 ± 0.27 | 17.6 ± 10.3 | 89.0 ± 70 |
| β-Glu | 42.7 ± 5.8 | | 215.1 ± 110.1 | | 0.19 ± 0.10 | |
| α-Tyr | 1.22 ± 0.11 | 46.2 ± 7.7 | 21.4 ± 6.9 | 0.047 ± 0.03 | 0.06 ± 0.02 | 972.6 ± 632.0 |
| β-Tyr | 0.027 ± 0.001 | | 450 ± 242.3 | | 0.00006 ± 0.00003 | |

Figure 1E:
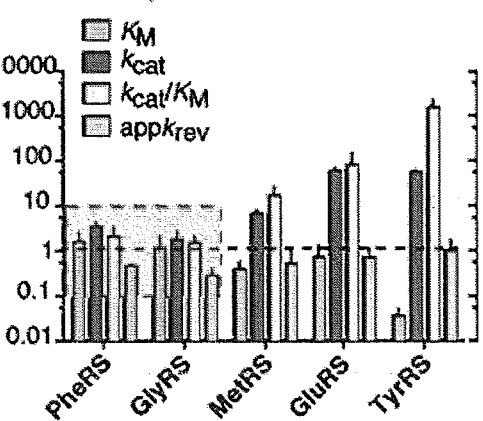
Figures 3A, 3B, 3C:
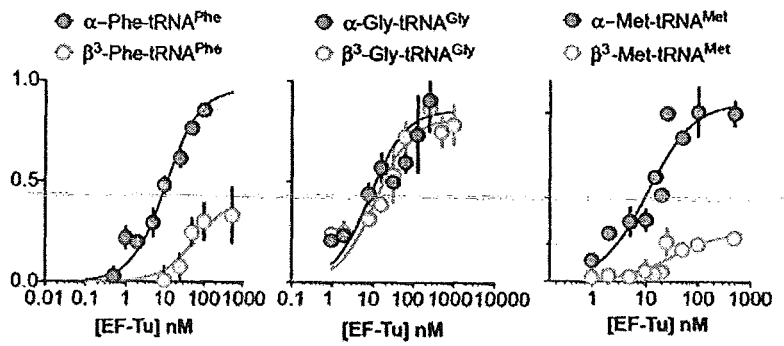
FIGS. 3A-3E are plots showing the fraction of α- (-●-) and β- (-○-) [$^{32}$-P]-aminoacyl-tRNA bound to EF-Tu as a function of [EF-Tu] nM. Fits show binding isotherms for a tight binding ligand exhibiting no cooperativity, from which $K_D$ values were obtained.
Figures 3D, 3E, 3F:
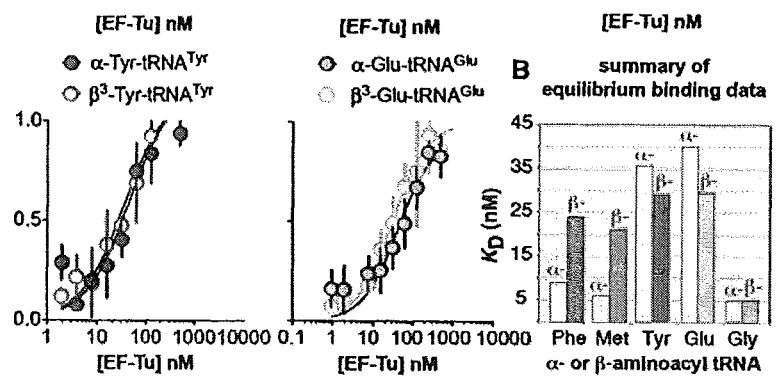
FIG. 3F is a bar graph illustrating how the $K_D$ values determined in (3A-3E) vary as a function of amino acid backbone.

Only slightly different conclusions about α-/β³-amino acid specificity are evident when the complete aminoacylation reaction is considered (FIG. 1E). Indeed, when compared in terms of $k_{cat}/K_M$, GluRS and (especially) TyrRS still show the greatest selection against β³-amino acid substrates (83- and 1500-fold, respectively). For GluRS, the effects on $k_{cat}$ are dominant, whereas for TyrRS the effects on $K_M$ contribute greatly to this difference. MetRS was slightly less tolerant, with a 19-fold preference ($k_{cat}/K_M$) for α-Met over β³-Met. PheRS and GlyRS were again significantly more tolerant of the expanded β³-amino acid backbone, with both showing only a 2-fold selection ($k_{cat}/K_M$) against β³-amino acid substrates, and roughly equivalent changes in $k_{cat}$ and $K_M$ (Table 3). It remains to be established whether β³-amino acid tolerance will be observed for other class II enzymes (such as SerRS and ThrRS (class IIA) or AspRS or LysRS (class IIB)). Nevertheless, the results raised the possibility that GlyRS and PheRS would catalyze the in vivo formation of tRNAs that are misacylated with a β³-Gly or β³-Phe, respectively, or derivatives thereof.

TABLE 5

Summary of equilibrium dissociation constants ($K_D$, nM) for complexes between EF-Tu · GTP and aminoacyl tRNAs.

| side chain | $K_D$ for complex with indicated α-amino acid | $K_D$ for complex with indicated β⁵-amino acid |
|---|---|---|
| Phe | 9.0 ± 3.0 | 24.0 ± 9.8 |
| Met | 6.2 ± 2.0 | 21.5 ± 11.2 |
| Tyr | 36.0 ± 11.0 | 29.1 ± 11.4 |
| Glu | 40.5 ± 14.3 | 29.9 ± 10.7 |
| Gly | 5.0 ± 2.3 | 5.4 ± 2.0 |

TABLE 3

Kinetic parameters for α- and β³-amino acid aminoacylation.

| Amino acid | $k_{cat}$ (min$^{-1}$) | Ratio (α/β) | $K_M$ (μM) | Ratio (α/β) | $k_{cat}/K_M$ (μM$^{-1}$ · min$^{-1}$) | Ratio (α/β) |
|---|---|---|---|---|---|---|
| α-Phe | 0.86 ± 0.11 | 3.7 ± 0.7 | 200.4 ± 78.8 | 1.7 ± 0.9 | 0.0043 ± 0.001 | 2.2 ± 1.3 |
| β-Phe | 0.24 ± 0.03 | | 119.1 ± 51.5 | | 0.002 ± 0.0008 | |
| α-Gly | 5.8 ± 0.5 | 1.9 ± 1.0 | 13.4 ± 4.7 | 1.2 ± 1.00 | 0.43 ± 0.15 | 1.5 ± 0.7 |
| β-Gly | 3.1 ± 0.1 | | 11.1 ± 2.8 | | 0.24 ± 0.07 | |
| α-Met | 1.4 ± 0.1 | 6.8 ± 1.3 | 243.4 ± 55.7 | 0.40 ± 0.18 | 0.006 ± 0.001 | 17.0 ± 8.5 |
| β-Met | 0.21 ± 0.03 | | 608.6 ± 243.4 | | 0.0003 ± 0.0001 | |
| α-Glu | 0.046 ± 0.004 | 61.2 ± 9.1 | 277.1 ± 101.5 | 0.94 ± 0.60 | 0.00016 ± 0.00006 | 82.78 ± 68.2 |
| β-Glu | 0.00075 ± 0.00009 | | 374.8 ± 270.8 | | 0.000002 ± 0.000001 | |
| α-Tyr | 70.5 ± 7.7 | 56.3 ± 6.8 | 12.4 ± 4.8 | 0.036 ± 0.0016 | 5.7 ± 2.3 | 1541.7 ± 724.3 |
| β-Tyr | 1.25 ± 0.7 | | 339.5 ± 80.3 | | 0.0037 ± 0.0008 | |

TABLE 4

Kinetic constants for deacylation.

| Amino acid | $k_{rev}$ (min$^{-1}$) | Ratio (α/β) |
|---|---|---|
| α-Phe | 0.15 ± 0.008 | 0.49 ± 0.05 |
| β-Phe | 0.32 ± 0.03 | |
| α-Gly | 0.21 ± 0.08 | 0.3 ± 0.1 |
| β-Gly | 0.71 ± 0.09 | |
| α-Met | 2.1 ± 1.7 | 0.52 ± 0.49 |
| β-Met | 4.0 ± 1.8 | |
| α-Glu | 0.32 ± 0.14 | 0.73 ± 0.42 |
| β-Glu | 0.43 ± 0.15 | |
| α-Tyr | 1.9 ± 1.3 | 1.01 ± 0.75 |
| β-Tyr | 1.9 ± 0.6 | |

Example 2

Molecular Dynamic Simulations (MD) of TyrRS and PheRS

Materials and Methods

The x-ray crystal structures PDB ID 1X8X (*E. coli* TyrRS (Kobayashi, et al., *Mol Biol,* 346:105 (2005)) and 3PCO (*E. coli* PheRS) (Mermershtain, et al., *Prot Sci,* 20:160 (2011)) were used as inputs for computations that examined differences in the dynamics of α- and β³-amino acid bound aaRS complexes. Hydrogens were added and protonation states were assigned by the Molprobity web tool. The minimum energy conformations of unbound β³-Phe and β³-Tyr were generated using Gaussian 09, Revision D.01 (Frisch, et al., *Gaussian, Inc., Wallingford Conn.* (2009)). Starting positions for bound $\beta^3$-Tyr and $\beta^3$-Phe and ATP were determined by docking the ligand in the binding site using Autodock 4 (Morris, et al., *J Comp Chem,* 19:1639 (1998)). Topology files for the ligands were generated using the SwissParam web tool. The PheRS structure was edited in WinCoot (version .7) to add missing side chains and remove steric clashes that caused the simulation to blow-up. All MD simulations were performed in Gromacs 4.6.5 (Pronk, et al., *E. Bioinform,* 29:845 (2013)) using the CHARMM 27 force field. As there were many steric clashes in the PheRS structure 3PCO (and no other published structures of *E. coli* PheRS are available) the PheRS structure was minimized first in a vacuum before it was minimized in water. Simulations were performed in a cubic box with at least a 0.7 nm gap between the protein and the edge of the box and filled with water. Charges were neutralized using 0.15 M $MgCl_2$. $MgCl_2$ was used to neutralize the charge instead of NaCl so that $Mg^{2+}$ ions would be present to interact with the phosphate groups on ATP. After addition of solvent and ions to the simulation box, the energy of the protein structure was minimized (settings used: define=–DFLEXIBLE, integrator=cg, nsteps=200, constraints=none, emtol=1000.0, nstcgsteep=10, emstep=0.01, nstcomm=1, coulombtype=PME, ns_type=grid, rlist=1.02, rcoulomb=1.02, rvdw=1.4, Tcoupl=no, Pcoupl=no, gen_vel=no, nstxout=0, optimize_fft=yes) and a simulation to relax the solvent was performed (settings used: define=–DPOSRES, integrator=md, nsteps=50000, dt=0.002, constraints=all-bonds, nstcomm=10, ns_type=grid, rlist=1.2, rcoulomb=1.2, rcoulomb-switch=0.9, rvdw=1.0, vdwtype=shift, rvdw-switch=0.9, coulombtype=PME, Tcoupl=v-rescale, tau_t=0.1 0.1, tc-grps=protein non-protein, ref_t=300 300, Pcoupl=no, Pcoupltype=isotropic, tau_p=0.5, compressibility=4.5e-5, ref_p=1.0, gen_vel=yes, gen_temp=300, gen_seed=–1, nstxout=250, nstenergy=100, energygrps=Protein LIG SOL, lincs-iter=2, DispCorr=EnerPres, optimize_fft=yes). Then a 4 ns simulation was run for the $\alpha$-amino acid and $\beta^3$-amino acid bound form of each synthetase (settings used: integrator=md, nsteps=2000000, dt=0.002, constraints=all-bonds, nstcomm=10, ns_type=grid, rlist=1.2, rcoulomb=1.2, rcoulomb-switch=0.9, rvdw=1.0, vdwtype=shift, rvdw-switch=0.9, coulombtype=PME, Tcoupl=v-rescale, tau_t=0.1 0.1, tc-grps=protein non-protein, ref_t=300 300, Pcoupl=parrinello-rahman, Pcoupltype=isotropic, tau_p=0.5, compressibility=4.5e-5, ref_p=1.0, gen_vel=yes, gen_temp=300, gen_seed=–1, nstxout=500, nstenergy=100, energygrps=Protein LIG SOL, lincs-iter=2, DispCorr=EnerPres, optimize_fft=yes). The root mean squared fluctuation (rmsf) of each atom during the last nanosecond of the simulation was calculated using Gromacs rmsf utility. The rmsf for each amino acid was determined by averaging the rmsf for all the atoms in the amino acid.

Results

To better understand the molecular basis for the observed differences in $\beta^3$-amino acid tolerance, molecular dynamic simulations (MD) of TyrRS and PheRS, the aaRS enzymes representing the lowest and highest tolerance, respectively, for $\beta^3$-amino acid substrates were carried out. Crystal structures of *E. coli* TyrRS (Kobayashi, et al., *Mol Biol,* 346:105 (2005)) and PheRS (Mermershtain, et al., *Prot Sci,* 20:160 (2011)) and structures of $\beta^3$-Tyr and $\beta^3$-Phe were modeled in Gaussian. MD simulations of TyrRS performed for 4 ns in the presence of $Mg^{2+}$ and either $\alpha$-Tyr or $\beta^3$-Tyr reveal significant differences in the position and dynamics of several TyrRS amino acids previously shown to promote adenylation. In particular, there were differences in the dynamics of K85, K89, K235, K238, which include the essential KMSKS loop (Kobayashi, et al., *Mol Biol,* 346:105 (2005)) and their ability to support the hydrogen bond networks implicated in substrate binding and catalysis. Perhaps most striking were differences in coordination of $Mg^{2+}$ ions that stabilize the pyrophosphate leaving group (Leatherbarrow, et al., *Proc Natl Acad Sci USA,* 82:7840 (1985)). Two $Mg^{2+}$ interact with the pyrophosphate when $\alpha$-Tyr is present, while only one $Mg^{2+}$ is found in the $\beta^3$-Tyr complex. Analogous MD simulations with PheRS revealed very few differences in the substrate-dependent dynamics of the MD trajectories or $Mg^{2+}$ coordination (FIG. 2A). It has been proposed that class II aminoacyl-tRNA synthetases evolved to discriminate among different amino acid substrates mainly by altering their amino acid binding pockets (Kavran, et al., *Proc Natl Acad Sci USA,* 104:11268 (2007)). The results of the modeling are consistent with this conclusion, and further indicate that class II aaRS enzymes may represent better starting points for the development of orthogonal aaRS enzymes that selectively incorporate diverse $\beta^3$-amino acids.

Example 3

EF-Tu varies on 3- to 8-Fold with $\alpha$-/$\beta^3$-Amino Acid Identity

Materials and Methods

Determination of EF-Tu-aatRNA Equilibrium Dissociation Constants

Aminoacylated tRNA was labeled with $^{32}P$ using CCA-adding enzyme as described above in (iii and iv). With these labeled tRNAs, equilibrium dissociation constants were determined using a standard RNA protection assay that monitored the extent of RNase A digestion of each $^{32}P$-labeled aminoacyl tRNA as a function of [EF-Tu•GTP] (Asahara, et al., *Biochemistry,* 44:11254 (2005)). Briefly, EF-Tu was first converted to the EF-Tu•GTP complex by incubating 8 µM EF-Tu•GDP (the form in which EF-Tu is purified from *E. coli*) with 100 mM HEPES (pH 7.0), 20 mM $MgCl_2$, 100 mM KCl, 5 mM DTT, 1 mM GTP, 3 mM phosphoenolpyruvate and 5U pyruvate kinase (Sigma) for 20 min at 37° C. (1 mL total volume). EF-Tu•GTP concentrations between 1 nM and 1 µM were prepared by serial dilution with HEPES buffer (100 mM HEPES (pH 7.0), 100 mM KCl) and mixed with 10 nM $^{32}P$-labeled aminoacyl tRNA (final concentration after mixing) on ice. After a 20 min incubation on ice, 5 µL of 0.1 mg/mL RNase A (Sigma) was added. After 20 sec, RNase A digestion was stopped by the addition of 5 µL of 1 mg/mL unfractioned tRNA (Sigma) followed by precipitation with 10% (w/v) trichloroacetic acid. The precipitate was collected on a Protran BA85 nitrocellulose membrane (Whatman), washed six times with 200 µL 5% (w/v) trichloroacetic acid and once with EtOH. The membrane was allowed to dry, exposed overnight to a BAS Storage Phosphor Screen, and evaluated using a Typhoon™ FLA 9500 biomolecule imager. Data was fit to a quadratic equation (Equation 3), which is appropriate because [EF-Tu] and [aminoacyl-tRNA] are comparable (Sanderson, et al., *Biochemistry,* 46:6194 (2007)).

Equation 3

$$y = \frac{(EF-Tu_T + aatRNA_T + K_D) - \sqrt{(EF-Tu_T + aatRNA_T + K_D)^2 - 4*(EF-Tu_T * aatRNA_T)}}{2}$$

In equation 3, y represents the fraction of EF-Tu-aatRNA complex, $EF-Tu_T$ represents the total concentration of EF-Tu, $aatRNA_T$ represents the total concentration of aa-tRNA (10 nM), and $K_D$ is the equilibrium dissociation constant (all units of concentration are in nM).

Results

Once aminoacylated, tRNAs are delivered to the ribosome by the translation factor EF-Tu in complex with GTP. In some cases, EF-Tu interacts principally with the tRNA body, while in others it interacts with the amino acid side chain; these interactions are balanced to ensure efficient delivery of all twenty natural α-amino acids (LaRiviere, et al., Science, 294:165 (2001)). Poor EF-Tu binding and delivery of mis-aminoacyl-tRNAs is associated with inefficient incorporation of N-methyl amino acids, analogs with bulky side chains and phosphorylated amino acids (Leong, et al., RNA, 20:632 (2014); Leong, et al., J Am Chem Soc, 134:17955 (2012); Miller, et al., FEBS Lett, 589:2194 (2015); Wang, et al., ACS Chem Biol, 9:1303 (2014)). In certain cases, EF-Tu re-engineering has been necessary to achieve high incorporation levels (Ohtsuki, et al., Biochem, 148:239 (2010); Park, et al., Science, 333:1151 (2011)). To evaluate whether re-engineering would be necessary for tRNAs carrying $\beta^3$-amino acids, use of an RNase protection assay (Pleiss, et al., J Mol Biol, 308:895 (2001)) was used to determine how the equilibrium binding affinity for EF-Tu varies with α-/$\beta^3$-amino acid identity. For three of five side chains evaluated (Gly, Glu, and Tyr), EF-Tu was relatively insensitive to the amino acid backbone, binding with roughly equal affinity to the acylated and misacylated cognate tRNA (FIGS. 3A-3F). In two cases (Met and Phe), EF-Tu showed a small preference (3-8 fold) for the α-amino acid-containing tRNA but still bound the tRNA carrying the β-amino acid with a $K_D$ in the nM range. As a difference of at least 10-fold in $K_D$ is required to impair EF-Tu binding and aminoacyl-tRNA delivery to the ribosome (Leong, et al., RNA, 20:632 (2014); Mittelstaet, et al., J Am Chem Soc, 135:17031 (2013)), the small differences observed here should impact EF-Tu only minimally, allowing ribosome delivery of a diverse set of tRNAs mis-acylated with $\beta^3$-amino acids (Dale, et al., Biochemistry, 43:6159 (2004)).

Example 4

P7A7 Ribosomes Modulate Improved $\beta^3$ Amino Acid Incorporation in Nascent Peptide Chains Materials and Methods Generation of Erythromycin-Resistant E. coli Strains A library of erythromycin-resistant E. coli strains (>8000 unique clones, with a theoretical diversity of 8192) was generated using a modified version of the procedure reported by Hecht (Dedkova, et al., Biochemistry, 51:401 (2012); Maini, et al., Bioorg Med Chem, 21:1088 (2013)). Beginning with a pUC18 plasmid (pUC-rrnb-040329, Hecht lab, Arizona State) which encodes a mutant E. coli 23S rRNA with the sequence AGCGTGA from 2057-2063 and the sequence TGGCAG at positions 2502-2507, and used Gibson Assembly to introduce diversity at positions 2496-2507 to generate the plasmid library pUC18-WR Library 1. Greater than 8000 clones of a sequence whose theoretical diversity was 8192 were generated. The rrnb sequence was randomized using dsDNA fragments (gBlocks) synthesized to contain a 1:1:1:1 ratio of all four possible bases (NNNNNN, with N=A, T, C, or G) at positions 2496-2501 (dsDNA fragment 1) or 2502-2507 (dsDNA fragment 2) (Dedkova, et al., Biochemistry, 51:401 (2012)). Gibson Assembly of dsDNA fragment 1 or 2 with the parent plasmid pUC18 rrnb was performed for 3 h at 50° C. with Gibson Assembly Master Mix (New England BioLabs). For transformations, 3 µL of the Gibson Assembly product (diluted 1 to 4 into $H_2O$) was mixed into 50 µL of BL21 (DE3) cells (Agilent). The Gibson Assembly product was transformed by electroporation using a BTX® Electro Cell Manipulator 600. The cells were allowed to recover immediately following electroporation in 1 mL of Super Optimal Broth (SOB) media and then grown for 1.5 h at 37° C. while shaking (200 rpm). The cells were then spun down to a pellet prior to diluting into 300 µL of SOB media and plating 100 µL per LB agar plate containing 100 µg/mL of carbenicillin. After incubating the plates at 37° C. for 18 h, carbenicillin-resistant colonies were inoculated into 0.5 mL of LB media containing 100 µg/mL of carbenicillin and grown at 37° C. while shaking (200 rpm). Upon reaching $OD_{600}$=0.2-0.5, the cells were then diluted to 15% glycerol stocks and stored at −20° C.

Screen of Erythromycin-Resistant Library for Sensitivity to Antibiotics

To screen the resulting E. coli strains for antibiotic resistance, 2 µL of the 15% glycerol stocks prepared above were added to 98 µL of growth assay buffer (LB media (pH 8.35), 100 µg/mL carbenicillin, 1.0 mM IPTG, 6.8 µM erythromycin) in 384-well plates (Corning #3707). Two plates were assembled for each experiment: 1 contained antibiotic (6.8 µM erythromycin) and 1 did not (0 µM of erythromycin). After 16-18 h, the extent of cell growth inhibition in the presence of antibiotic was determined by measuring the $OD_{600}$ of each well using a SpectraMax M5 plate reader (Molecular Devices). The antibiotic-dependent inhibition of cell growth in each well was determined using Equation 4:

$$[100-(OD_{600+A}/OD_{600-A}) \times 100]$$  Equation 4

In this equation, $OD_{600+A}$ represents $OD_{600}$ of wells containing antibiotic and $OD_{600-A}$ represents $OD_{600}$ of wells lacking antibiotic. E. coli transformed with a pUC18 plasmid encoding the WT rrnb sequence exhibited full growth inhibition in the erythromycin screen (6.8 µM). Resistant clones were defined as those displaying <20% of growth inhibition relative to WT; 1986 (2000) clones were identified as erythromycin-resistant.

Screen of Erythromycin-Resistant Library for Sensitivity to $\beta^3$-Puromycin

The 1986 erythromycin-resistant clones identified above were then screened for sensitivity to $\beta^3$-puromycin sensitivity as described above, except that 250 µM $\beta^3$-puromycin was substituted for erythromycin. E. coli transformed with a pUC18 plasmid encoding the WT rrnb sequence exhibited a lack of growth inhibition in the $\beta^3$-puromycin screen, which utilized a selection cutoff of >30% growth inhibition to identify sensitive clones.

Expression of DHFR Containing $\beta^3$-Amino Acids

To evaluate the extent of in vivo $\beta^3$-amino acid incorporation, BL21 (DE3) cells were co-transformed via electroporation (vide infra) with two plasmids. One plasmid (pET28a-DHFR-1) encoded an N-terminal $His_6$-tagged DHFR variant containing a single Phe codon at position 128 and a single S to R mutation at position 126. The other plasmid encoded either the WT rrnb sequence (pLK35-rrnb), the 040329 mutant reported by Hecht (pLK35-040329.rrnb), or the P7A7 mutant (pLK35-P7A7.rrnb) identified during the puromycin sensitivity screen described above.

i. Plasmid construction. pLK35-rrnb encodes a WT rrnb sequence and was obtained from the Dahlberg laboratory, Brown University. pLK35-m.rrnb plasmids encode mutant rrnb sequences identified from the $\beta^3$-puromycin screen and were created by introducing the mutant 2051-2586 sequence into the pLK35-rrnb plasmid via Gibson Assembly (vide infra). pET28a-DHFR-1 was generated from pET28a-DHFR plasmid (Dr. Shinsuke Sando, University of Tokyo) by the addition of an N-terminal His-tag and by introducing mutations that changed the residue encoded at position 126 from Ser (codon TCG) to Arg (codon CGG). Mutations were introduced via Gibson Assembly. The amino acid sequence of DHFR is provided below. Following electroporation, cells were allowed to recover in 1 mL of SOB medium for 1 h at 37° C. and then plated on LB agar plates containing 50 ng/mL of kanamycin and 100 ng/mL of carbenicillin. After 18 h, dozens of individual colonies were present, from which a single colony was picked and grown overnight in 5 mL of LB containing 50 ng/mL of kanamycin and 100 ng/mL of carbenicillin. To confirm that both plasmids were maintained, plasmid DNA was purified using a Qiagen miniprep kit (product 27105) and sequenced by the Keck Foundation Biotechnology Resource Laboratory at Yale University.

ii. $\beta^3$-amino acid incorporation. The subsequent protocol for in vivo $\beta^3$-amino acid incorporation employed minimal media and was adapted from procedures reported by Tirrell and Cropp (Liu, et al., *Bioorg Med Chem Lett*, 20:5613 (2010); Mandavi, et al., *J Am Chem Soc*, 135:2979 (2013)). Briefly, all 5 mL of the co-transformed cells prepared as described above were diluted into 100 mL of LB containing 50 ng/mL of kanamycin and 100 ng/mL of carbenicillin and grown to $OD_{600}=1.0$, spun down, and then resuspended in 1/10$^{th}$ the original volume of 19/20 minimal media (10.5 g/L M9 salts, 0.1 mM $CaCl_2$, 1 mM $MgSO_4$, 1% glycerol, 100 µM of each amino acid (minus α-Phe), 25 mg/L thiamine, 100 ng/mL carbenicillin, 30 ng/mL kanamycin, 1 mM IPTG) supplemented with 1 mM of α-Phe or a $\beta^3$-Phe analog. Cells were grown overnight (18 h) at 37° C. while shaking (200 rpm). The cells were harvested by centrifugation (10 min at 4000×g) and resuspended in lysis buffer (50 mM $NaH_2PO_4$, 300 mM NaCl, 10 mM imidazole (pH 8.0)). Lysis was performed by sonication (Branson Sonifier 250) with 5 cycles of 20 s on, 20 s off. Lysed cells were then centrifuged for 20 min at 15000×g. The clarified cell lysate was incubated with Ni-NTA resin (Qiagen) for 1 h while gently rotating at 4° C. The Ni-NTA column was washed with lysis buffer prior to eluting proteins with elution buffer (50 mM $NaH_2PO_4$, 300 mM NaCl, 300 mM imidazole (pH 8.0)). Elutions were analyzed with SDS-PAGE to prepare material for in-gel trypsin digestions. Controls included side-by-side growths in (1) unsupplemented 19/20 minimal media, which contains only low levels of α-Phe present (negative control); (2). 19/20 minimal media supplemented with 1 mM α-Phe (positive control) and (3) and 19/20 minimal media supplemented with 1 mM $\beta^3$-Gly (negative control; $\beta^3$-aa that is not a $\beta^3$-Phe analog).

Proteomic Analysis of Translated DHFR i. Generation of tryptic fragments. The incorporation of $\beta^3$-Phe analogs into DHFR was verified by mass spectrometry, by examining the masses of peptides produced by in-gel trypsin digestions of Ni-NTA purified DHFR. Standard in-gel trypsin digestion procedures were performed to yield DHFR tryptic peptides. Briefly, 1 mm×1 mm minced gel pieces were washed three times with 100 µL of 50% acetonitrile/50 mM ammonium bicarbonate buffer (pH 8.0) followed by 500 µL of 100% acetonitrile to remove the bulk of Coomassie stain. The residual solvent was removed by aspiration, and the gel pieces were subsequently incubated with 10 mM dithiothreitol (DTT) in 50 mM ammonium bicarbonate (pH 8.0) (50-75 µL) for 1 h at 60° C. to reduce thiols. Following reduction, a solution of 20 mM iodoacetamide (IAA) in 50 mM ammonium bicarbonate (50-75 µL) was added and samples were incubated at 45° C. for 45 min. Reduced/alkylated gel pieces were then washed three times with 50 mM ammonium bicarbonate (100 µL) followed by 100% acetonitrile (50 µL) and dried in a Speed Vac. Trypsin digestions were initiated upon addition of a 20 ng/µL solution of trypsin (Promega) in 50 mM ammonium bicarbonate in a sufficient volume to cover the gel pieces, and incubated on ice for 4 h and then overnight at 37° C. Tryptic peptides were extracted from the gel pieces with three 50 µL aliquots of a 50% acetonitrile/5% formic acid solution and once with 100% acetonitrile (50 µL). The collected tryptic peptides were dried in a Speed Vac prior to resuspending in 0.1% formic acid to a peptide concentration of 100 ng/µL.

ii. Mass spectrometry. Tryptic peptides analyzed using an Agilent 6550 Q-TOF instrument were first separated on a Polaris-HR-Chip 3C18 (Agilent #G4240-62030) with a 360 nL trap column and a 75 µm ID×150 mm analytical column packed with 3 µm C18 particles. The capillary and nano pumps utilized 0.1% formic acid as eluent A and 90% acetonitrile with 0.1% formic acid as eluent B. The enrichment column was operated in a vented split design with a flow rate of 2.0 µL/min. The enrichment eluent composition was 2% B and the injection volume was 1 µL, which corresponds to 100 ng of injected peptide material. The sample flush volume for the ChipCube was 6 µL. The analytical column was operated at a flow rate of 0.3 µL/min with the following gradient: 2% B at 2 min, 40% B at 17 min, 70% B at 18 min, 70% B at 22 min, and 3% B at 23 min. At 20 min, the enrichment column was switched back to sample trapping to prepare for column equilibration prior to subsequent sample injection. Mass spectra were searched against the *E. coli* proteome (BL21 (DE3) strain; unipro-t.org) with a custom database containing the N-terminally His-tagged DHFR with a single phenylalanine at position 128. The proteomic analysis software MyriMatch and SpectrumMill (Agilent) were used for database searching (Tabb, et al., *J Proteome Res*, 6:654 (2007)). Forward and decoy database searches were performed with full trypsin specificity allowing up to 3 missed cleavages and 6 total modifications per peptide. Searches were restricted to a mass tolerance of ±25 ppm for the MS precursor ion and ±0.1 Da for MS/MS fragment ions. Static modifications included the alkylation of cysteines with IAA (+57.0214 Da), while variable modifications included the oxidation of methionine (+15.9949 Da). In order to detect peptides containing a β-Phe analog, variable custom modifications for phenylalanine were included with the monoisotopic masses of +91.9375/+93.9355 for $\beta^3$-Br-hPhe.

DHFR
(SEQ ID NO: 7)
MHHHHHHENAMPWNLPADLAWVKRNTLNKPVIMGRHTWESIGRPL

PGRKNIILSSQPGTDDRVTWVKSVDEAIAACGDVPEIMVIGGGRVYE

-continued

QLLPKAQKLYLTHIDAEVEGDTHYPDYEPDDWERVFSEYHDADAQN

SHSYCYEILERRGSRSHHHHHH

Results

Figure 4A:
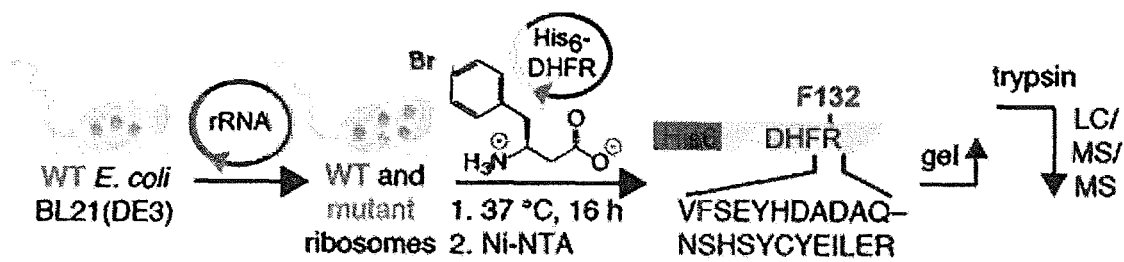
FIG. 4A is a scheme showing an experimental assay for testing in vivo incorporation of $β^3$-Phe analogs by *E. coli* harboring mutant ribosomes.

Building on the knowledge that E. coli PheRS effectively mis-aminoacylates tRNA$^{Phe}$ with $\beta^3$-Phe (FIGS. 1A-1E) and that E. coli EF-Tu interacts efficiently with the $\beta^3$-Phe-tRNA$^{Phe}$ complex (FIG. 3A-3F), experiments were designed to determine whether E. coli expressing previously reported mutant ribosomes (Dedkova, et al., Biochemistry, 51:401 (2012); Maini, et al., Biochemistry (2015); Maini, et al., Bioorg Med Chem, 21:1088 (2013)) could support the incorporation of $\beta^3$-Phe analogs into DHFR in vivo. The $\beta$-puromycin-sensitive ribosome that exhibited the highest suppression efficiency for translation in vitro with a tRNA chemically mis-acylated with $\beta$-ArA (FIG. 1A) was selected for initial testing. This ribosome contains the mutant 23S sequence referred to as 040329, with 13 base changes between residues 2057 and 2507. E. coli BL21(DE3) cells were transformed with a pUC18 plasmid encoding either WT or 040329 23S rRNA as well as one encoding DHFR with a single UUC codon at position 128 (FIGS. 4A-4E) (Dedkova, et al., Biochemistry, 51:401 (2012); Kanatani, et al., Nucl Acids Symp Ser, 265 (2005)). Cells were grown in the presence of $^{19}/_{20}$ minimal media containing all α-amino acids except α-Phe and supplemented (or not) with α-Phe, $\beta^3$-Gly, $\beta^3$-Phe, or a brominated $\beta^3$-Phe derivative $\beta$-(p-Br) Phe. Translated DHFR was isolated using a Ni(II)-nitrilotriacetic acid resin and analyzed by SDS-PAGE (FIG. 4F) and mass spectrometry (FIGS. 4G-4I).

BL21(DE3) cells expressing only WT ribosomes generated only trace amounts of DHFR when grown in unsupplemented $^{19}/_{20}$ minimal media, or in media supplemented with $\beta^3$-(p-Br)Phe or $\beta^3$-Gly; higher levels of DHFR (approximately 8-fold) were observed when α-Phe was added. Cells expressing 040329 ribosomes along with WT ribosomes also generated trace amounts of DHFR when grown in unsupplemented $^{19}/_{20}$ minimal media, however in this case, significant levels of DHFR were observed when the media was supplemented with $\beta^3$-(p-Br)Phe or $\beta^3$-Gly as well as α-Phe. To confirm that $\beta^3$-(p-Br)Phe was incorporated at position 128 of the DHFR translated in these cells, the isolated full length (19 kDa) DHFR was digested with trypsin and analyzed by LC-MS/MS (FIG. 4C). Tryptic peptides comprising DHFR residues 127-149 and containing either α-Phe or $\beta^3$-(p-Br)Phe at position 128 were detected (FIGS. 4G-4I); no evidence for $\beta^3$-Gly incorporation was found. Spectral counting revealed a 30-fold lower incorporation of $\beta^3$-(p-Br)Phe relative to α-Phe (Table 6).

TABLE 6

Spectral counting analysis of the extent of $\beta^3$-(p-Br)Phe and α-Phe incorporation into DHFR by E. coli harboring 040329 and p7A7 mutant ribosomes The spectra for peptides containing $\beta^3$-(p-Br)Phe includes both +91.9 and +93.9 isotopes of Bromine, with the +93.9 isotope included in the value listed for the calculated molecular weight (MW$_{calc}$)

| Ribosome | Peptide | X | MW$_{calc}$ | Spectra | $\beta^3$-(p-Br)Phe:α-Phe |
|---|---|---|---|---|---|
| 040329 | VXSEYHDADAQNSHSYCYEILER (SEQ ID NO: 8) | α-Phe | 2832.208 | 271 | 1:34 |
|  | VXSEYHDADAQNSHSYCYEILER (SEQ ID NO: 9) | $\beta^3$-Br-hPhe | 2926.144 | 8 |  |
| P7_A7 | VXSEYHDADAQNSHSYCYEILER (SEQ ID NO: 8) | α-Phe | 2832.208 | 145 | 1:9 |
|  | VXSEYHDADAQNSHSYCYEILER (SEQ ID NO: 9) | $\beta^3$-Br-hPhe | 2926.144 | 16 |  |

Figure 5A:
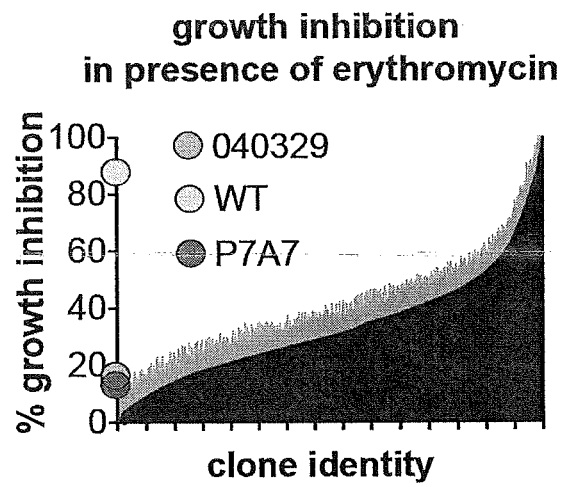
FIG. 5A is a plot showing the growth inhibition of 7659 clones in the presence of 6.8 μM erythromycin.
Figure 5B:
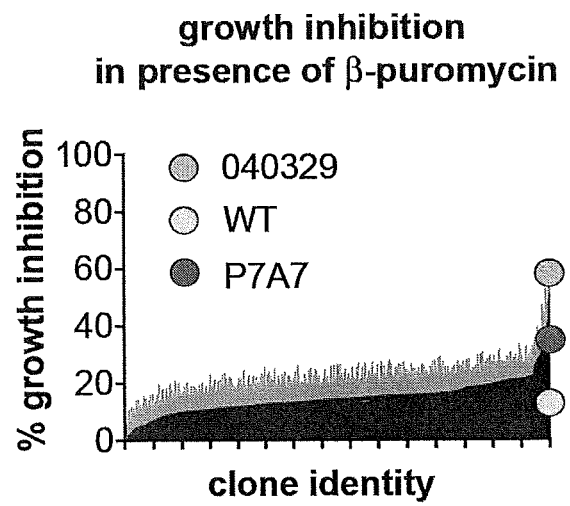
FIG. 5B is a plot of the % growth inhibition of 1957 clones in the presence of 250 μM β-puromycin.
Figure 6:
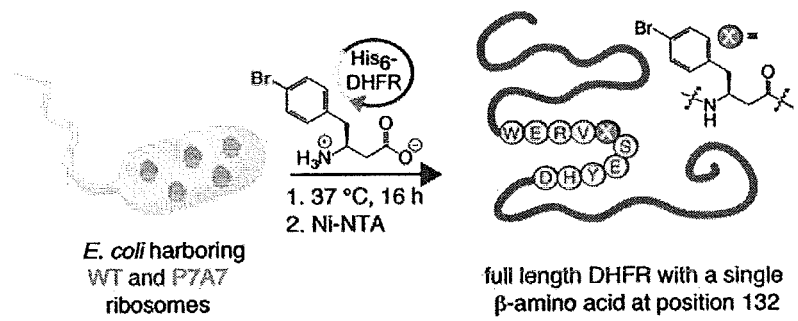
FIG. 6 is an illustration of site-specific incorporation of β-amino acid ($β^3$-Phe analog) in dihydrofolate reductase (DHFR) protein during translation in vivo in *E. coli*, expressing wildtype and P7A7 ribosomes.

Experiments were designed to determine if ribosomes with improved efficiency and selectivity could be obtained by a more complete analysis of 23S rRNA sequence space. Additional diversity was introduced into the 040329 23S rRNA between positions 2496-2507, a region adjacent to the A-site, to generate >8000 unique clones (theoretical diversity=8192) and screened them to identify members that were both resistant to erythromycin (6.8 μM) and sensitive to β-puromycin (250 μM). Approximately 2000 clones were resistant to 6.8 μM erythromycin, showing <20% inhibition of growth relative to wild type (FIG. 5A). The 2000 erythromycin-resistant clones were then screened for sensitivity to 250 μM β-puromycin (FIG. 5B); in this case only 2% of the 2000 clones showed >30% inhibition. Examination of the 44 sensitive clones revealed a preponderance of two 23S rRNA sequences: the previously reported 040329 mutant and a new mutant, P7A7, that differed at 12 positions within the 23S rRNA, containing the sequence UGACUU at positions 2502-2507 in place of GAUGUC.

P7A7 rRNA Sequence:

(SEQ ID NO: 4)
AGCGUUCUUUGAAGUGCUCACACAGAUUGUCUGAUGAAAAUGA

GCAGUAAAACCUCUACAGGCUUGUAGCUCAGGUGGUUAGAGCG

CACCCCUGAUAAGGGUGAGGUCGGUGGUUCAAGUCCACUCAGG

CCUACCAAAUUUGCACGGCAAAUUUGAAGAGGUUUUAACUACA

UGUUAUGGGGCUAUAGCUCAGCUGGGAGAGCGCCUGCUUUGCA

CGCAGGAGGUCUGCGGUUCGAUCCCGCAUAGCUCCACCAUCUCU

GUAGUGAUUAAAUAAAAAAUACUUCAGAGUGUACCUGCAAAGG

UUCACUGCGAAGUUUUGCUCUUUAAAAAUCGGGAUCAAGCUGA
AAAUUGAAACACUGAACAACGAAAGUUGUUCGUGAGUCUCUCA
AAUUUUCGCAACACGAUGAUGAAUCGAAAGAAACAUCUUCGGG
UUGUGAGGUUAAGCGACUAAGCGUACACGGUGGAUGCCCUGGC
AGUCAGAGGCGAUGAAGGACGUGCUAAUCUGCGAUAAGCGUCG
GUAAGGUGAUAUGAACCGUUAUAACCGGCGAUUUCCGAAUGGG
GAAACCCAGUGUGUUUCGACACACUAUCAUUAACUGAAUCCAU
AGGUUAAUGAGGCGAACCGGGGGAACUGAAACAUCUAAGUACC
CCGAGGAAAAGAAAUCAACCGAGAUUCCCCCAGUAGCGGCGAG
CGAACGGGGAGCAGCCCAGAGCCUGAAUCAGUGUGUGUGUUAG
UGGAAGCGUCUGGAAAGGCGUGCGAUACAGGGUGACAGCCCCG
UACACAAAAAUGCACAUGCUGUGAGCUCGAUGAGUAGGGCGGG
ACACGUGGUAUCCUGUCUGAAUAUGGGGGGACCAUCCUCCAAG
GCUAAAUACUCCUGACUGACCGAUAGUGAACCAGUACCGUGAG
GGAAAGGCGAAAAGAACCCCGGCGAGGGGAGUGAAAAAGAACC
UGAAACCGUGUACGUACAAGCAGUGGGAGCACGCUUAGGCGUG
UGACUGCGUACCUUUUGUAUAAUGGGUCAGCGACUUAUAUUCU
GUAGCAAGGUUAACCGAAUAGGGGAGCCGAAGGGAAACCGAGU
CUUAACUGGGCGUUAAGUUGCAGGGUAUAGACCCGAAACCCGG
UGAUCUAGCCAUGGGCAGGUUGAAGGUUGGGUAACACUAACUG
GAGGACCGAACCGACUAAUGUUGAAAAAUUAGCGGAUGACUUG
UGGCUGGGGGUGAAAGGCCAAUCAAACCGGGAGAUAGCUGGUU
CUCCCCGAAAGCUAUUUAGGUAGCGCCUCGUGAAUUCAUCUCCG
GGGGUAGAGCACUGUUUCGGCAAGGGGGUCAUCCCGACUUACC
AACCCGAUGCAAACUGCGAAUACCGGAGAAUGUUAUCACGGGA
GACACACGGCGGGUGCUAACGUCCGUCGUGAAGAGGGAAACAA
CCCAGACCGCCAGCUAAGGUCCCAAAGUCAUGGUUAAGUGGGA
AACGAUGUGGGAAGGCCCAGACAGCCAGGAUGUUGGCUUUGAA
GCAGCCAUCAUUUAAAGAAAGCGUAAUAGCUCACUGGUCGAGU
CGGCCUGCGCGGAAGAUGUAACGGGGCUAAACCAUGCACCGAA
GCUGCGGCAGCGACACUAUGUGUUGUUGGGUAGGGGAGCGUUC
UGUAAGCCUGUGAAGGUGUGCUGUGAGGCAUGCUGGAGGUAUC
AGAAGUGCGAAUGCUGACAUAAGUAACGAUAAAGCGGGUGAAA
AGCCCGCUCGCCGGAAGACCAAGGGUUCCUGUCCAACGUUAAUC
GGGGCAGGGUGAGUCGACCCCUAAGGCGAGGCCGAAAGGCGUA
GUCGAUGGGAAACAGGUUAAUAUUCCUGUACUUGGUGUUACUG
CGAAGGGGGGACGGAGAAGGCUAUGUUGGCCGGGCGACGGUUG
UCCCGGUUUAAGCGUGUAGGCUGGUUUUCCAGGCAAAUCCGGA
AAAUCAAGGCUGAGGCGUGAUGACGAGGCACUACGGUGCUGAA
GCAACAAAUGCCCUGCUUCCAGGAAAAGCCUCUAAGCAUCAGG

-continued

UAACAUCAAAUCGUACCCCAAACCGACACAGGUGGUCAGGUAG
AGAAUACCAAGGCGCUUGAGAGAACUCGGGUGAAGGAACUAGG
CAAAAUGGUGCCGUAACUUCGGGAGAAGGCACGCUGAUAUGUA
GGUGAAGCGACUUGCUCGUGGAGCUGAAAUCAGUCGAAGAUAC
CAGCUGGCUGCAACUGUUUAUUAAAAACACAGCACUGUGCAAA
CACGAAAGUGGACGUAUACGGUGUGACGCCUGCCCGGUGCCGG
AAGGUUAAUUGAUGGGGUUAGCCGCAAGGCGAAGCUCUUGAUC
GAAGCCCCGGUAAACGGCGGCCGUAACUAUAACGGUCCUAAGG
UAGCGAAAUUCCUUGUCGGGUAAGUUCCGACCUGCACGAAUGG
CGUAAUGAUGGCCAGGCUGUCUCCACCCGAGACUCAGUGAAAU
UGAACUCGCUGUGAAGAUGCAGUGUACCCGCGGCAAGACGAGC
GUGACCCGUGAACCUUUACUAUAGCUUGACACUGAACAUUGAG
CCUUGAUGUGUAGGAUAGGUGGGAGGCUUUGAAGUGUGGACGC
CAGUCUGCAUGGAGCCGACCUUGAAAUACCACCCUUUAAUGUU
UGAUGUUCUAACGUUGACCCGUAAUCCGGGUUGCGGACAGUGU
CUGGUGGGUAGUUUGACUGGGGCGGUCUCCUCCUAAAGAGUAA
CGGAGGAGCACGAAGGUUGGCUAAUCCUGGUCGGACAUCAGGA
GGUUAGUGCAAUGGCAUAAGCCAGCUUGACUGCGAGCGUGACG
GCGCGAGCAGGUGCGAAAGCAGGUCAUAGUGAUCCGGUGGUUC
UGAAUGGAAGGGCCAUCGCUCAACGGAUAAAAGGUACUCCGGG
GAUAACAGGCUGAUACCGCCCAAGAGUUCAUAUCGACGGCGGU
GUUUGGCACCUCUGACUUGGCUCAUCACAUCCUGGGGCUGAAG
UAGGUCCCAAGGGUAUGGCUGUUCGCCAUUUAAAGUGGUACGC
GAGCUGGGUUUAGAACGUCGUGAGACAGUUCGGUCCCUAUCUG
CCGUGGGCGCUGGAGAACUGAGGGGGGCUGCUCCUAGUACGAG
AGGACCGGAGUGGACGCAUCACUGGUGUUCGGGUUGUCAUGCC
AAUGGCACUGCCCGGUAGCUAAAUGCGGAAGAGAUAAGUGCUG
AAAGCAUCUAAGCACGAAACUUGCCCCGAGAUGAGUUCUCCCU
GACUCCUUGAGAGUCCUGAAGGAACGUUGAAGACGACGACGUU
GAUAGGCCGGGUGUGUAAGCGCAGCGAUGCGUUGAGCUAACCG
GUACUAAUGAACCGUGAGGCUUAACCUUACAACGCCGAAGGUG
UUUUGGCGGAUUGAGAGAAGAUUUUCAGCCUGAUACAGAUUAA
AUCAGAACGCAGAAGCGGUCUGAUAAAACAGAAUUUGCCUGGC
GGCAGUAGCGCGGUGGUCCCACCUGACCCCAUGCCGAACUCAGA
AGUGAAACGCCGUAGCGCCGAUGGUAGUGUGGGGUCUCCUCAU
GCGAGAGUAGGGAACUGCCAGGCAUCAAAUAAAACGAAAGGCU
CAGUCGGAAGACUGGGCCUUUCGUUUUAUCUGUUGUUUGUCGG
UGAACGCUCUCCUGAGUAGGACAAAUCCGCCGGGAGCGGAUUU
GAACGUUGCGAAGCAACGGCCCGGAGGGUGGCGGGCAGGACGC
CCGCCAUAAACUGCCAGGCAUCAAAUUAAGCAGAAGGCCAUCCU
GACGGAUGGCCUUUUUGCAUUGGCGCAGAAA.

UGACUU at positions 2502-2507 in place of GAUGUC, and AGCGUGA from 2057-2063 relative to SEQ ID NO:1 are bolded and underlined.

Figure 4B:
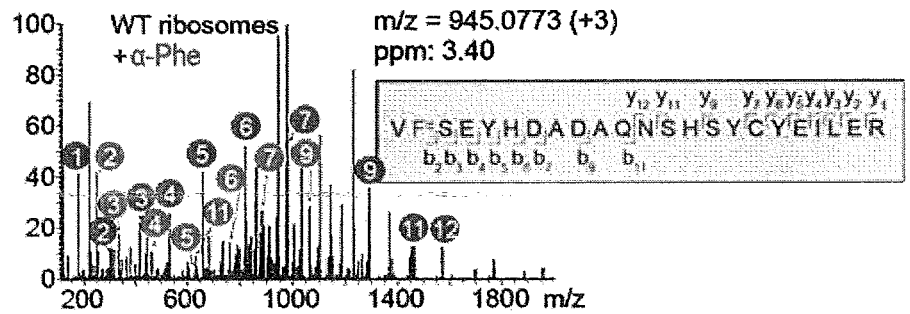
FIGS. 4B-4D are LC-MS/MS spectra showing incorporation of $β^3$-Phe analogs by *E. coli* harboring wildtype ribosomes (from left to right on the spectra the numbered, labeled circles identify: y1, b2, y2, b3, y3, b4, y4, b5, b11, y5, b6, y6, b7, y7, b9, y9, y11, y12) (4B); 040329 ribosomes (from left to right on the spectra the numbered, labeled circles identify: b2, y1, b4, y2, y3, y4, y5, y6, b22, b23, y7, b8, b17, y8, y9, y10, y11, y12) (4C); or P7A7 ribosomes (from left to right on the spectra the numbered, labeled circles identify: y1, y2, b2, b5, y3, y4, y5, b11, y6, b11, y19, b14, b6, y22, b7, y7, y8, y9, y11, y12) (4D).
Figure 4C:
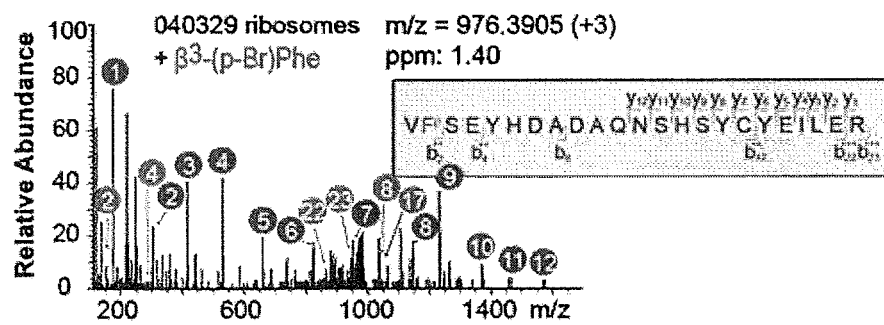
Figure 4D:
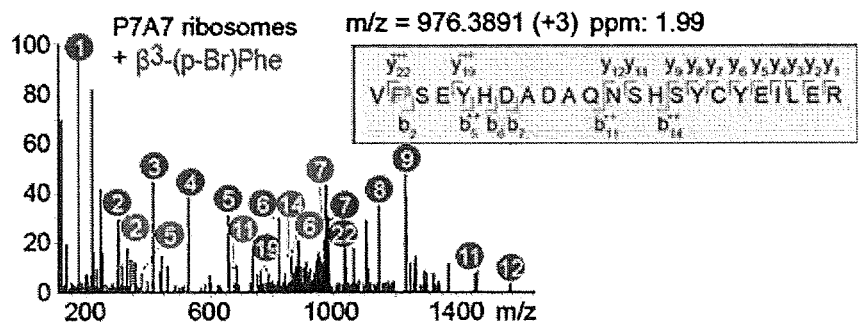

Cells expressing P7A7 ribosomes along with WT ribosomes also generated trace amounts of DHFR when grown in unsupplemented ¹⁹⁄₂₀ minimal media, however in this case, the highest levels of DHFR were observed when the media was supplemented with $\beta^3$-(p-Br)Phe; lower levels were observed when the cells were treated with α-Phe or $\beta^3$-Gly (FIG. 4B). To confirm that $\beta^3$-(p-Br)Phe was incorporated at position 128 of the DHFR translated in these cells, the isolated full length DHFR was digested with trypsin and analyzed by LC-MS/MS as described above; tryptic peptides comprising DHFR residues 127-149 and containing either α-Phe or $\beta^3$-(p-Br)Phe at position 128 were detected (FIG. 4C). In this case, spectral counting revealed a 10-fold lower incorporation of $\beta^3$-(p-Br)Phe relative to α-Phe (Table 6). Additional mass spectrometric analysis revealed that the $\beta^3$-(p-Br)Phe/α-Phe incorporation ratio was 3-fold greater in cells expressing P7A7 ribosomes than in cells expressing 040329 ribosomes (Table 6). Collectively, these data demonstrate that *E. coli* harboring mutant ribosomes have the capacity to incorporate highly unusual, non-natural, non-α-amino acids (NNAs) into protein in vivo.

SEQUENCE LISTING

```
<160> NUMBER OF SEQ ID NOS: 9

<210> SEQ ID NO 1
<211> LENGTH: 2904
<212> TYPE: RNA
<213> ORGANISM: Escherichia coli

<400> SEQUENCE: 1
gguuaagcga cuaagcguac acgguggaug cccuggcagu cagaggcgau gaaggacgug      60
cuaaucugcg auaagcgucg guaaggugau augaaccguu auaaccggcg auuuccgaau     120
ggggaaaccc aguguguuuc gacacacuau cauuaacuga auccauaggu uaaugaggcg     180
aaccggggga acugaaacau cuaaguaccc cgaggaaaag aaaucaaccg agauucccccc    240 aguagcggcg agcgaacggg gagcagccca gagccugaau cagugugugu guuaguggaa     300
gcgucuggaa aggcgcgcga uacaggguga cagccccgua cacaaaaaug cacaugcugu     360
gagcucgaug aguagggcgg gacacguggu auccugucug aauauggggg gaccauccuc     420
caaggcuaaa uacuccugac ugaccgauag ugaaccagua ccgugaggga aaggcgaaaa     480
gaaccccggc gaggggagug aaaaagaacc ugaaccgug uacguacaag cagugggagc      540
acgcuuaggc gugugacugc guaccuuuug uauaauggggu cagcgacuua uauucuguag    600
caagguuaac cgaauagggg agccgaaggg aaaccgaguc uuaacugggc guuaaguugc     660 agggauauaga cccgaaaccc ggugaucuag ccaugggcag guugaagguu ggguaacacu     720
aacuggagga ccgaaccgac uaauguugaa aaauuagcg augacuugug gcuggggug       780 aaaggccaau caaaccggga gauagcuggu ucuccccgaa agcuauuuag guagcgccuc     840
gugaauucau cuccggggu agagcacugu uucggcaagg gggucauccc gacuuaccaa      900
cccgaugcaa acugcgaaua ccggagaaug uuaucacggg agacacacgg cgggugcuaa    960
cguccgucgu gaagagggaa acaacccaga ccgccagcua agguccaaa gucaugguua     1020 agugggaaac gaugugggaa ggcccagaca gccaggaugu uggcuuagaa gcagccauca    1080
uuuaaagaaa gcguaauagc ucacggucg agucggccug cgcggaagau guaacggggc     1140
uaaaccaugc accgaagcug cggcagcgac gcuuaugcgu uguugggguag gggagcguuc    1200 uguaagccug cgaaggugug cugugaggca ugcuggaggu aucagaagug cgaaugcuga    1260
cauaaguaac gauaaagcgg gugaaaagcc cgcucgccgg aagaccaagg guccugucc    1320 aacguuaauc ggggcagggu gagucgaccc cuaaggcgag gccgaaaggc guagucgaug   1380
ggaaacaggu uaauauuccu guacuggug uuacugcgaa ggggggacgg agaaggcuau    1440
guuggccggg cgacgguugu cccguuuaa gcguguaggc ugguuuucca ggcaaauccg   1500
gaaaaucaag gcugaggcgu gaugacgagg cacuacggu cugaagcaac aaaugcccug  1560
cuuccaggaa aagccucuaa gcaucaggua acaucaaauc guaccccaaa ccgacacagg   1620
```

| | |
|---|---|
| uggucaggua gagaauacca aggcgcuuga gagaacucgg gugaaggaac uaggcaaaau | 1680 |
| ggugccguaa cuucgggaga aggcacgcug auauguaggu gagucccuc gcggauggag | 1740 |
| cugaaaucag ucgaagauac cagcuggcug caacuguuua uuaaaaacac agcacgugc | 1800 |
| aaacacgaaa guggacguau acggugugac gccugcccgg ugccggaagg uuaauugaug | 1860 |
| gguuagcgc aagcgaagcu cuugaucgaa gccccgguaa acggcggccg uaacuauaac | 1920 |
| gguccuaagg uagcgaaauu ccuugucggg uaaguuccga ccugcacgaa uggcguaaug | 1980 |
| auggccaggc ugucuccacc cgagacucag ugaaauugaa cucgcuguga agaugcagug | 2040 |
| uacccgcggc aagacggaaa gaccccguga accuuuacua uagcuugaca cugaacauug | 2100 |
| agccuugaug uguaggauag gugggaggcu uugaagugug gacgccaguc ugcauggagc | 2160 |
| cgaccuugaa auaccacccu uuaauguuug auguucuaac guugacccgu aauccggguu | 2220 |
| gcggacagug ucugguggu aguugacug gggcggucuc cuccuaaaga guaacggagg | 2280 |
| agcacgaagg uuggcuaauc cuggucggac aucaggaggu uagugcaaug gcauaagcca | 2340 |
| gcuugacugc gagcgugacg gcgcgagcag gugcgaaagc aggucauagu gauccggugg | 2400 |
| uucugaaugg aagggccauc gcucaacgga uaaaaagguac uccggggaua acaggcugau | 2460 |
| accgcccaag aguucauauc gacggcggug uuugcaccu cgaugucggc ucaucacauc | 2520 |
| cuggggcuga aguaggucc aagggauagg cguucgcca uuuaaaguag uacgcgagcu | 2580 |
| gggcuuagaa cgucgugaga caguucgguc ccuaucugcc gugggcgcug gagaacugag | 2640 |
| gggggcugcu ccuaguacga gaggaccgga gguggacgcau cacgugugu cggguugca | 2700 |
| ugccaauggc acugcccggu agcuaaaugc ggaagagaua agucugaaa gcaucuaagc | 2760 |
| acgaaacuug ccccgagaug aguucccccu gacccuuuaa gggucugaa ggaacguuga | 2820 |
| agacgacgac guugauaggc cgggugugua agcgcagcga ucgcuugagc uaaccgguac | 2880 |
| uaaugaaccg ugaggcuuaa ccuu | 2904 |

<210> SEQ ID NO 2
<211> LENGTH: 2903
<212> TYPE: RNA
<213> ORGANISM: Escherichia coli

<400> SEQUENCE: 2

| | |
|---|---|
| gguuaagcga cuaagcguac acgguggaug cccuggcagu cagaggcgau gaaggacgug | 60 |
| cuaaucugcg auaagcgucg guaaggugau augaaccguu auaaccggcg auuuccgaau | 120 |
| ggggaaaccc agugguuuc gacacacuau cauuaacuga auccauaggu uaaugaggcg | 180 |
| aaccggggga acugaaacau cuaaguaccc cgaggaaaag aaaucaaccg agauucccc | 240 |
| aguagcggcg agcgaacggg gagcagccca gagccugaau cagugugugu guuaguggaa | 300 |
| gcgucggaa aggcgcgcga uacaggguga cagccccgua cacaaaaaug cacaugcugu | 360 |
| gagcucgaug aguagggcgg gacacgguggu auccugucug aauauggggg gaccauccuc | 420 |
| caaggcuaaa uacuccugac ugaccgauag ugaaccagua ccgugaggga aaggcgaaaa | 480 |
| gaaccccggc gaggggagug aaaaagaacc ugaaaccgug uacguacaag cagggagc | 540 |
| acgcuuaggc gugugacugc guaccuuuug uauaauggu cagcgacuua uaucuguag | 600 |
| caagguuaac cgauagggg agccgaaggg aaaccgaguc uuaacugggc guuaaguugc | 660 |
| agggauauaga cccgaaaccc ggugaucuag ccauggcag uugaagguu gguuaacacu | 720 |
| aacuggagga ccgaaccgac uaauguugaa aaauuagcgg augacuugug gcuggggug | 780 |

```
aaaggccaau caaaccggga gauagcuggu ucuccccgaa agcuauuuag guagcgccuc    840
gugaauucau cuccggggu agagcacugu uucggcaagg gggucauccc gacuuaccaa     900
cccgaugcaa acugcgaaua ccggagaaug uuaucacggg agacacacgg cgggugcuaa    960
cguccgucgu gaagagggaa acaacccaga ccgccagcua agucccaaa gucaugguua    1020 agugggaaac gaugugggaa ggcccagaca gccaggaugu uggcuuagaa gcagccauca   1080
uuuaaagaaa gcguaauagc ucacggucg agucggccug cgcggaagau guaacggggc    1140
uaaaccaugc accgaagcug cggcagcgac acuaugguu guugggguagg ggagcguucu   1200 guaagccugu gaaggugugc ugugaggcau gcuggaggua ucagaagugc gaaugcugac   1260
auaaguaacg auaaagcggg ugaaaagccc gcucgccgga agaccaaggg uuccugucca   1320
acguuaaucg gggcagggug agucgacccc uaaggcgagg ccgaaaggcg uagucgaugg   1380
gaaacagguu aauauuccug uacuuggugu uacugcgaag gggggacgga gaaggcuaug   1440
uuggccgggc gacgguuguc ccgguuuaag cguguaggcu gguuuuccag gcaaauccgg   1500
aaaaucaagg cugaggcgug augacgaggc acuacggugc ugaagcaaca aaugcccugc   1560
uuccaggaaa agccucuaag aaucagguaa caucaaaucg uaccccaaac cgacacaggu   1620
ggucagguag agaauaccaa ggcgcuugag agaacucggg ugaaggaacu aggcaaaaug   1680
gugccguaac uucgggagaa ggcacgcuga uauguaggug aagucccucg cggauggagc   1740
ugaaaucagu cgaagauacc agcuggcugc aacuguuuau uaaaaacaca gcacugugca   1800
aacacgaaag uggacguaua cggugugacg ccugcccggu gccggaaggu uaauugaugg   1860
gguuagcgca agcgaagcuc uugaucgaag ccccgguaaa cggcggccgu aacuauaacg   1920
guccuaaggu agcgaaauuc cuugucgggu aaguuccgac cugcacgaau ggcguaauga   1980
uggccaggcu gucccacccc gagacucagu gaaauugaac ucgcugugaa gaugcagugu   2040
acccgcggca agacggaaag accccgugaa ccuuuacuau aacuugacac ugaacauuga   2100
gccuugaugu guaggauagg ugggaggcuu agaagugugg acgccagucu gcauggagcc   2160
gaccuugaaa uaccacccuu uaauguuuga uguucuaacg uugacccgua auccggguug   2220
cggacagugu cuggugggua guugacugg ggcggucucc uccuaaagag uaacggagga   2280
gcacgaaggu uggcuaaucc uggucggaca ucaggagguu agugcaaugg cauaagccag   2340
cuugacugcg agcgugacgg cgcgagcagg ugcgaaagca ggucauagug uccggugguu   2400
ucugaaugga agggccaucg cucaacggau aaaagguacu ccggggauaa caggcugaua   2460
ccgcccaaga guucauaucg acggcggugu uuggcaccuc gaugucggcu caucacaucc   2520 ugggggcugaa guaggucccca agguauggc uguucgccau uuaaaguggu acgcgagcug   2580
gguuuagaac gucgugagac aguucggucc cuaucgccg ugggcgcugg agaacugagg   2640
ggggcugcuc cuaguacgag aggaccggag uggacgcauc acugguguuc ggguugucau   2700
gccaauggca cugcccggua gcuaaaugcg aagagauaa gugcugaaag caucuaagca   2760
cgaaacuugc cccgagauga guucucccug acccuuuaag gguccugaag gaacguugaa   2820
gacgacgacg uugauaggcc gggugugaa gcgcagcgau gcguugagcu aaccgguacu   2880
aaugaaccgu gaggcuuaac cuu                                         2903
```

<210> SEQ ID NO 3
<211> LENGTH: 3777
<212> TYPE: RNA
<213> ORGANISM: Artificial Sequence
<220> FEATURE:
<223> OTHER INFORMATION: synthetic polynucleotide

<400> SEQUENCE: 3

```
agcguucuuu gaagugcuca cacagauugu cugaugaaaa ugagcaguaa aaccucuaca      60
ggcuuguagc ucaggugguu agagcgcacc ccugauaagg gugaggucgg ugguucaagu     120
ccacucaggc cuaccaaauu ugcacggcaa auuugaagag guuuaacuua cauguuaugg     180
ggcuauagcu cagcugggag agcgccugcu uugcacgcag gaggucugcg guucgauccc     240
gcauagcucc accaucucug uagugauuaa auaaaaaaua cuucagagug uaccugcaaa     300
gguucacugc gaaguuuugc ucuuuaaaaa ucuggaucaa gcugaaaauu gaaacacuga     360
acaacgaaag uuguucguga gucucucaaa uuuucgcaac acgaugauga aucgaaagaa     420
acaucuucgg guugugaggu uaagcgacua agcguacacg guggaugccc uggcagucag     480
aggcgaugaa ggacgugcua aucgcgauaa agcgucggua aggugauaug aaccguuaua     540
accggcgauu uccgaauggg gaaacccagu uguuucgac  acacuaucau uaacugaauc     600
cauagguuaa ugaggcgaac cggggggaacu gaaacaucua aguacccccga ggaaaagaaa     660
ucaaccgaga uucccccagu agcggcgagc gaacggggag cagcccagag ccugaaucag     720
ugugugugg u aguggaagcg ucuggaaagg cgucgauac agggacag cccccguacac     780
aaaaaugcac augcugugag cucgaugagu aggggcgggac acgguguauc cugucugaau     840
auggggggac cauccuccaa ggcuaaauac uccugacuga ccgauaguga accaguaccg     900
ugagggaaag gcgaaaagaa ccccggcgag ggagugaaaa agaaccuga aaccguguac     960
guacaagcag ugggagcacg cuuaggcgug ugacugcgua ccuuuguau aaugggucag    1020
cgacuuauau ucuguagcaa gguuaaccga auaggggagc cgaagggaaa ccgagucuua    1080
acugggcguu aaguugcagg guauagaccc gaaacccggu gaucuagcca ugggcagguu    1140
gaagguuggg uaacacuaac uggaggaccg aaccgacuaa uguugaaaaa uuagcggaug    1200
acuuguggcu gggggugaaa ggccaaucaa accgggagau agcugguucu ccccgaaagc    1260
uauuuaggua gcgccucgug aauucaucuc cggggguaga gcacuguuuc ggcaaggggg    1320
ucaucccgac uuaccaaccc gaugcaaacu gcgaauaccg gagaauguua ucacgggaga    1380
cacacggcgg gugcuaacgu ccgucgugaa gagggaaaca acccagaccg ccagcuaagg    1440
ucccaaaguc augguuaagu gggaaacgau gugggaaggc ccagacagcc aggauguugg    1500
cuuugaagca gccaucauuu aaagaaagcg uaauagcuca cuggucgagu cggccugcgc    1560
ggaagaugua acggggcuaa accaugcacc gaagcugcgg cagcgacacu augugu uguu    1620
ggguagggga gcguucugua agccugugaa ggugugcugu gaggcaugcu ggagguauca    1680
gaagugcgaa ugcugacaua aguaacgaua aagcggguga aaagcccgcu cgccggaaga    1740
ccaagggguuc cuguccaacg uuaaucgggg cagggugagu cgaccccuaa ggcgaggccg    1800
aaaggcguag ucgaugggaa acagguuaau auuccuguac uuggguuuac ugcgaagggg    1860
ggacggagaa ggcuauguug gccgggcgac gguugucccg guuuaagcgu guaggcugguu   1920
uuccaggca aauccggaaa aucaaggcug aggcgugaug acgaggcacu acggugcuga    1980
agcaacaaau gcccugcuuc caggaaaagc cucuaagcau caggauacau caaaucguac    2040
cccaaaccga cacaggugug caggauagaga auaccaaggc gcuuuagaga acucgggguga    2100
aggaacuagg caaaauggug ccguaacuuc gggagaaggc acgcugauau uaggugaag    2160
cgacuugcuc guggagcuga aaucagucga agauaccagc uggcugcaac uguuuauuaa    2220
aaacacagca cugugcaaac acgaaagugg acguauacgg ugugacgccu gcccgguggcc   2280
```

| | |
|---|---:|
| ggaagguuaa uugauggggu uagccgcaag gcgaagcucu ugaucgaagc cccgguaaac | 2340 |
| ggcggccgua acuauaacgg uccuaaggua gcgaaauucc uugucgggua aguuccgacc | 2400 |
| ugcacgaaug gcguaaugau ggccaggcug ucuccacccg agacucagug aaauugaacu | 2460 |
| cgcugugaag augcagugua cccgcggcaa gacgagcgug acccgugaac cuuuacuaua | 2520 |
| gcuugacacu gaacauugag ccuugaugug uaggauaggu gggaggcuuu gaagugugga | 2580 |
| cgccagucug caugggagccg accugaaau accacccuuu aauguuugau guucuaacgu | 2640 |
| ugacccguaa uccggguugc ggacaguguc uggugggguag uuugacuggg gcggucuccu | 2700 |
| ccuaaagagu aacggaggag cacgaagguu ggcuaauccu ggucggacau caggagguua | 2760 |
| gugcaauggc auaagccagc uugacugcga gcgugacggc gcgagcaggu gcgaaagcag | 2820 |
| gucauaguga uccggugguu cugaauggaa gggccaucgc ucaacggaua aaagguacuc | 2880 |
| cggggauaac aggcugauac cgcccaagag uucauaucga cggcggguguu uggcaccucu | 2940 |
| ggcagggcuc aucacauccu gggggcugaag uaggucccaa ggguauggcu guucgccauu | 3000 |
| uaaagugguaa cgcgagcugg guuuagaacg ucgagacaa guucggucccc uaucugccgu | 3060 |
| gggcgcugga gaacugaggg gggcugcucc uaguacgaga ggaccggagu ggacgcauca | 3120 |
| cugguguucg gguugucaug ccaauggcac ugcccgguag cuaaaugcgg aagagauaag | 3180 |
| ugcugaaagc aucuaagcac gaaacuugcc ccgagaugag uucucccuga cuccuugaga | 3240 |
| guccugaagg aacguugaag acgacgacgu ugauaggccg ggugugaag cgcagcgaug | 3300 |
| cguugagcua accgguacua augaaccgug aggcuuaacc uuacaacgcc gaaggucuuu | 3360 |
| uggcggauug agagaagauu uucagccuga uacagauuaa aucagaacgc agaagcgguc | 3420 |
| ugauaaaaca gaauuugccu ggcggcagua gcgcggugguu cccaccugac cccaugccga | 3480 |
| acucagaagu gaaacgccgu agcgccgaug uaguguggg gucuccucau gcagagaag | 3540 |
| ggaacugcca ggcaucaaau aaaacgaaag gcucagucgg aagacugggc cuuucguuuu | 3600 |
| aucuguuguu ugucggugaa cgcucuccug aguaggacaa auccgccggg agcggauuug | 3660 |
| aacguugcga agcaacggcc cggagggugg cgggcaggac gcccgccaua aacugccagg | 3720 |
| caucaaauua agcagaaggc cauccugacg gauggccuuu uugcauuggc gcagaaa | 3777 |

<210> SEQ ID NO 4
<211> LENGTH: 3777
<212> TYPE: RNA
<213> ORGANISM: Artificial Sequence
<220> FEATURE:
<223> OTHER INFORMATION: synthetic polynucleotide

<400> SEQUENCE: 4

| | |
|---|---:|
| agcguucuuu gaagugcuca cacagauugu cugaugaaaa ugagcaguaa aaccucuaca | 60 |
| ggcuuguagc ucaggugguu agagcgcacc ccugauaagg gugaggucgg ugguucaagu | 120 |
| ccacucaggc cuaccaaauu ugcacggcaa auugaagag guuuaacua cauguuaugg | 180 |
| ggcuauagcu cagcugggag agcgccgcu ugcacgcag gaggucugcg guucgauccc | 240 |
| gcauagcucc accaucucug uagugauuaa auaaaaaua cuucagagug uaccugcaaa | 300 |
| gguucacugc gaaguuugc ucuuuaaaaa ucuggaucaa gcugaaaauu gaaacacuga | 360 |
| acaacgaaag uuguucguga gucucucaaa uuuucgcaac acgaugauga aucgaaagaa | 420 |
| acaucuucgg guugugaggu uaagcgacua agcguacacg guggaugccc uggcagucag | 480 |
| aggcgaugaa ggacgugcua aucgcgauaa agcgucggua aggugauaug aaccguuaua | 540 |
| accggcgauu uccgaauggg gaaacccagu guguucgac acacuaucau uaacugaauc | 600 |

```
cauagguuaa ugaggcgaac cgggggaacu gaaacaucua aguacccga ggaaaagaaa      660 ucaaccgaga uuccccagu agcggcgagc gaacggggag cagcccagag ccugaaucag      720 ugugugguu aguggaagcg ucuggaaagg cgugcgauac agggugacag ccccguacac      780
aaaaaugcac augcugugag cucgaugagu agggcggac acgugguauc cugucugaau      840
auggggggac cauccuccaa ggcuaaauac uccugacuga ccgauaguga accaguaccg      900
ugagggaaag gcgaaaagaa ccccggcgag gggagugaaa agaaccuga aaccguguac      960 guacaagcag ugggagcacg cuuaggcgug ugacugcgua ccuuuguau aaugggucag     1020 cgacuuauau ucuguagcaa gguuaaccga auagggagc cgaagggaaa ccgagucuua     1080
acugggcguu aaguugcagg guauagaccc gaaacccggu gaucuagcca uggggcagguu    1140 gaagguuggg uaacacuaac uggaggaccg aaccgacuaa uguugaaaaa uuagcggaug     1200 acuguggcu gggggugaaa ggccaaucaa accgggagau agcugguucu ccccgaaagc     1260
uauuuaggua gcgccucgug aauucaucuc cgggguaga gcacuguuuc ggcaagggg     1320 ucaucccgac uuaccaaccc gaugcaaacu gcgaauaccg agaauguuua cacgggaga    1380 cacacgcgg gugcuaacgu ccgucgugaa gagggaaaca acccagaccg ccagcuaagg     1440
ucccaaaguc augguuaagu gggaaacgau gugggaaggc ccagacagcc aggauguugg     1500
cuuugaagca gccaucauuu aaagaaagcg uaauagcuca cuggucgagu cggccugcgc     1560
ggaagaugua acggggcuaa accaugcacc gaagcugcgg cagcgacacu auguguuguu     1620 ggguaggga gcguucugua agccugugaa ggugugcugu gaggcaugcu ggagguauca     1680
gaagugcgaa ugcugacaua aguaacgaua aagcgggugaaaagcccgcu cgccggaaga     1740 ccaagguuc cuguccaacg uuaaucgggg cagggugagu cgaccccuaa ggcgaggccg    1800
aaaggcguag ucgaugggaa acagguuaau auuccuguac uuggguguuac ugcgaagggg    1860 ggacggagaa ggcuauguug gccgggcgac ggugucccg guuuaagcgu guaggcuggu     1920 uuccaggca aauccggaaa aucaaggcug aggcgugaug acgaggcacu acggugcuga     1980
agcaacaaau gcccugcuuc caggaaaagc cucuaagcau caguaacau caaaucguac     2040 cccaaaccga cacagguggu caggaagaga auaccaaggc gcuugagaga acucgggga     2100 aggaacuagg caaaaugguug ccguaacuuc gggagaaggc acgcugauau guaggugaag    2160
cgacuugcuc guggagcuga aaucagucga agauaccagc uggcugcaac uguuuauuaa     2220
aaacacagca cugugcaaac acgaaagugg acguauacgg ugugacgccu gcccggugcc     2280
ggaagguuaa uugaugggu uagcgcaag gcgaagcucu ugaucgaagc cccgguaaac     2340
ggcggccgua acuauaacgg uccuaaggua gcgaaauucc uugucgggua aguuccgacc     2400
ugcacgaaug gcguaaugau ggccaggcug ucuccaccg agacagug aaaugaacu      2460 cgcugugaag augcagugua cccgcggcaa gacgagcgug acccgugaac cuuuacuaua     2520
gcuugacacu gaacauugag ccuugaugug uaggauaggu gggaggcuuu gaagugugga    2580
cgccagucug cauggagccg accuugaaau accacccuuu aauguuugau guucuaacgu     2640
ugaccccuua uccggguugc ggacagucu gguggguag uuugacggg gcggucuccu      2700 ccuaaagagu aacggaggag cacgaagguu ggcuaauccu ggcgacau caggagguua      2760 gugcaauggc auaagccagc uugacugcga gcgugacggc gcgagcaggu gcgaaagcag     2820
gucauaguga uccggugguu cugaauggaa gggccaucgc ucaacggaua aaaggguacuc     2880 cggggauaac aggcugauac cgcccaagag uucauaucga cggcgugguu uggcaccucu     2940
```

| | |
|---|---|
| gacuuggcuc aucacauccu ggggcugaag uaggucccaa ggguauggcu guucgccauu | 3000 |
| uaaaguggua cgcgagcugg guuuagaacg ucgugagaca guuccggcccc uaucugccgu | 3060 |
| gggcgcugga gaacugaggg gggcugcucc uaguacgaga ggaccggagu ggacgcauca | 3120 |
| cugguguucg gguugucaug ccaauggcac ugcccgguag cuaaaugcgg aagagauaag | 3180 |
| ugcugaaagc aucuaagcac gaaacuugcc ccgagaugag uucucccuga cuccuugaga | 3240 |
| guccugaagg aacguugaag acgacgacgu ugauaggccg ggugguguaag cgcagcgaug | 3300 |
| cguugagcua accgguacua augaaccgug aggcuuaacc uuacaacgcc gaagguguuu | 3360 |
| uggcggauug agagaagauu uucagccuga uacagauuaa aucagaacgc agaagcgguc | 3420 |
| ugauaaaaca gaauuugccu ggcggcagua gcgcgguggu cccaccugac cccaugccga | 3480 |
| acucagaagu gaaacgccgu agcgccgaug guaguguggg gucuccucau gcgagaguag | 3540 |
| ggaacugcca ggcaucaaau aaaacgaaag gcucagucgg aagacugggc cuuucguuuu | 3600 |
| aucuguugu ugcggugaa cgcucuccug aguaggacaa auccgccggg agcggauuug | 3660 |
| aacguugcga agcaacggcc cggaggguggg cgggcaggac gcccgccaua aacugccagg | 3720 |
| caucaaauua agcagaaggc cauccugacg gauggccuuu uugcauuggc gcagaaa | 3777 |

```
<210> SEQ ID NO 5
<211> LENGTH: 94
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (2)..(2)
<223> OTHER INFORMATION: methylated

<400> SEQUENCE: 5
```

| | |
|---|---|
| tggagcggga aacgagactc gaactcgcga ccccgacctt ggcaaggtcg tgctctacca | 60 |
| actgagctat tcccgcctat agtgagtcgt atta | 94 |

```
<210> SEQ ID NO 6
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 6
```

| | |
|---|---|
| catatgtaat acgactcact atag | 24 |

```
<210> SEQ ID NO 7
<211> LENGTH: 160
<212> TYPE: PRT
<213> ORGANISM: Artificial Sequence
<220> FEATURE:
<223> OTHER INFORMATION: synthetic polypeptide

<400> SEQUENCE: 7
```

Met His His His His His His Glu Asn Ala Met Pro Trp Asn Leu Pro
1               5                   10                  15

Ala Asp Leu Ala Trp Val Lys Arg Asn Thr Leu Asn Lys Pro Val Ile
            20                  25                  30

Met Gly Arg His Thr Trp Glu Ser Ile Gly Arg Pro Leu Pro Gly Arg
        35                  40                  45

Lys Asn Ile Ile Leu Ser Ser Gln Pro Gly Thr Asp Asp Arg Val Thr
    50                  55                  60

```
Trp Val Lys Ser Val Asp Glu Ala Ile Ala Ala Cys Gly Asp Val Pro
65                  70                  75                  80

Glu Ile Met Val Ile Gly Gly Arg Val Tyr Glu Gln Leu Leu Pro
                85                  90                  95

Lys Ala Gln Lys Leu Tyr Leu Thr His Ile Asp Ala Glu Val Glu Gly
            100                 105                 110

Asp Thr His Tyr Pro Asp Tyr Glu Pro Asp Asp Trp Glu Arg Val Phe
        115                 120                 125

Ser Glu Tyr His Asp Ala Asp Ala Gln Asn Ser His Ser Tyr Cys Tyr
130                 135                 140

Glu Ile Leu Glu Arg Arg Gly Ser Arg Ser His His His His His
145                 150                 155                 160

<210> SEQ ID NO 8
<211> LENGTH: 23
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: alpha-Phe

<400> SEQUENCE: 8

Val Xaa Ser Glu Tyr His Asp Ala Asp Ala Gln Asn Ser His Ser Tyr
1               5                   10                  15

Cys Tyr Glu Ile Leu Glu Arg
            20

<210> SEQ ID NO 9
<211> LENGTH: 23
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: beta3-Br-hPhe

<400> SEQUENCE: 9

Val Xaa Ser Glu Tyr His Asp Ala Asp Ala Gln Asn Ser His Ser Tyr
1               5                   10                  15

Cys Tyr Glu Ile Leu Glu Arg
            20
```

We claim:

1. A 23S rRNA comprising;
at least 85% sequence identity to any of SEQ ID NOS:1-4 and the sequence UGACUU at the positions corresponding to nucleotides 2502-2507 of *E. coli* wild type 23S rRNA (SEQ ID NO:1),
wherein a ribosome comprising the 23S rRNA can catalyze the covalent transfer of a $B^3$ amino acid from an aminoacyl-tRNA onto a nascent peptide chain.

2. The 23S rRNA of claim 1 comprising the sequence AGCGUGA at positions corresponding to nucleotides 2057-2063 of *E. coli* wildtype 23S rRNA (SEQ ID NO:1).

3. The 23S rRNA of claim 1, comprising a truncated 5' end, a truncated 3' end, or a combination thereof relative to *E. coli* wildtype 23S rRNA (SEQ ID NO:1).

4. The 23S rRNA of claim 1, comprising one or more additional insertions, deletions or substitutions relative to *E. coli* wildtype 23S rRNA (SEQ ID NO:1).

5. The 23S rRNA of claim 1 comprising the peptidyl transferase center of *E. coli* wildtype 23S rRNA (SEQ ID NO:1) with the sequence UGACUU substituted at the positions corresponding to nucleotides 2502-2507 and the sequence AGCGUGA substituted at the positions corresponding to nucleotides 2057-2063 of *E. coli* wildtype 23S rRNA (SEQ ID NO:1).

6. The 23S rRNA of claim 1 comprising the domain V of *E. coli* wildtype 23S rRNA (SEQ ID NO:1) with the sequence UGACUU substituted at the positions corresponding to nucleotides 2502-2507 and the sequence AGCGUGA substituted at the positions corresponding to nucleotides 2057-2063 of *E. coli* wildtype 23S rRNA (SEQ ID NO:1).

7. The 23S rRNA of claim 1, wherein the 23S rRNA comprises the nucleic acid sequence of SEQ ID NO:4 or a functional fragment thereof.

8. The 23S rRNA of claim 1, wherein the 23S rRNA comprises the nucleic acid sequence of SEQ ID NO:4.

9. A ribosome comprising the 23S rRNA of claim 1.

10. A polynucleotide encoding the 23S rRNA of claim 1.

11. A vector comprising the polynucleotide of claim 10 operably linked to an expression control sequence.

12. A host cell comprising the 23S rRNA of claim 1.

13. A host cell comprising the polynucleotide of claim 10.

14. A host cell comprising the vector of claim 11.

15. The host cell of claim 13 wherein a polynucleotide encoding the 23S rRNA is integrated into the genome of the host cell.

16. A method for site specific incorporation of a $\beta^3$ amino acid into a target protein, comprising expressing a messenger RNA (mRNA) encoding the target protein in a system comprising:

canonical amino acids, at least one $\beta^3$ amino acid, ribosomes, aminoacyl tRNA synthetases, tRNAs, and EF-Tu, wherein the ribosomes comprise the 23S rRNA of claim 1;

at least one aminoacyl tRNA synthetase (AARS) that can aminoacylate a tRNA with the $\beta^3$ amino acid;

at least one tRNA that can be aminoacylated with the $\beta^3$ amino acid to form an aminoacyl-tRNA that recognizes at least one codon in the mRNA encoding the target protein;

an elongation factor (EF-TU) that binds the aminoacylated with the $\beta^3$ amino acid; and wherein the aminoacyl-tRNA with the $\beta^3$ amino acid recognizes at least one codon such that the $\beta^3$ amino acid is incorporated into a protein or polypeptide during translation.

17. A 23S rRNA comprising at least 90% sequence identity to the nucleic acid sequence of SEQ ID NO:4, wherein the nucleotides corresponding to 2940-2945 of SEQ ID NO: 4 are UGACUU.

18. The 23S rRNA of claim 17 comprising the domain V of SEQ ID NO:4.

19. The 23S rRNA of claim 18 comprising the peptidyl transferase center of SEQ ID NO:4.

20. A 23S rRNA comprising the nucleic acid sequence of SEQ ID NO:4.

* * * * *